United States Patent
Weinstock et al.

(10) Patent No.: US 11,447,755 B2
(45) Date of Patent: Sep. 20, 2022

(54) **GENETICALLY ENGINEERED *VIBRIO* SP. AND USES THEREOF**

(71) Applicant: CODEX DNA, INC., San Diego, CA (US)

(72) Inventors: Matthew T Weinstock, San Diego, CA (US); Christopher M. Wilson, San Diego, CA (US); Eric D. Hesek, Carlsbad, CA (US)

(73) Assignee: Codex DNA, Inc., San Diego, CA (US)

( * ) Notice: Subject to any disclaimer, the term of this patent is extended or adjusted under 35 U.S.C. 154(b) by 305 days.

(21) Appl. No.: 16/525,349

(22) Filed: Jul. 29, 2019

(65) Prior Publication Data

US 2020/0010816 A1    Jan. 9, 2020

Related U.S. Application Data

(62) Division of application No. 15/367,106, filed on Dec. 1, 2016, now Pat. No. 10,377,997.

(60) Provisional application No. 62/261,758, filed on Dec. 1, 2015.

(51) Int. Cl.
| | |
|---|---|
| *C12N 1/20* | (2006.01) |
| *C12N 15/74* | (2006.01) |
| *C12N 9/12* | (2006.01) |
| *C12P 21/00* | (2006.01) |
| *C12P 19/34* | (2006.01) |

(52) U.S. Cl.
CPC ............ *C12N 9/1247* (2013.01); *C12P 19/34* (2013.01); *C12P 21/00* (2013.01); *C12Y 207/07006* (2013.01)

(58) Field of Classification Search
None
See application file for complete search history.

(56) References Cited

U.S. PATENT DOCUMENTS

2013/0005590 A1 * 1/2013 Lou ................ C12N 15/79
435/254.2

OTHER PUBLICATIONS

Weinstock et al., Nat. Methods 13:849-851, Aug. 2016 (Year: 2016).*
Borgeaud et al., PLoS One 8:e53952, 2013, 10 pages (Year: 2013).*
Heidelberg et al., Nature 406:477-484, 2000 (Year: 2000).*
Hirst et al., Proc. Natl. Acad. Sci. 81:7752-7756, 1984 (Year: 1984).*
Blokesch et al., J. Bacteriol. 190:7232-7240, 2008 (Year: 2008).*
Barer, M. R., Medical Microbiology (Eighteenth Edition), New York, 2012, pp. 39-53 (Year: 2012).*
Aiyar et al., J. Bact., 184, 5, 1349-1358, (Year: 2002).
Altschul (1997), Nucleic Acids Res. 25, 3389-3402.
Altschul (1994), Nature Genetics 6, 119-129.
Gerdes, Fees Lett. 389:44-47, 1996.
Giacomin, Plant Sci. 116:59-72, 1996.
Henikoff (1992), Proc. Natl. Acad. Sci. USA 89, 10915-10919.
Jefferson, EMBO J. 6:3901-3907, 1997.
Karlin (1990), Proc. Natl. Acad. Sci. USA 87, 2264-2268).
Panda et al. J. Biosci., 20, 3, 367-376 (Year: 1995).
Schulz (1979) Principles of Protein Structure, Springer-Verlag.
Srikantha, J Bacterial. 178: 121 1996.

* cited by examiner

*Primary Examiner* — David Steadman
(74) *Attorney, Agent, or Firm* — DLA Piper LLP (US)

(57) ABSTRACT

The present disclosure relates to the seminal discovery of a generation and use of genetically engineered *Vibrio* sp. Provided is the use of the genetically engineered bacteria for the construction, maintenance, manipulation, and/or propagation of DNA constructs; protein expression; protein secretion; vectors and other metabolic tools; metabolic engineering; expression of cellular extracts for cell-free biology; shuttle vectors; cloning vectors; and for synthetic biology applications. The disclosure also relates to the use of the replication machinery of *Vibrio* sp. as a cloning or expression vector for replication of recombinant DNA constructs. The disclosure also relates to methods of use of the above.

18 Claims, 17 Drawing Sheets

Specification includes a Sequence Listing.

WHITE LIGHT IMAGE

BLUE LIGHT TRANSILLUMINATOR

SEQUENCE LISTING

```
<160> NUMBER OF SEQ ID NOS: 25

<210> SEQ ID NO 1
<211> LENGTH: 5544
<212> TYPE: DNA
<213> ORGANISM: Vibrio natriegens chrII
<220> FEATURE:
<221> NAME/KEY: misc_feature
<223> OTHER INFORMATION: replication machinery

<400> SEQUENCE: 1
aacaactggc ataaaaaaac cgcccgaagg cggttgaagt tttgattaac gttattgcaa      60
tttgctgtga acaaaagcaa gaatttcttc catcaaacta tcatctactt tttttaaggtt    120 cagtgccaga ttactgcctt tgcggctgta actcgcgcga cctttttatca aatcgactt     180 gtctaccttt ggcgatggtt tggctggtga taattcagta atccaacttt ctaggctttc    240
tgtgacttct tttgttagac gagcaacacc ttgcgctgtg ctacgctgcc acaagtatcc    300
gtctgttgta cggcatttat ctaacaaccc ttgctgatgt tcagggctta gattcgtaaa    360
ctgcttgtgc aatttaacaa tggttgggcg accaaggtcg ccaacatttg gatacgcttg    420
aagcaactct agtggtaaag aagccgcttt taacgctcca cttaccaatg cctcactgca    480
ttggaacatt ttcgccagcg ctttctggtc ttctgcttca ccgctgtcta acttggcttg    540
catctccttg ccttttttcat aaagagagag aggcttgtga gcgtttgcca catcagacag    600
gaacttagca tgattagagt taatgttgtc gccaacataa accagaaaat cttgctcagc    660
cagaatacaa gatttacgac gacgactacc gtctaatacc tcaatcttgc catcttcagt    720
```

```
gcgacggccg acggccggat actgctgacc acgctctttt aacgtaacca atacatcgga    780
taaagcatgc tcattcaaga aagattgttc gcgtgcgtta tcaacaaaga ctgtcgtttc    840
agactcaacc ttgtcagcag gaatacgaac caactcgaat tgaacggtat tctcaccagc    900
gaccgctaac tcaatggttt gcgttttttc ttttgcagcg gtttgcgctt cttgaggcgt    960
agccacgcgg cgtttattag ttttgccaaa taattttgcg tttaattcag acgttttcaa   1020
agccatttac ttattacccc tgattcaatg acggccaatt agagtgcaat acacgctcta   1080
gttcaagtgc gctcttatga acggcgtctt gagcggttgc gagcgttttc ttaccacctt   1140
caaaatcact cacagtgaga tcaaataccg tactgtaggt gtcagcacag gtttcaaacg   1200
ctcgactacg cggaatggta gccatcataa cttggtcacc tagaagatag ttcatttcag   1260
ttaaaacaga aacttgcttc ttattgtcgt cctcaaacat ggttggcatt aagcgcacaa   1320
actcaaggcc attccaatct tctgggaaca tttcatacac tgtcggtaag tgttggaaaa   1380
agtttaccgt tgaagcccag tcaagacgtt tggcagcaca tggaatcagc aatgcgttag   1440
aagcatacat tgcattccaa actagcggat ccacgtgcgg gccggtatca atcatgatga   1500
tatcgaaatc atctgcaata atgtcgataa gctgctcttt taacaaacgc acgtatatcta  1560 aagatgggtc ttcagataag gtttgccacg cttcggcatt aaacatcgcg tcttctggga   1620
aagcagagat tgacttcaag tttggatatt gcgtaggtag caatacattc ttatgcaaaa   1680
actcactatc aatctcaaca ccgtctggta cgttacctaa cataatatca acggcagaat   1740
agatattatc gtgttcagcg acactgattt gtgggtttag gaatagacgt aatgagcctt   1800
gtggatctaa gtcaatcaaa caaatacggt agcgtttatc taagttaagc gctaaacaag   1860
ccgctaaatg caccgccgac atcgatttac ccgtaccacc ctttttggttt tgtacgttga   1920 taatccacgg cttattgcca ttgtttttttt tacgctcgtg gaatttaggc acctcagccg   1980
catccatcag catatgtgct tcttctaacg taatggaata atgattggcg ttattctttg   2040
taaattgatg gccagcggct tccattttac caatcgcgtc atcgagtttt cgacgagtca   2100
aacccgatcg ggtttccatc attgccttag acattggagg gaagtagttg tcacttcgct   2160
cttccaaaac aatctcaata cggtcagctt gaacttgttg tgtgagttct gctaactcat   2220
gaagattttc aatcgttttt tctcttttca tgccaatttc cgttgaaagg atatctgatt   2280
gcaattgtac agcagtgaac accaataaca acaaaaaggt gcacaaacat tttgaataac   2340
aatcacatat aaaaacaata aaatcgactc ttttatgaat tatggtaaaa aatatatcaa   2400
aatataatca aacaagttcg cacaaacgct ttgctaactc tataaattaa aagtgttaca   2460
gcgtcacaca tttacattgt aaattaaaaa ttatacggaa cgattatatt gaccggctaa   2520
attacggatt atgtaaaatc aacatgttta caacaaaaaa tgcagaaacg gggacaagat   2580
tcattcacgg ataccctctt gatcatgctt ccaaagcatt tgaggccgtt tttttaatag   2640
atggaccgga aagatgatca agagagttac ttgatcatct ttccgtgtta tatcctactt   2700
acgaaagcat gatcatggca aaagtagggg agtgcatgag tagatggacg ttattctatg   2760
cgatcaaacc atcggaaaaa tgatcaagtg aataggtttc tcggaagcat gcttttttact   2820 cgccatttta cggacgaatg cagatatact ggggcattca gagaatcaag cgtaaacaaa   2880
cctcggaacg atgaaataaa acatggtat ttgataagta cggctatcat gatcatgctt   2940 cctaaatttta gaacagatat aggatttaca cgcttagtac tgatatctga tgatattttc   3000
agcacatgaa taaattaccg ccgaaatgag actttaactt ggcattaacg ctactcttga   3060
tcatcgatcc ggaaccaagg aggcgataaa atccatggtg tttacacctt tgttgatcaa   3120
```

```
gcaaacccgc atttctgtgg ataacctgta caaatgtcat gatcatcgtt caagaccat    3180 tttgatcatc ttttcagaaa cttaatgatc atgcttacga gaggatatga tcatgctttc   3240
aagatattgt tgatcatcgt ttcgttatat tcatgatcat ggttccgaaa gggatttcaa   3300
taattccttt ttataacaac aacttaaaat gataaaaatt gccagatcaa tagatcatat   3360
aatcaattaa gatcagaata atcaaaaaga tcagttattt aaaaaacaag attttttctt   3420
tatttatgat ctgttttttct ttattcttcg gaaccatagc acaactacgg ctagtgtgat  3480
ctggatctaa aatgatggct gatgaaaaaa ttctgattaa agcaccaaga agccacaaag   3540
acgggcatct ttttgaagtg cacgaatctt ctgcagattg ggtagaacaa taccaacact   3600
tcaaaggggt gaccaaaagc atcttagaat tgcttaatct gatctcgttg agaggtttca   3660
gcagcaaaga tggacttgta tcaaccactg aaatcgttga agcaacagat ggtcaactga   3720
ctcgtgctgc gttacaacaa cgattacgag cagcggtgaa cattggttta tttacgcaaa   3780
ctccagttcg ctttgaagaa ggactggcag gtaaaaccat gcttcacacg tttgttaatc   3840
ccaataagct catttccgct ttgggtgcaa cgagcttagt tactgaaaaa gtccgccaga   3900
atgaaaaaca aaaacgctca aaagcactag ctcagacgca agtaaacaaa cgcttgctga   3960
cagaacatgg cttaaacacg ccgccgacga tgaaagatga agcggatcaa ttcgtcgtct   4020
ctccaactaa ttgggcaggg atcattgacc aagctttggc gccaccacgt actcgtaaga   4080
gttatcagaa gtcgatggtg tcgatctctg gtacgaaagc ggtaatagaa actcgatcgt   4140
caaaaaatat catgacagtc gatgatctga tgaccttgtt tgcgctgttt accctgaccg   4200
tgcaatacca tgatcatcac aaagatcagt accatcttga tgcagctcat gtaccgaata   4260
aaacaccgct gtatatcacc gacatcctgt cattgcgtgg caaaaaggac agtggacctg   4320
ctcgtgattc cattcgtgac agtatcgata gaatcgaatt caccgacttc cagttacatg   4380
agcttacagg ccgctggtta agtgaaaaca tgccggaagg ttttaaaagt gatcgattcc   4440
gctttctagc gcgaacgatc accgcatcag aagaagcgcc agttgagggc agcgacggtg   4500
agatccgaat caaacctaat ttgtacatat tggtttggga ccgtcgtttt acgaggaat    4560 tactgactcg tgattacttc ttcctgtttc cgccagagat tctgaaacaa catactttgg   4620
tgttccagtt atattccttt ttccgtagcc ggatggttcg tcgccatacg gattgtatgt   4680
tgcttagtga actgaatcag aagttagcgc gtaacatcga gtggcgtcga ttctccatgg   4740
atcttatccg ggaactgaaa cgattatctg atggaaaagg gacggaagat cttttttgttg  4800 ttaacttatg gggctaccac ctgacgatcg aaaccatgat cgagaaaggc aaaatcatgg   4860
attaccagat cgatatcaag tgtgatgttg aggaagtctt gcgttattca cgtgctcgta   4920
ccacaaacgc aggaaagcgt aacatggctc ctacgctgcc aaacccactt cgtaatgaga   4980
tggtatccaa acaacagcta gaagagctct caggcatcat tgacggcgaa tttgagccta   5040
ttcagcgcaa agcaccgtct cctcgtggta atttagggcg taggatcaag caaagaaaac   5100
atctggttga gattaatgca gatgaaatta ccattactct atccaaatat acctcaccag   5160
aggctctgga acgcagcata acggcgttat cagcaatgac agggcactca tacgcctcga   5220
ttaaggaaga gtgctctgag tacattgaga agcttgattg gttaagagtt ggagatgacc   5280
cattacctta tgagactctg agtaagaccg ttgagctgtt caatacgcaa aatgatctca   5340
aacatcttac tattgagcgt ctgattgccg gtttagctgt tcgtcgcaag gtctgcagac   5400 aaattttatga tggccatatg gatgagatgg tgtatcgagc tcttgatgaa atggcgattt   5460
```

```
aacatcattc agctttatga attgaaaccg attaatgtga ctgattgatt ttaaatgtaa    5520
atatatattt cgataataga aaac                                           5544

<210> SEQ ID NO 2
<211> LENGTH: 799
<212> TYPE: DNA
<213> ORGANISM: Unknown
<220> FEATURE:
<223> OTHER INFORMATION: Synthetic
<220> FEATURE:
<221> NAME/KEY: misc_feature
<223> OTHER INFORMATION: R6K Gamma origin of replication

<400> SEQUENCE: 2
caaccatcat cgatgaattg cttcgttaat acagatgtag gtgttccaca gggtagccag      60
cagcatcctg cgatgcagat ccggatgcca tttcattacc tcttctccg cacccgacat     120 agatccgaag atcagcagtt caacctgttg atagtacgta ctaagctctc atgtttcacg    180
tactaagctc tcatgtttaa cgtactaagc tctcatgttt aacgaactaa accctcatgg    240
ctaacgtact aagctctcat ggctaacgta ctaagctctc atgtttcacg tactaagctc    300
tcatgtttga acaataaaat taatataaat cagcaactta aatagcctct aaggttttaa    360
gttttataag aaaaaaaaga atatataagg cttttaaagc ttttaaggtt taacggttgt    420
ggacaacaag ccagggatct gccatttcat tacctctttc tccgcacccg acatagatcc    480
ggaacataat ggtgcagggc gctgacttcc gcgtttccag actttacgaa acacggaaac    540
cgaagaccat tcatgttgtt gctcaggtcg cagacgtttt gcagcagcag tcgcttcacg    600
ttcgctcgcg tatcggtgat tcattctgct aaccagtaag gcaaccccgc cagcctagcc    660
gggtcctcaa cgacaggagc acgatcatgc gcacccgtgg ccaggaccca cgctgcccg     720 agatgcgccg cgtgcggctg ctggagatgg cggacgcgat ggatatgttc tgccaagggt    780
tggtttgcgc attcacagg                                                 799

<210> SEQ ID NO 3
<211> LENGTH: 2727
<212> TYPE: DNA
<213> ORGANISM: Unknown
<220> FEATURE:
<223> OTHER INFORMATION: Synthetic
<220> FEATURE:
<221> NAME/KEY: misc_feature
<223> OTHER INFORMATION: tetA/tetR resistance genes + RP4 oriT

<400> SEQUENCE: 3
ccgtcgatct atctcatctg cgcaaggcag aacgtgaaga cggccgccct ggacctcgcc      60
cgcgagcgcc agcgcacgag gccggcgcgc ggacccgccg cggcccacga gcggacgccg    120
cagcaggagc gccagaaggc cgccagagag gccgagcgcg gcgtgaggct tggacgctag    180
ggcagggcat gaaaaagccc gtagcgggcg ctacggggct ctgacgcggt ggaaggggg    240 agggggatgtt gtctacatgg ctctgctgta gtgagtgggt tgcgctccgg cagcggtcct    300
gatcaatcgt caccctttct cggtccttca acgttcctga caacgagcct cctttttcgcc    360 aatccatcga caatcaccgc gagtccctgc tcgaacgctg cgtccggacc ggcttcgtcg    420
aaggcgtcta tcgcggcccg caacagcggc gagagcggag cctgttcaac ggtgccgccg    480
cgctcgccgg actcgctgtc gccgcctgc tcctcaagca cggccccaac agtgaagtag    540
ctgattgtca tcagcgcatt gacggcgtcc ccggccgaaa acccgcctc gcagaggaag    600 cgaagctgcg cgtcggccgt ttccatctgc ggtgcgcccg gtcgcgtgcc ggcatggatg    660
```

```
cgcgcgccat cgcggtaggc gagcagcgcc tgcctgaagc tgcgggcatt cccagtcaga    720
aatgagcgcc agtcgtcgtc ggctctcggc accgaagtgc tatgattctc cgccagcatg    780
gcttcggcca gtgcgtcgag cagcgcccgc ttgttcctga agtgccagta aagcgccggc    840
tgctgaaccc ccaaccgttc cgccagtttg cgtgtcgtca ccgtctac gccgacctcg      900
ttcaacaggt ctagggcggc acggatcact gtattcggct gcaactttgt catgcttgac    960
actttatcac tgataaacat aatatgtcca ccaacttatc agtgataaag aatccgcgcg   1020
ttcaatcgga ccagcggagg ctggtccgga ggccagacgt gaaacccaac ataccctga    1080
tcgtaattct gagcactgtc gcgctcgacg ctgtcggcat cggcctgatt atgccggtgc   1140
tgccgggcct cctgcgcgat ctggttcact cgaacgacgt caccgcccac tatggcattc   1200
tgctggcgct gtatgcgttg gtgcaatttg cctgcgcacc tgtgctgggc gcgctgtcgg   1260
atcgtttcgg gcggcggcca atcttgctcg tctcgctggc cggcgccact gtcgactacg   1320
ccatcatggc gacagcgcct ttcctttggg ttctctatat cgggcggatc gtggccggca   1380
tcaccggggc gactggggcg gtagccggcg cttatattgc cgatatcact gatggcgatg   1440
agcgcgcgcg gcacttcggc ttcatgagcg cctgtttcgg gttcgggatg gtcgcgggac   1500
ctgtgctcgg tgggctgatg ggcggtttct ccccccacgc tccgttcttc gccgcggcag   1560
ccttgaacgg cctcaatttc ctgacgggct gtttccttt gccggagtcg cacaaaggcg    1620
aacgccggcc gttacgccgg gaggctctca acccgctcag cttcgttcgg tgggcccggg   1680
gcatgaccgt cgtcgccgcc ctgatggcgg tcttcttcat catgcaactt gtcggacagg   1740
tgccggccgc gctttgggtc attttcggcg aggatcgctt tcactgggac gcgaccacga   1800
tcggcatttc gcttgccgca tttggcattc tgcattcact cgcccaggca atgatcaccg   1860
gccctgtagc cgcccggctc ggcgaaaggc gggcactcat gctcggaatg attgccgacg   1920
gcacaggcta catcctgctt gccttcgcga cacggggatg gatggcgttc ccgatcatgg   1980
tcctgcttgc ttcgggtggc atcggaatgc cggcgctgca agcaatgttg tccaggcagg   2040
tggatgagga acgccagggg cagctgcaag gctcactggc ggcgctcacc agcctgacct   2100
cgatcgtcgg accctcctc ttcacggcga tctatgcggc ttctataaca acgtggaacg    2160
ggtgggcatg gattgcaggc gctgccctct acttgctctg cctgccggcg ctgcgtcgcg   2220
ggctttggag cggcgcaggg caacgagccg atcgctgatc gtggaaacga tagggacgga   2280
tctgctggcg aaaggggat gtgctgcaag gcgattaagt tgggtaacgc cagggttttc    2340
ccagtcacga cgttgtaaaa cgacggccag tgaattaatt cttgaagacg aaagggcctc   2400
gtgatacgcc tattttata ggttaatgtc atgataataa tggtttctta gagcttacgg    2460
ccagcctcgc agagcaggat tcccgttgag caccgccagg tgcgaataag ggacagtgaa   2520
gaaggaacac ccgctcgcgg gtgggcctac ttcacctatc ctgcccggct gacgccgttg   2580
gatacaccaa ggaaagtcta cacgaaccct ttggcaaaat cctgtatatc gtgcgaaaaa   2640
ggatggatat accgaaaaaa tcgctataat gaccccgaag cagggttatg cagcggaaaa   2700
gatccgtcga tcgacccagg tggcact                                       2727
```

<210> SEQ ID NO 4
<211> LENGTH: 11285
<212> TYPE: DNA
<213> ORGANISM: Artificial Sequence
<220> FEATURE:
<223> OTHER INFORMATION: Synthetic
<220> FEATURE:

<221> NAME/KEY: misc_feature
<223> OTHER INFORMATION: pVnatCII-YACTRP-copycontrol, combo sequence
      from Vibrio natriegens and unknown

<400> SEQUENCE: 4

```
agcttacggc cagcctcgca gagcaggatt cccgttgagc accgccaggt gcgaataagg    60
gacagtgaag aaggaacacc cgctcgcggg tgggcctact tcacctatcc tgcccggctg   120
acgccgttgg ataccaag gaaagtctac acgaaccctt tggcaaaatc ctgtatatcg    180
tgcgaaaaag gatggatata ccgaaaaaat cgctataatg accccgaagc agggttatgc   240
agcggaaaag atccgtcgat cgacccaggt ggcactaaca actggcataa aaaaaccgcc   300
cgaaggcggt tgaagttttg attaacgtta ttgcaatttg ctgtgaacaa agcaagaat   360 ttcttccatc aaactatcat ctactttttt aaggttcagt gccagattac tgcctttgcg   420
gctgtaactc gcgcgacctt ttatcaaatc gactttgtct acctttggcg atggtttggc   480
tggtgataat tcagtaatcc aactttctag gctttctgtg acttcttttg ttagacgagc   540
aacaccttgc gctgtgctac gctgccacaa gtatccgtct gttgtacggc atttatctaa   600
caacccttgc tgatgttcag ggcttagatt cgtaaactgc ttgtgcaatt taacaatggt   660
tgggcgacca aggtcgccaa catttggata cgcttgaagc aactctagtg gtaaagaagc   720
cgcttttaac gctccactta ccaatgcctc actgcattgg aacattttcg ccagcgcttt   780
ctggtcttct gcttcaccgc tgtctaactt ggcttgcatc tccttgcctt tttcataaag   840
agagagaggc ttgtgagcgt tgccacatc agacaggaac ttagcatgat tagagttaat   900
gttgtcgcca acataaacca gaaaatcttg ctcagccaga atacaagatt tacgacgacg   960
actaccgtct aatacctcaa tcttgccatc ttcagtgcga cggccgacgg ccggatactg  1020
ctgaccacgc tcttttaacg taaccaatac atcggataaa gcatgctcat tcaagaaaga  1080
ttgttcgcgt gcgttatcaa caaagactgt cgtttcagac tcaaccttgt cagcaggaat  1140
acgaaccaac tcgaattgaa cggtattctc accagcgacc gctaactcaa tggtttgcgt  1200 ttttcttt gcagcggttt gcgcttcttg aggcgtagcc acgcggcgtt tattagtttt  1260
gccaaataat tttgcgttta attcagacgt tttcaaagcc atttacttat tacccctgat  1320
tcaatgacgg ccaattagag tgcaatacac gctctagttc aagtgcgctc ttatgaacgg  1380
cgtcttgagc ggttgcgagc gttttcttac caccttcaaa atcactcaca gtgagatcaa  1440
ataccgtact gtaggtgtca gcacaggttt caaacgctcg actacgcgga atggtagcca  1500
tcataacttg gtcacctaga agatagttca tttcagttaa aacagaaact tgcttcttat  1560
tgtcgtcctc aaacatggtt ggcattaagc gcacaaactc aaggccattc caatcttctg  1620
ggaacatttc atacactgtc ggtaagtgtt ggaaaaagtt taccgttgaa gcccagtcaa  1680
gacgtttggc agcacatgga atcagcaatg cgttagaagc atacattgca ttccaaacta  1740
gcggatccac gtgcgggccg gtatcaatca tgatgtatc gaaatcatct gcaataatgt  1800
cgataagctg ctctttaac aaacgcacga tatctaaaga tgggtcttca gataaggttt  1860
gccacgcttc ggcattaaac atcgcgtctt ctgggaaagc agagattgac ttcaagtttg  1920
gatattgcgt aggtagcaat acattcttat gcaaaaactc actatcaatc tcaacaccgt  1980
ctggtacgtt acctaacata atatcaacgg cagaatagat attatcgtgt tcagcgacac  2040
tgatttgtgg gttaggaat agacgtaatg agccttgtgg atctaagtca atcaaacaaa  2100
tacggtagcg tttatctaag ttaagcgcta acaagccgc taaatgcacc gccgacatcg  2160
atttacccgt accacccttt tggttttgta cgttgataat ccacggctta ttgccattgt  2220
```

```
tttttttacg ctcgtggaat ttaggcacct cagccgcatc catcagcata tgtgcttctt    2280
ctaacgtaat ggaataatga ttggcgttat tctttgtaaa ttgatggcca gcggcttcca    2340
ttttaccaat cgcgtcatcg agttttcgac gagtcaaacc cgatcgggtt tccatcattg    2400
ccttagacat tggagggaag tagttgtcac ttcgctcttc caaaacaatc tcaatacggt    2460
cagcttgaac ttgttgtgtg agttctgcta actcatgaag attttcaatc gttttttctc    2520
ttttcatgcc aatttccgtt gaaaggatat ctgattgcaa ttgtacagca gtgaacacca    2580
ataacaacaa aaaggtgcac aaacattttg aataacaatc acatataaaa acaataaaat    2640
cgactctttt atgaattatg gtaaaaaata tatcaaaata taatcaaaca agttcgcaca    2700
aacgctttgc taactctata aattaaaagt gttacagcgt cacacattta cattgtaaat    2760
taaaaattat acggaacgat tatattgacc ggctaaatta cggattatgt aaaatcaaca    2820
tgtttacaac aaaaaatgca gaaacgggga caagattcat tcacggatac cctcttgatc    2880
atgcttccaa agcatttgag gccgtttttt taatagatgg accggaaaga tgatcaagag    2940
agttacttga tcatctttcc gtgttatatc ctacttacga aagcatgatc atggcaaaag    3000
taggggagtg catgagtaga tggacgttat tctatgcgat caaaccatcg gaaaaatgat    3060
caagtgaata ggtttctcgg aagcatgctt tttactcgcc attttacgga cgaatgcaga    3120
tatactgggg cattcagaga atcaagcgta aacaaacctc ggaacgatga ataaaaaca    3180 tggtatttga taagtacggc tatcatgatc atgcttccta aatttagaac agatatagga    3240
tttacacgct tagtactgat atctgatgat attttcagca catgaataaa ttaccgccga    3300
aatgagactt taacttggca ttaacgctac tcttgatcat cgatccggaa ccaaggaggc    3360
gataaaatcc atggtgttta cacctttgtt gatcaagcaa acccgcattt ctgtggataa    3420
cctgtacaaa tgtcatgatc atcgtttcaa gaccattttg atcatcttt cagaaactta    3480 atgatcatgc ttacgagagg atatgatcat gctttcaaga tattgttgat catcgtttcg    3540
ttatattcat gatcatggtt ccgaaaggga tttcaataat tcctttttat aacaacaact    3600
taaaatgata aaaattgcca gatcaataga tcatataatc aattaagatc agaataatca    3660
aaaagatcag ttatttaaaa aacaagattt tttctttatt tatgatctgt ttttctttat    3720
tcttcggaac catagcacaa ctacggctag tgtgatctgg atctaaaatg atggctgatg    3780
aaaaaattct gattaaagca ccaagaagcc acaaagacgg gcatcttttt gaagtgcacg    3840
aatcttctgc agattgggta gaacaatacc aacacttcaa agggggtgacc aaaagcatct    3900 tagaattgct taatctgatc tcgttgagag gtttcagcag caaagatgga cttgtatcaa    3960
ccactgaaat cgttgaagca acagatggtc aactgactcg tgctgcgtta caacaacgat    4020
tacgagcagc ggtgaacatt ggtttattta cgcaaactcc agttcgcttt gaagaaggac    4080
tggcaggtaa aaccatgctt cacacgtttg ttaatcccaa taagctcatt tccgctttgg    4140
gtgcaacgag cttagttact gaaaaagtcc gccagaatga aaaacaaaaa cgctcaaaag    4200
cactagctca gacgcaagta aacaaacgct tgctgacaga acatggctta aacacgccgc    4260
cgacgatgaa agatgaagcg gatcaattcg tcgtctctcc aactaattgg gcagggatca    4320
ttgaccaagc tttggcgcca ccacgtactc gtaagagtta tcagaagtcg atggtgtcga    4380
tctctggtac gaaagcggta atagaaactc gatcgtcaaa aaatatcatg acagtcgatg    4440
atctgatgac cttgtttgcg ctgtttaccc tgaccgtgca ataccatgat catcacaaag    4500
atcagtacca tcttgatgca gctcatgtac cgaataaaac accgctgtat atcaccgaca    4560
```

```
tcctgtcatt gcgtggcaaa aaggacagtg gacctgctcg tgattccatt cgtgacagta    4620
tcgatagaat cgaattcacc gacttccagt tacatgagct tacaggccgc tggttaagtg    4680
aaaacatgcc ggaaggtttt aaaagtgatc gattccgctt tctagcgcga acgatcaccg    4740
catcagaaga agcgccagtt gagggcagcg acggtgagat ccgaatcaaa cctaatttgt    4800
acatattggt ttgggagccg tcgttttacg aggaattact gactcgtgat tacttcttcc    4860
tgtttccgcc agagattctg aaacaacata ctttggtgtt ccagttatat tcctttttcc    4920
gtagccggat ggttcgtcgc catacggatt gtatgttgct tagtgaactg aatcagaagt    4980
tagcgcgtaa catcgagtgg cgtcgattct ccatggatct tatccgggaa ctgaaacgat    5040
tatctgatgg aaaagggacg gaagatcttt ttgttgttaa cttatggggc taccacctga    5100
cgatcgaaac catgatcgag aaaggcaaaa tcatggatta ccagatcgat atcaagtgtg    5160
atgttgagga agtcttgcgt tattcacgtg ctcgtaccac aaacgcagga aagcgtaaca    5220
tggctcctac gctgccaaac ccacttcgta atgagatggt atccaaacaa cagctagaag    5280
agctctcagg catcattgac ggcgaatttg agcctattca gcgcaaagca ccgtctcctc    5340
gtggtaattt agggcgtagg atcaagcaaa gaaaacatct ggttgagatt aatgcagatg    5400
aaattaccat tactctatcc aaatatacct caccagaggc tctggaacgc agcataacgg    5460
cgttatcagc aatgacaggg cactcatacg cctcgattaa ggaagagtgc tctgagtaca    5520
ttgagaagct tgattggtta agagttggag atgacccatt accttatgag actctgagta    5580
agaccgttga gctgttcaat acgcaaaatg atctcaaaca tcttactatt gagcgtctga    5640
ttgccggttt agctgttcgt cgcaaggtct gcagacaaat ttatgatggc catatggatg    5700
agatggtgta tcgagctctt gatgaaatgg cgatttaaca tcattcagct ttatgaattg    5760
aaaccgatta atgtgactga ttgattttaa atgtaaatat atatttcgat aatagaaaac    5820
gtcgacgagc tcgcgagctc ggacatgagg ttgccccgta ttcagtgtcg ctgatttgta    5880
ttgtctgaag ttgttttttac gttaagttga tgcagatcaa ttaatacgat acctgcgtca    5940
taattgatta tttgacgtgg tttgatggcc tccacgcacg ttgtgatatg tagatgataa    6000
tcattatcac tttacgggtc cttttccggtg atccgacagg ttacggggcg gcgacctcgc    6060
gggttttcgc tatttatgaa aattttccgg tttaaggcgt ttccgttctt cttcgtcata    6120
acttaatgtt tttatttaaa ataccctctg aaaagaaagg aaacgacagg tgctgaaagc    6180 gagcttttg gcctctgtcg tttcctttct ctgttttgt ccgtggaatg aacaatggaa    6240
gtccgagctc atcgctaata acttcgtata gcatacatta tacgaagtta tattcgatgc    6300
ggccgcaagg ggttcgcgtc agcgggtgtt ggcgggtgtc ggggctggct taactatgcg    6360
gcatcagagc agattgtact gagagtgcac catatgcggt gtgaaatacc acacagatgc    6420
gtaaggagaa aataccgcat caggcgccat tcgccattca gctgcgcaac tgttgggaag    6480 ggcgatcgt gcgggcctct tcgctattac gccagctggc gaaagggga tgtgctgcaa    6540 ggcgattaag ttgggtaacg ccagggtttt cccagtcacg acgttgtaaa acgacggcca    6600
gtgaattgta atacgactca ctatagggcg aattcgagct cggtacccgg ggatcctcta    6660
gagtcgacct gcaggcatgc aagcttgagt attctatagt ctcacctaaa tagcttggcg    6720
taatcatggt catagctgtt tcctgtgtga attgttatc cgctcacaat tccacacaac    6780
atacgagccg gaagcataaa gtgtaaagcc tggggtgcct aatgagtgag ctaactcaca    6840
ttaattgcgt tgcgctcact gcccgctttc cagtcgggaa acctgtcgtg ccagctgcat    6900
taatgaatcg gccaacgcga accccttgcg gccgcccggg ccgtcgacca attctcatgt    6960
```

```
ttgacagctt atcatcgaat ttctgccatt catccgctta ttatcactta ttcaggcgta    7020
gcaaccaggc gtttaagggc accaataact gccttaaaaa aattacgccc cgccctgcca    7080
ctcatcgcag tactgttgta attcattaag cattctgccg acatggaagc catcacaaac    7140
ggcatgatga acctgaatcg ccagcggcat cagcaccttg tcgccttgcg tataatattt    7200
gcccatggtg aaacgggggg cgaagaagtt gtccatattg gccacgttta aatcaaaact    7260
ggtgaaactc acccagggat tggctgagac gaaaaacata ttctcaataa acccttttagg   7320 gaaataggcc aggttttcac cgtaacacgc cacatcttgc gaatatatgt gtagaaactg    7380
ccggaaatcg tcgtggtatt cactccagag cgatgaaaac gtttcagttt gctcatggaa    7440
aacggtgtaa caagggtgaa cactatccca tatcaccagc tcaccgtctt tcattgccat    7500
acgaaattcc ggatgagcat tcatcaggcg ggcaagaatg tgaataaagg ccggataaaa    7560
cttgtgctta ttttttcttta cggtctttaa aaaggccgta atatccagct gaacggtctg    7620
gttataggta cattgagcaa ctgactgaaa tgcctcaaaa tgttctttac gatgccattg    7680
ggatatatca acggtggtat atccagtgat tttttttctcc attttagctt ccttagctcc    7740
tgaaaatctc gataactcaa aaaatacgcc cggtagtgat cttatttcat tatggtgaaa    7800
gttggaacct cttacgtgcc gatcaacgtc tcattttcgc caaaagttgg cccagggctt    7860
cccggtatca cagggacac caggatttat ttattctgcg aagtgatctt ccgtcacagg    7920
tatttattcg cgataagctc atggagcggc gtaaccgtcg cacaggaagg acagagaaag    7980
cgcggatctg ggaagtgacg gacagaacgg tcaggacctg gattggggag gcggttgccg    8040
ccgctgctgc tgacggtgtg acgttctctg ttccggtcac accacatacg ttccgccatt    8100
cctatgcgat gcacatgctg tatgccggta taccgctgaa agttctgcaa agcctgatgg    8160
gacataagtc catcagttca acggaagtct acacgaaggt ttttgcgctg gatgtggctg    8220
cccggcaccg ggtgcagttt gcgatgccgg agtctgatgc ggttgcgatg ctgaaacaat    8280
tatcctgaga ataaatgcct tggcctttat atggaaatgt ggaactgagt ggatatgctg    8340
tttttgtctg ttaaacagag aagctggctg ttatccactg agaagcgaac gaaacagtcg    8400
ggaaaatctc ccattatcgt agagatccgc attattaatc tcaggagcct gtgtagcgtt    8460
tataggaagt agtgttctgt catgatgcct gcaagcggta acgaaaacga tttgaatatg    8520
ccttcaggaa caatagaaat cttcgtgcgg tgttacgttg aagtggagcg gattatgtca    8580
gcaatggaca gaacaaccta atgaacacag aaccatgatg tggtctgtcc ttttacagcc    8640
agtagtgctc gccgcagtcg agcgacaggg cgaagccctc gagctggttg ccctcgccgc    8700
tgggctggcg gccgtctatg gccctgcaaa cgcgccagaa acgccgtcga agccgtgtgc    8760
gagacaccgc ggccggccgc cggcgttgtg gatacctcgc ggaaaacttg gccctcactg    8820
acagatgagg ggcggacgtt gacacttgag gggccgactc acccggcgcg gcgttgacag    8880
atgaggggca ggctcgattt cggccggcga cgtggagctg gccagcctcg caaatcggcg    8940
aaaacgcctg attttacgcg agtttcccac agatgatgtg gacaagcctg gggataagtg    9000
ccctgcggta ttgacacttg aggggcgcga ctactgacag atgaggggcg cgatccttga    9060
cacttgaggg gcagagtgct gacagatgag gggcgcacct attgacattt gaggggctgt    9120
ccacaggcag aaaatccagc atttgcaagg gtttccgccc gttttttcggc caccgctaac    9180 ctgtctttta acctgctttt aaaccaatat ttataaacct tgttttttaac cagggctgcg    9240 ccctgtgcgc gtgaccgcgc acgccgaagg ggggtgcccc cccttctcga accctcccgg    9300
```

```
cagttcgctc gctatgctcg gttacacggc tgcggcgagc atcacgtgct ataaaaataa    9360
ttataattta aattttttaa tataaatata taaattaaaa atagaaagta aaaaagaaaa    9420
ttaaagaaaa aatagttttt gttttccgaa gatgtaaaag actctagggg gatcgccaac    9480
aaatactacc ttttatcttg ctcttcctgc tctcaggtat taatgccgaa ttgtttcatc    9540
ttgtctgtgt agaagaccac acacgaaaat cctgtgattt tacattttac ttatcgttaa    9600
tcgaatgtat atctatttaa tctgcttttc ttgtctaata aatatatatg taaagtacgc    9660
tttttgttga aattttttaa acctttgttt attttttttt cttcattccg taactcttct    9720
accttcttta tttactttct aaaatccaaa tacaaaacat aaaaataaat aaacacagag    9780
taaattccca aattattcca tcattaaaag atacgaggcg cgtgtaagtt acaggcaagc    9840
gatccgtcct aagaaaccat tattatcatg acattaacct ataaaaatag gcgtatcacg    9900
aggccctttc gtctcgcgcg tttcggtgat gacggtgaaa acctctgaca catgcagctc    9960
ccggagacgg tcacagcttg tctgtaagcg gatgccggga gcagacaagc ccgtcagggc   10020
gcgtcagcgg gtgttggcgg gtgtcggggc tggcttaact atgcggcatc agagcagatt   10080
gtactgagag tgcaccataa acgacattac tatatatata atataggaag catttaatag   10140
acagcatcgt aatatatgtg tactttgcag ttatgacgcc agatgcagt agtggaagat    10200 attctttatt gaaaaatagc ttgtcaccct acgtacaatc ttgatccgga gcttttcttt   10260
ttttgccgat taagaattaa ttcggtcgaa aaagaaaag gagagggcca agaggaggg     10320 cattggtgac tattgagcac gtgagtatac gtgattaagc acacaaaggc agcttggagt   10380
atgtctgtta ttaatttcac aggtagttct ggtccattgg tgaaagtttg cggcttgcag   10440
agcacagagg ccgcagaatg tgctctagat tccgatgctg acttgctggg tattatatgt   10500
gtgcccaata gaaagagaac aattgacccg gttattgcaa ggaaaatttc aagtcttgta   10560
aaagcatata aaaatagttc aggcactccg aaatacttgg ttggcgtgtt tcgtaatcaa   10620
cctaaggagg atgttttggc tctggtcaat gattacggca ttgatatcgt ccaactgcat   10680
ggagatgagt cgtggcaaga ataccaagag ttcctcggtt tgccagttat taaaagactc   10740
gtatttccaa aagactgcaa catactactc agtgcagctt cacagaaacc tcattcgttt   10800
attcccttgt ttgattcaga agcaggtggg acaggtgaac ttttggattg gaactcgatt   10860
tctgactggg ttggaaggca agagagcccc gaaagcttac attttatgtt agctggtgga   10920
ctgacgccag aaaatgttgg tgatgcgctt agattaaatg gcgttattgg tgttgatgta   10980
agcggaggtg tggagacaaa tggtgtaaaa gactctaaca aaatagcaaa tttcgtcaaa   11040
aatgctaaga aataggttat tactgagtag tatttattta agtattgttt gtgcacttgc   11100
ctatgcggtg tgaaataccg cacagatgcg taaggagaaa ataccgcatc aggaaattgt   11160
aaacgttaat attttgttaa aattcgcgtt aaatttttgt taaatcagct cattttttaa   11220
ccaataggcc gaaatcggca aaatcgctag tgataataag tgactgaggt atgtgctctt   11280
cttat                                                              11285
```

<210> SEQ ID NO 5
<211> LENGTH: 1217
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: araC-araBAD promoter fragment

<400> SEQUENCE: 5

```
ttatgacaac ttgacggcta catcattcac tttttcttca caaccggcac ggaactcgct    60
cgggctggcc ccggtgcatt ttttaaatac ccgcgagaaa tagagttgat cgtcaaaacc   120
aacattgcga ccgacggtgg cgataggcat ccgggtggtg ctcaaaagca gcttcgcctg   180
gctgatacgt tggtcctcgc gccagcttaa gacgctaatc cctaactgct ggcggaaaag   240
atgtgacaga cgcgacggcg acaagcaaac atgctgtgcg acgctggcga tatcaaaatt   300
gctgtctgcc aggtgatcgc tgatgtactg acaagcctcg cgtacccgat tatccatcgg   360
tggatggagc gactcgttaa tcgcttccat cgccgcagt aacaattgct caagcagatt   420
tatcgccagc agctccgaat agcgcccttc cccttgcccg gcgttaatga tttgcccaaa   480
caggtcgctg aaatgcggct ggtgcgcttc atccgggcga agaaccccg tattggcaaa   540
tattgacggc cagttaagcc attcatgcca gtaggcgcgc ggacgaaagt aaacccactg   600
gtgataccat tcgcgagcct ccggatgacg accgtagtga tgaatctctc ctggcgggaa   660
cagcaaaata tcacccggtc ggcaaacaaa ttctcgtccc tgattttca ccaccccctg   720
accgcgaatg gtgagattga aatataacc tttcattccc agcggtcggt cgataaaaaa   780
atcgagataa ccgttggcct caatcggcgt taaacccgcc accagatggg cattaaacga   840
gtatcccggc agcaggggat cattttgcgc ttcagccata cttttcatac tcccgccatt   900
cagagaagaa accaattgtc catattgcat cagacattgc cgtcactgcg tcttttactg   960
gctcttctcg ctaaccaaac cggtaacccc gcttattaaa agcattctgt aacaaagcgg  1020
gaccaaagcc atgacaaaaa cgcgtaacaa aagtgtctat aatcacggca gaaagtcca  1080
cattgattat ttgcacggcg tcacactttg ctatgccata gcatttttat ccataagatt  1140
agcggatcct acctgacgct ttttatcgca actctctact gtttctccat acccgttttt  1200
ttggatggag tgaaacg                                                  1217
```

<210> SEQ ID NO 6
<211> LENGTH: 1937
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: lac operon regulatory elements and lacI protein

<400> SEQUENCE: 6

```
ttatttgatt tcaattttgt cccactccct gcctctgtca tcacgatact gtgatgccat    60
ggtgtccgac ttatgcccga gaagatgttg agcaaactta tcgcttatct gcttctcata   120
gagtcttgca gacaaactgc gcaactcgtg aaaggtaggc ggatccagat cccggacacc   180
atcgaatggc gcaaaaccct tcgcggtatg gcatgatagc gcccggaaga gagtcaattc   240
agggtggtga atgtgaaacc agtaacgtta tacgatgtcg cagagtatgc cggtgtctct   300
tatcagaccg tttcccgcgt ggtgaaccag gccagccacg tttctgcgaa aacgcgggaa   360
aaagtggaag cggcgatggc ggagctgaat tacattccca accgcgtggc acaacaactg   420
gcgggcaaac agtcgttgct gattggcgtt gccacctcca gtctggccct gcacgcgccg   480
tcgcaaattg tcgcggcgat taaatctcgc gccgatcaac tgggtgccag cgtggtggtg   540
tcgatggtag aacgaagcgg cgtcgaagcc tgtaaagcgg cggtgcacaa tcttctcgcg   600
caacgcgtca gtgggctgat cattaactat ccgctggatg accaggatgc cattgctgtg   660
```

```
gaagctgcct gcactaatgt tccggcgtta tttcttgatg tctctgacca gacacccatc    720
aacagtatta ttttctccca tgaagacggt acgcgactgg gcgtggagca tctggtcgca    780
ttgggtcacc agcaaatcgc gctgttagcg ggcccattaa gttctgtctc ggcgcgtctg    840
cgtctggctg gctggcataa atatctcact cgcaatcaaa ttcagccgat agcggaacgg    900
gaaggcgact ggagtgccat gtccggtttt caacaaacca tgcaaatgct gaatgagggc    960
atcgttccca ctgcgatgct ggttgccaac gatcagatgg cgctgggcgc aatgcgcgcc   1020
attaccgagt ccgggctgcg cgttggtgcg gatatctcgg tagtgggata cgacgatacc   1080
gaagacagct catgttatat cccgccgtta accaccatca acaggatttt cgcctgctg    1140 gggcaaacca gcgtggaccg cttgctgcaa ctctctcagg gccaggcggt gaagggcaat   1200
cagctgttgc ccgtctcact ggtgaaaaga aaaccaccc tggcgcccaa tacgcaaacc    1260
gcctctcccc gcgcgttggc cgattcatta atgcagctgg cacgacaggt ttcccgactg   1320
gaaagcgggc agtgagcgca acgcaattaa tgtaagttag ctcactcatt aggcacccca   1380
ggctttacac tttatgcttc cggctcgtat aatgtgtgga attgtgagcg gataacaatt   1440
tcacacagga aacagctatg accatgatta cggattcact ggccgtcgtt ttacaacgtc   1500
gtgactggga aaaccctggc gttacccaac ttaatcgcct tgcagcacat ccccctttcg   1560
ccagctggcg taatagcgaa gaggcccgca ccgatcgccc ttcccaacag ttgcgcagcc   1620
tgaatggcga atggcgcttt gcctggtttc cggcaccaga agcggtgccg gaaagctggc   1680
tggagtgcga tcttcctgag gccgatactg tcgtcgtccc ctcaaactgg cagatgcacg   1740
gttacgatgc gcccatctac accaacgtga cctatcccat tacggtcaat ccgccgtttg   1800
ttcccacgga gaatccgacg ggttgttact cgctcacatt taatgttgat gaaagctggc   1860
tacaggaagg ccagacgcga attatttttg atggcgtcgg gatctgatcc ggatttacta   1920
actggaagag gcactaa                                                 1937
```

<210> SEQ ID NO 7
<211> LENGTH: 2652
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: T7 RNA polymerase gene

<400> SEQUENCE: 7

```
atgaacacga ttaacatcgc taagaacgac ttctctgaca tcgaactggc tgctatcccg     60
ttcaacactc tggctgacca ttacggtgag cgtttagctc gcgaacagtt ggcccttgag    120
catgagtctt acgagatggg tgaagcacgc ttccgcaaga tgtttgagcg tcaacttaaa    180
gctggtgagg ttgcggataa cgctgccgcc aagcctctca tcactaccct actccctaag    240
atgattgcac gcatcaacga ctggtttgag gaagtgaaag ctaagcgcgg caagcgcccg    300
acagccttcc agttcctgca agaaatcaag ccggaagccg tagcgtacat caccattaag    360
accactctgg cttgcctaac cagtgctgac aatacaaccg ttcaggctgt agcaagcgca    420
atcggtcggg ccattgagga cgaggctcgc ttcggtcgta tccgtgacct tgaagctaag    480
cacttcaaga aaaacgttga ggaacaactc aacaagcgcg tagggcacgt ctacaagaaa    540
gcatttatgc aagttgtcga ggctgacatg ctctctaagg gtctactcgg tggcgaggcg    600
tggtcttcgt ggcataagga agactctatt catgtaggag tacgctgcat cgagatgctc    660
```

| | |
|---|---|
| attgagtcaa ccggaatggt tagcttacac cgccaaaatg ctggcgtagt aggtcaagac | 720 |
| tctgagacta tcgaactcgc acctgaatac gctgaggcta tcgcaacccg tgcaggtgcg | 780 |
| ctggctggca tctctccgat gttccaacct tgcgtagttc ctcctaagcc gtggactggc | 840 |
| attactggtg gtggctattg ggctaacggt cgtcgtcctc tggcgctggt gcgtactcac | 900 |
| agtaagaaag cactgatgcg ctacgaagac gtttacatgc ctgaggtgta caaagcgatt | 960 |
| aacattgcgc aaaacaccgc atggaaaatc aacaagaaag tcctagcggt cgccaacgta | 1020 |
| atcaccaagt ggaagcattg tccggtcgag gacatccctg cgattgagcg tgaagaactc | 1080 |
| ccgatgaaac cggaagacat cgacatgaat cctgaggctc tcaccgcgtg gaaacgtgct | 1140 |
| gccgctgctg tgtaccgcaa ggacaaggct cgcaagtctc gccgtatcag ccttgagttc | 1200 |
| atgcttgagc aagccaataa gtttgctaac cataaggcca tctggttccc ttacaacatg | 1260 |
| gactggcgcg tcgtgtttta cgctgtgtca atgttcaacc cgcaaggtaa cgatatgacc | 1320 |
| aaaggactgc ttacgctggc gaaaggtaaa ccaatcggta aggaaggtta ctactggctg | 1380 |
| aaaatccacg gtgcaaactg tgcgggtgtc gataaggttc cgttccctga gcgcatcaag | 1440 |
| ttcattgagg aaaaccacga gaacatcatg gcttgcgcta gtctccact ggagaacact | 1500 |
| tggtgggctg agcaagattc tccgttctgc ttccttgcgt tctgctttga gtacgctggg | 1560 |
| gtacagcacc acggcctgag ctataactgc tcccttccgc tggcgtttga cgggtcttgc | 1620 |
| tctggcatcc agcacttctc cgcgatgctc cgagatgagg taggtggtcg cgcggttaac | 1680 |
| ttgcttccta gtgaaaccgt tcaggacatc tacgggattg ttgctaagaa agtcaacgag | 1740 |
| attctacaag cagacgcaat caatgggacc gataacgaag tagttaccgt gaccgatgag | 1800 |
| aacactggtg aaatctctga gaaagtcaag ctgggcacta aggcactggc tggtcaatgg | 1860 |
| ctggcttacg gtgttactcg cagtgtgact aagcgttcag tcatgacgct ggcttacggg | 1920 |
| tccaaagagt tcggcttccg tcaacaagtg ctggaagata ccattcagcc agctattgat | 1980 |
| tccggcaagg gtctgatgtt cactcagccg aatcaggctg ctggatacat ggctaagctg | 2040 |
| atttgggaat ctgtgagcgt gacggtggta gctgcggttg aagcaatgaa ctggcttaag | 2100 |
| tctgctgcta gctgctggc tgctgaggtc aaagataaga agactggaga gattcttcgc | 2160 |
| aagcgttgcg ctgtgcattg ggtaactcct gatggtttcc ctgtgtggca ggaatacaag | 2220 |
| aagcctattc agacgcgctt gaacctgatg ttcctcggtc agttccgctt acagcctacc | 2280 |
| attaacacca acaaagatag cgagattgat gcacacaaac aggagtctgg tatcgctcct | 2340 |
| aactttgtac acagccaaga cggtagccac cttcgtaaga ctgtagtgtg gcacacgag | 2400 |
| aagtacggaa tcgaatcttt tgcactgatt cacgactcct tcggtaccat tccggctgac | 2460 |
| gctgcgaacc tgttcaaagc agtgcgcgaa actatggttg acacatatga gtcttgtgat | 2520 |
| gtactggctg atttctacga ccagttcgct gaccagttgc acgagtctca attggacaaa | 2580 |
| atgccagcac ttccggctaa aggtaacttg aacctccgtg acatcttaga gtcggacttc | 2640 |
| gcgttcgcgt aa | 2652 |

<210> SEQ ID NO 8
<211> LENGTH: 34
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: ribosome binding site, weak -continued

```
<400> SEQUENCE: 8
tatccaaacc agtagctcaa ttggagtcgt ctat                                  34

<210> SEQ ID NO 9
<211> LENGTH: 37
<212> TYPE: PRT
<213> ORGANISM: Vibrio natriegens
<220> FEATURE:
<221> NAME/KEY: misc_feature
<223> OTHER INFORMATION: Signal sequence

<400> SEQUENCE: 9

Met Arg Ile Leu Leu Thr Glu Val Ser Lys Met Arg Ser Thr Lys Met
1               5                   10                  15

Lys Ala Gly Val Pro Ile Leu Gly Ile Leu Met Gly Thr Ala Ala Ser
            20                  25                  30

Gln Leu Ala Phe Ala
        35

<210> SEQ ID NO 10
<211> LENGTH: 25
<212> TYPE: PRT
<213> ORGANISM: Vibrio natriegens
<220> FEATURE:
<221> NAME/KEY: misc_feature
<223> OTHER INFORMATION: Signal sequence

<400> SEQUENCE: 10

Met Gln Met Lys Thr Met Lys Ser Lys Leu Ala Val Ala Leu Ile Ala
1               5                   10                  15

Ala Gly Leu Ser Phe Asn Ser Leu Ala
            20                  25

<210> SEQ ID NO 11
<211> LENGTH: 50
<212> TYPE: PRT
<213> ORGANISM: Vibrio natriegens
<220> FEATURE:
<221> NAME/KEY: misc_feature
<223> OTHER INFORMATION: Signal sequence

<400> SEQUENCE: 11

Met Arg Asn Asn Gln Leu Thr Leu Ala Leu Lys Lys Ile Lys Lys Gly
1               5                   10                  15

Ile Arg Lys Gly Tyr Pro Lys Leu Arg Lys Gly Ser Gly Leu Ile Met
            20                  25                  30

Lys Lys Thr Leu Leu Ala Leu Ala Val Ala Thr Val Ser Thr Ser Ala
        35                  40                  45

Leu Ala
    50

<210> SEQ ID NO 12
<211> LENGTH: 22
<212> TYPE: PRT
<213> ORGANISM: Vibrio natriegens
<220> FEATURE:
<221> NAME/KEY: misc_feature
<223> OTHER INFORMATION: Signal sequence

<400> SEQUENCE: 12

Met Lys Lys Leu Ser Ala Val Ala Leu Gly Thr Leu Val Ala Leu Gly
1               5                   10                  15

Ser Phe Gly Ala His Ala
```

20

<210> SEQ ID NO 13
<211> LENGTH: 26
<212> TYPE: PRT
<213> ORGANISM: Vibrio natriegens
<220> FEATURE:
<221> NAME/KEY: misc_feature
<223> OTHER INFORMATION: Signal sequence

<400> SEQUENCE: 13

Met Glu Leu Arg Met Lys Lys Val Ser Val Ile Ala Ala Ala Val Ala
1               5                   10                  15

Ala Ser Leu Ala Ala Gly Ser Ala Phe Ala
            20                  25

<210> SEQ ID NO 14
<211> LENGTH: 21
<212> TYPE: PRT
<213> ORGANISM: Vibrio natriegens
<220> FEATURE:
<221> NAME/KEY: misc_feature
<223> OTHER INFORMATION: Signal sequence

<400> SEQUENCE: 14

Met Lys Lys Thr Leu Ile Ala Leu Ser Val Ser Ala Ala Ala Met Ala
1               5                   10                  15

Thr Gly Val Asn Ala
            20

<210> SEQ ID NO 15
<211> LENGTH: 32
<212> TYPE: PRT
<213> ORGANISM: Vibrio natriegens
<220> FEATURE:
<221> NAME/KEY: misc_feature
<223> OTHER INFORMATION: Signal sequence

<400> SEQUENCE: 15

Met Gln Ser Ile Gln Gly Asn Ile Met Asn Lys Val Ala Ile Ala Val
1               5                   10                  15

Ala Ala Val Val Ala Gly Gly Ser Ala Leu Leu Asn Thr Ala Gln Ala
            20                  25                  30

<210> SEQ ID NO 16
<211> LENGTH: 24
<212> TYPE: PRT
<213> ORGANISM: Vibrio natriegens
<220> FEATURE:
<221> NAME/KEY: misc_feature
<223> OTHER INFORMATION: Signal sequence

<400> SEQUENCE: 16

Met Ala Phe Asn Lys Leu Leu Lys Val Gly Ala Ile Ala Ala Ala Val
1               5                   10                  15

Met Gly Ala Gly Ala Val Asn Ala
            20

<210> SEQ ID NO 17
<211> LENGTH: 26
<212> TYPE: PRT
<213> ORGANISM: Vibrio natriegens
<220> FEATURE:
<221> NAME/KEY: misc_feature
<223> OTHER INFORMATION: Signal sequence

```
<400> SEQUENCE: 17

Met Lys Lys Pro Leu Leu Ala Leu Thr Val Leu Ser Leu Ser Leu Ser
1               5                   10                  15

Ser Ile Phe Thr Pro Ile Gln Ala Thr Ala
            20                  25

<210> SEQ ID NO 18
<211> LENGTH: 21
<212> TYPE: PRT
<213> ORGANISM: Vibrio natriegens
<220> FEATURE:
<221> NAME/KEY: misc_feature
<223> OTHER INFORMATION: Signal sequence

<400> SEQUENCE: 18

Met Lys Lys Val Leu Thr Leu Ser Ala Leu Ala Cys Ala Thr Leu Ala
1               5                   10                  15

Pro Thr Ala Met Ala
            20

<210> SEQ ID NO 19
<211> LENGTH: 21
<212> TYPE: PRT
<213> ORGANISM: Vibrio natriegens
<220> FEATURE:
<221> NAME/KEY: misc_feature
<223> OTHER INFORMATION: Signal sequence

<400> SEQUENCE: 19

Met Lys Lys Trp Leu Leu Ala Ala Thr Leu Ala Ala Thr Ala Val Ser
1               5                   10                  15

Gly Ala Val Gln Ala
            20

<210> SEQ ID NO 20
<211> LENGTH: 22
<212> TYPE: PRT
<213> ORGANISM: Vibrio natriegens
<220> FEATURE:
<221> NAME/KEY: misc_feature
<223> OTHER INFORMATION: Signal sequence

<400> SEQUENCE: 20

Met Met Lys Asn Trp Ile Lys Val Ala Val Ala Ala Ile Ala Leu Ser
1               5                   10                  15

Ala Ala Thr Val Gln Ala
            20

<210> SEQ ID NO 21
<211> LENGTH: 29
<212> TYPE: PRT
<213> ORGANISM: Vibrio natriegens
<220> FEATURE:
<221> NAME/KEY: misc_feature
<223> OTHER INFORMATION: Signal sequence

<400> SEQUENCE: 21

Met Asn Thr Gln Val Lys Lys Pro Ser Phe Met Pro Ser Ile Leu Ala
1               5                   10                  15

Ala Ala Val Val Thr Ala Phe Ser Gly Gln Ala Asn Ala
            20                  25

<210> SEQ ID NO 22
<211> LENGTH: 20
```

```
<212> TYPE: PRT
<213> ORGANISM: Vibrio natriegens
<220> FEATURE:
<221> NAME/KEY: misc_feature
<223> OTHER INFORMATION: Signal sequence

<400> SEQUENCE: 22

Met Lys Lys Leu Ala Ala Val Ile Ser Ala Ser Leu Leu Met Ala Ser
1               5                   10                  15

Ala Ala Gln Ala
            20

<210> SEQ ID NO 23
<211> LENGTH: 24
<212> TYPE: PRT
<213> ORGANISM: Vibrio natriegens
<220> FEATURE:
<221> NAME/KEY: misc_feature
<223> OTHER INFORMATION: Signal sequence

<400> SEQUENCE: 23

Met Asn Cys Ser His Lys Phe Lys Leu Thr Ala Ile Ala Met Met Val
1               5                   10                  15

Gly Ser Ser Met Ser Ala Asn Ala
            20

<210> SEQ ID NO 24
<211> LENGTH: 25
<212> TYPE: PRT
<213> ORGANISM: Vibrio natriegens
<220> FEATURE:
<221> NAME/KEY: misc_feature
<223> OTHER INFORMATION: Signal sequence

<400> SEQUENCE: 24

Met Asn Lys Leu Leu Thr Leu Thr Pro Leu Ala Val Ala Ile Gly Ser
1               5                   10                  15

Ser Leu Val Val Pro Ser Ala Val Ala
            20                  25

<210> SEQ ID NO 25
<211> LENGTH: 21
<212> TYPE: PRT
<213> ORGANISM: Vibrio natriegens
<220> FEATURE:
<221> NAME/KEY: misc_feature
<223> OTHER INFORMATION: Signal sequence

<400> SEQUENCE: 25

Met Lys Lys Thr Ile Cys Ser Leu Ala Val Val Ala Ala Leu Val Ser
1               5                   10                  15

Pro Ser Val Phe Ala
            20
```

GENETICALLY ENGINEERED *VIBRIO* SP. AND USES THEREOF

CROSS-REFERENCE TO RELATED APPLICATIONS

This application is a divisional application of U.S. application Ser. No. 15/367,106 filed Dec. 1, 2016, now issued as U.S. Pat. No. 10,377,997; which claims the benefit under 35 USC § 119(e) to U.S. Application Ser. No. 62/261,758 filed Dec. 1, 2015. The disclosure of each of the prior applications is considered part of and is incorporated by reference in the disclosure of this application.

INCORPORATION BY REFERENCE OF SEQUENCE LISTING

The material in the accompanying sequence listing is hereby incorporated by reference into the application. The accompanying sequence listing text file, named DNASGI1910-2_ST25.txt, was created on Jul. 26, 2019 and is 42 KB in size. The file can be accessed using Microsoft Word on a computer that uses Window OS.

BACKGROUND OF THE INVENTION

Field of the Invention

The present disclosure relates generally to genetically engineered *Vibrio* sp. bacteria and the use of such bacteria for the construction, maintenance, manipulation, and/or propagation of recombinant DNA, and protein expression.

Background Information

The biotechnology sector relies upon organisms such as *E. coli* as hosts for the generation of desired biomolecules (e.g., recombinant DNA, proteins, natural products, etc.) as well as for the study of biological processes and the development of bio-based technologies and products. While advances in fields such as genomics, synthetic biology, and genome/metabolic engineering have made possible projects at an unprecedented scale, the host organisms that the field relies upon have changed relatively little in decades and are proving to be inadequate or inefficient for many ambitious projects.

*E. coli* has been the main prokaryotic workhorse for several decades, being used ubiquitously in both academic and industrial efforts, and relied upon as a host for molecular cloning, protein expression, metabolic engineering, a source of cellular extracts for in vitro molecular biology, and as a chassis for synthetic biology efforts. The use of *E. coli* is due largely to its extensive characterization (having served as a model organism since the late 19th century), having a large collection of standardized tools and protocols, and being relatively easy to work with. *E. coli* is certainly not the only organism in use in biotechnology, as there are plenty of obscure organisms being utilized, usually to leverage some peculiar biological property that allows that organism to excel in some niche application, but *E. coli* is hands down the most widely adopted and broadly applied bacterial species in biotechnology.

There is a need for robust, faster growing, and easily genetically manipulated bacterial cells that can be used as host organisms, especially to produce products such as large recombinant DNA molecules, and as alternative hosts for protein and peptide expression.

SUMMARY OF THE INVENTION

The present disclosure relates to the generation of genetically engineered *Vibrio* sp. bacteria. Specifically, the disclosure relates to the use of the genetically engineered bacteria for the construction, maintenance, manipulation, and/or propagation of DNA constructs; protein expression; metabolic engineering; expression of cellular extracts for cell-free biology; and for synthetic biology applications. The disclosure also relates to the use of the replication machinery of *Vibrio* sp. on a cloning vector for replication of recombinant DNA constructs.

In some aspects, the present disclosure provides a genetically engineered *Vibrio* sp. bacteria comprising an altered Chromosome I or Chromosome II. In some examples, one or more non-essential genes are removed from either Chromosome I or Chromosome II. In some examples, the one or more removed genes encode an element selected from the group consisting of an endonuclease, an exonuclease, a methylase, a nuclease, a restriction enzyme, and a restriction-modification system.

In some aspects, the present disclosure provides a genetically engineered *Vibrio* sp. bacteria, wherein at least one essential element from Chromosome II is alternatively located on an engineered Chromosome I. In some examples, the essential element is a gene required for a function selected from the group consisting of metabolism, DNA replication, transcription, translation, cellular structure maintenance, and transport processes into or out of the cell.

In some aspects, the present disclosure provides a genetically engineered *Vibrio* sp. bacteria that contains only one chromosome. In some examples, the single chromosome comprises essential elements from Chromosome I and Chromosome II such that the single chromosome is capable of supporting survival and replication of the bacteria under non-selective conditions.

In some aspects, the herein disclosed genetically engineered *Vibrio* sp. further comprises a heterologous nucleic acid sequence operably linked to a heterologous promoter. In some examples the heterologous nucleic acid encodes T7 RNA polymerase. In some examples, the heterologous promoter is an inducible promoter.

In some aspects, the present disclosure provides a process for producing competent *Vibrio* sp. cells comprising: (a) growing *Vibrio* sp. cells in a growth-conducive medium; (b) rendering said *Vibrio* sp. cells competent; and (c) freezing the cells. In some examples, the *Vibrio* sp. bacterial cells are any of those disclosed herein. In some examples, rendering the cells competent comprises growing the cells in a solution with supplemented salts.

In some aspects, the present disclosure provides a method of producing a biomolecule comprising: a) contacting *Vibrio* sp. bacteria with a heterologous nucleic acid encoding the biomolecule, such that the heterologous nucleic acid is introduced into the bacteria; b) growing the bacteria in a growth-conducive medium wherein the heterologous nucleic acid is expressed, thereby producing the biomolecule; and c) isolating the biomolecule. In some examples, the method is performed using any of the bacteria disclosed herein. In some examples, the heterologous nucleic acid comprises a nucleic acid sequence encoding *Vibrio* sp. replication machinery. In some examples, the replication machinery comprises SEQ ID NO: 1. In some examples, the heterologous nucleic acid further comprises an inducible promoter operably linked to the nucleic acid encoding the biomolecule. In some examples, the *Vibrio* sp. bacteria are naturally competent. In some examples, the *Vibrio* sp. bacteria are competent cells generated by any of the methods disclosed herein. In some examples, the nucleic acid is introduced by conjugation, chemical competence, natural competence, or electroporation. In some examples, the herein disclosed method further comprises monitoring the growth conducive media for the presence of the biomolecule over time.

In some aspects, the present disclosure provides an isolated or synthesized nucleic acid molecule comprising SEQ ID NO:1. In some examples, the isolated or synthesized nucleic acid molecule further comprises heterologous sequence on the 5' and 3' end, wherein the heterologous 5' and 3' sequences are compatible for cloning into a target vector.

In some aspects, the present disclosure provides a vector comprising *Vibrio* sp. chromosomal replication machinery. In some examples, the replication machinery comprises SEQ ID NO: 1. In some examples, the vector further comprises a heterologous nucleic acid of interest. In some examples, the vector further comprises an inducible promoter operably linked to a nucleic acid of interest. In some examples, the vector is capable of replication in *E. coli* or *S. cerevisiae*.

In some aspects, the present disclosure provides a composition comprising any of the genetically engineered *Vibrio* sp. disclosed herein. In some examples, the genetically engineered *Vibrio* sp. bacteria disclosed herein are naturally competent. In some examples, the genetically engineered *Vibrio* sp. bacteria are competent cells generated by any of the methods disclosed herein. In some examples, the competent genetically engineered *V. natriegens* bacteria are generated by the process of: (a) growing genetically modified *V. natriegens* bacterial cells in a growth-conducive medium; (b) rendering said *V. natriegens* bacterial cells competent; and (c) freezing the cells.

In some aspects, the present disclosure provides an expression system which comprises a vector comprising the *Vibrio* sp. chromosomal replication machinery. In some examples, the replication machinery comprises SEQ ID NO: 1. In some examples, the vector further comprises a heterologous nucleic acid of interest. In some examples, the vector further comprises an inducible promoter operably linked to a nucleic acid of interest. In some examples, the vector is capable of replication in *E. coli* or *S. cerevisiae*.

In some aspects, the present disclosure provides host cells comprising a vector comprising *Vibrio* sp. chromosomal replication machinery. In some examples, the host cells are naturally competent. In some examples, the host cells are competent cells generated by any of the herein disclosed methods. In some examples, the vector is introduced into the host cell by conjugation, chemical competence, natural competence, or electroporation. In some examples, the replication machinery comprises SEQ ID NO: 1. In some examples, the vector further comprises a heterologous nucleic acid of interest. In some examples, the vector further comprises an inducible promoter operably linked to a nucleic acid of interest. In some examples, the host cells are any engineered *Vibrio* sp. bacteria disclosed herein.

In some aspects, the present disclosure provides a method of producing a polypeptide comprising: a) culturing cells comprising a vector comprising a *Vibrio* sp. chromosomal replication machinery and a nucleic acid encoding the polypeptide under conditions effective for the production of the polypeptide; and b) harvesting the polypeptide. In some examples, the replication machinery comprises SEQ ID NO: 1. In some examples, the vector further comprises an inducible promoter operably linked to a nucleic acid encoding the polypeptide. In some examples, the vector is capable of replication in *E. coli* or *S. cerevisiae*. In some examples, the cultured cells are *Vibrio* sp. bacterial cells. In some examples, the *Vibrio* sp. cells are any of those disclosed herein. In some examples the cultured cells or *Vibrio* sp. cells are naturally competent. In some examples, the cultured cells or *Vibrio* sp. cells are competent cells generated by any of the methods disclosed herein. In some examples, the vector is introduced into the cultured cells or *Vibrio* sp. cells by conjugation, chemical competence, natural competence, or electroporation.

In some aspects, the present disclosure provides a method of producing a polypeptide comprising: a) contacting *Vibrio* sp. bacteria with a vector comprising a nucleic acid encoding the polypeptide and an inducible promoter, such that the vector is introduced into the bacteria; b) growing the bacteria under conditions effective for production of the polypeptide; and c) harvesting the polypeptide. In some examples, the vector comprises *Vibrio* sp. chromosomal replication machinery. In some examples, the replication machinery comprises SEQ ID NO: 1. In some examples, the vector is capable of replication in *E. coli* or *S. cerevisiae*. In some examples, the *Vibrio* sp. cells are any of those disclosed herein. In some examples, the *Vibrio* sp. bacteria are naturally competent. In some examples the *Vibrio* sp. bacteria are competent cells generated by any of the methods disclosed herein. In some examples, the vector is introduced into the *Vibrio* sp. bacteria by conjugation, chemical competence, natural competence, or electroporation.

In some aspects, the present disclosure provides a method for cloning a nucleic acid comprising: a) introducing a heterologous nucleic acid into *Vibrio* sp. bacteria to create a transformed bacteria; b) culturing the cells under conditions for growth of the cells; c) isolation of a single transformed bacterial colony; d) growth of the bacterial colony; and e) extraction of nucleic acid. In some examples, the *Vibrio* sp. bacteria are those of any of those disclosed herein. In some examples the *Vibrio* sp. bacteria are naturally competent. In some examples, the *Vibrio* sp. bacteria are competent cells generated by any of the methods disclosed herein. In some examples, the introduction of the nucleic acid is performed by conjugation, chemical competence, natural competence, or electroporation. In some examples, the heterologous nucleic acid is a vector. In some examples, the vector comprises *Vibrio* sp. chromosomal replication machinery. In some examples, the replication machinery comprises SEQ ID NO: 1. In some examples, the vector is capable of replication in *E. coli* or *S. cerevisiae*.

In some aspects, the present disclosure provides a kit for cloning DNA comprising: a) a vector comprising the *Vibrio* sp. chromosomal replication machinery; b) host cells compatible with the vector; c) buffer compatible with the host cells; and d) instructions for cloning the DNA. In some examples, the vector further comprises an inducible promoter. In some examples, the replication machinery comprises SEQ ID NO: 1. In some examples, the host cells are *Vibrio* sp. bacteria. In some examples the *Vibrio* sp. bacteria are any of those disclosed herein. In some examples, the host cells are *E. coli* or *S. cerevisiae*.

In some aspects, the present disclosure provides a kit comprising competent *Vibrio* sp. bacterial cells. In some examples the *Vibrio* sp. bacterial cells are any of those disclosed herein. In some examples, the kit further comprises a compatible cloning vector.

BRIEF DESCRIPTION OF THE DRAWINGS

FIG. 1A. pBR322-trc-GFP; FIG. 1B. p15a-trc-GFP; FIG. 1C. pBR322-araBAD-GFP; FIG. 1D. p15a-araBAD-GFP; FIG. 1E. pBR322-cI857ts-GFP and FIG. 1F. p15a-cI857ts-GFP.

FIG. 8A) White light image of cultures. Two left most cultures are wild type strains not expressing GFP, while the other four cultures have a distinct yellow/green color, indicating expression of GFP. FIG. 8B) Blue light transilluminator image displaying the positive expression of GFP in the right four cultures, while the two wild type cultures on the left are not expressing GFP and therefore lack the trademark green fluorescent color.

DETAILED DESCRIPTION OF THE INVENTION

Figure 1A:
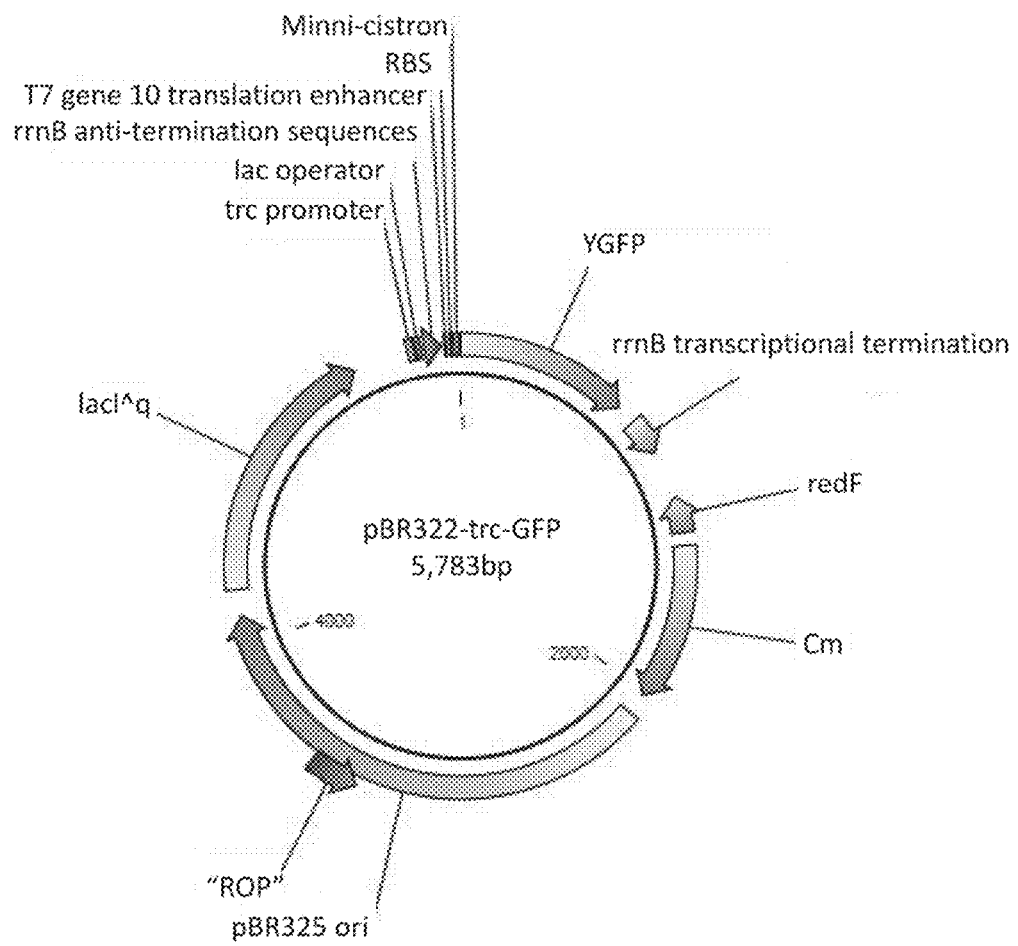
FIGS. 1A-1F show the use of *V. natriegens* as a host for inducible protein expression. Six plasmids were designed for inducible protein expression of GFP.
Figure 1B:
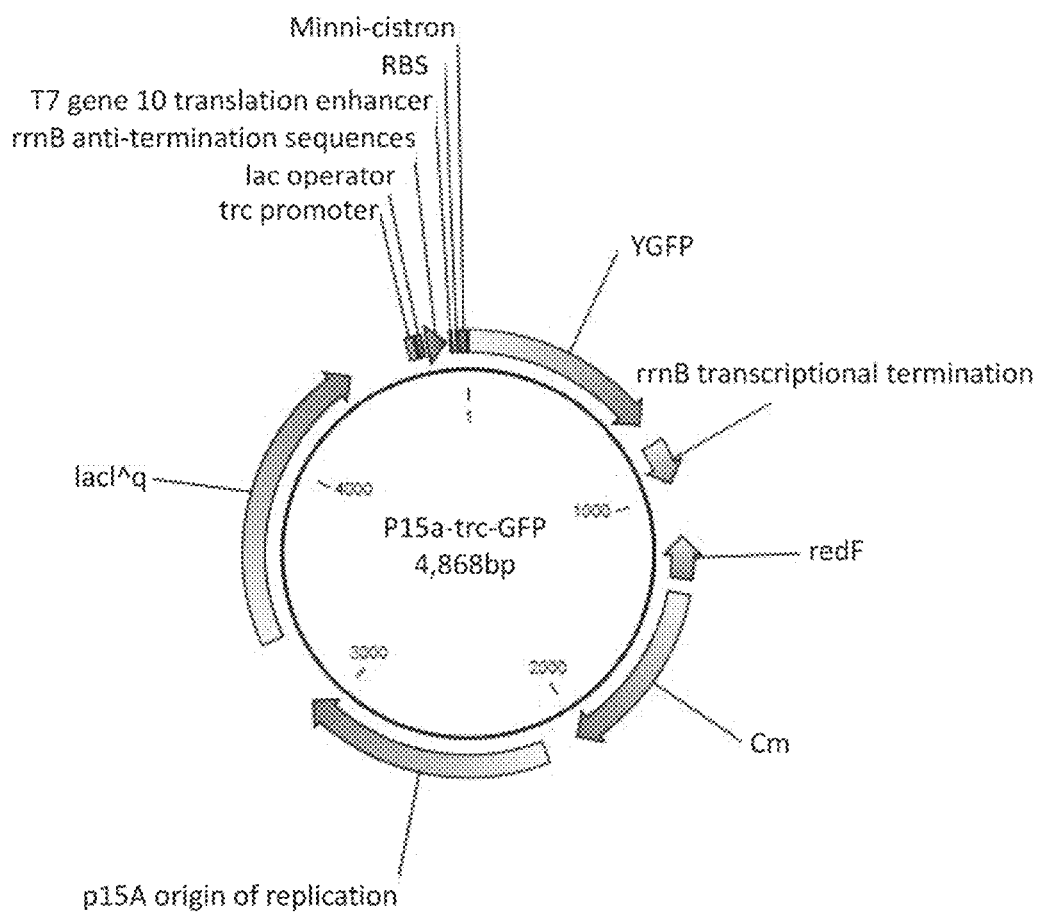
Figure 1C:
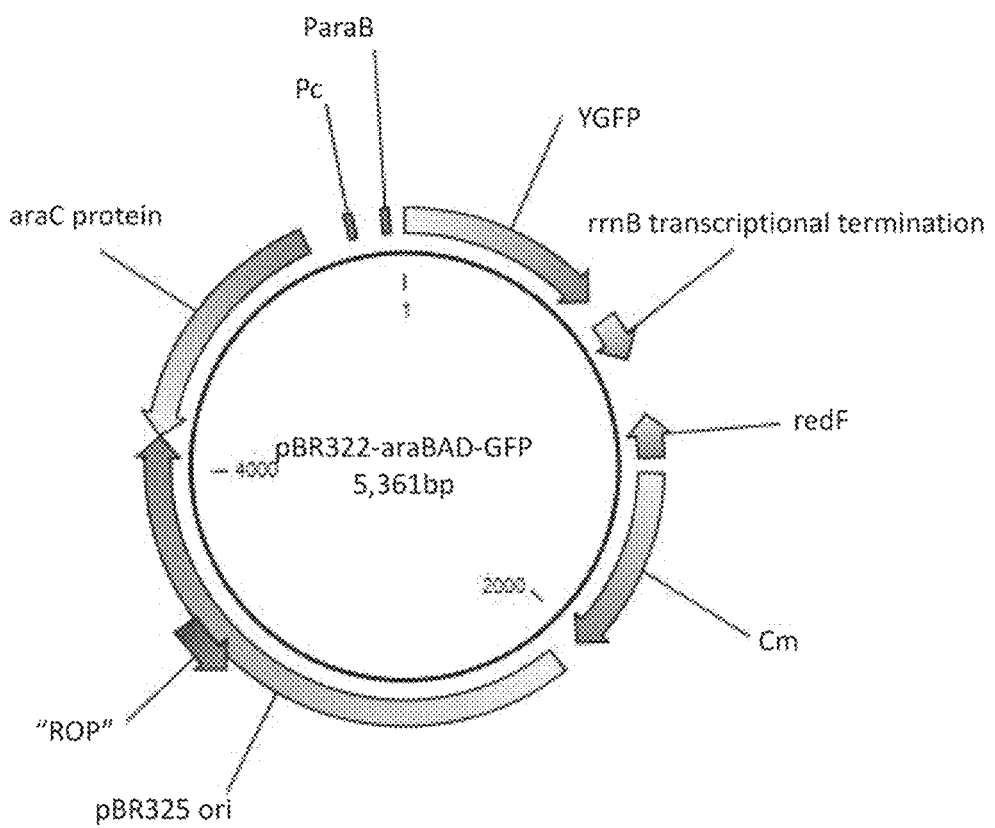
Figure 1D:
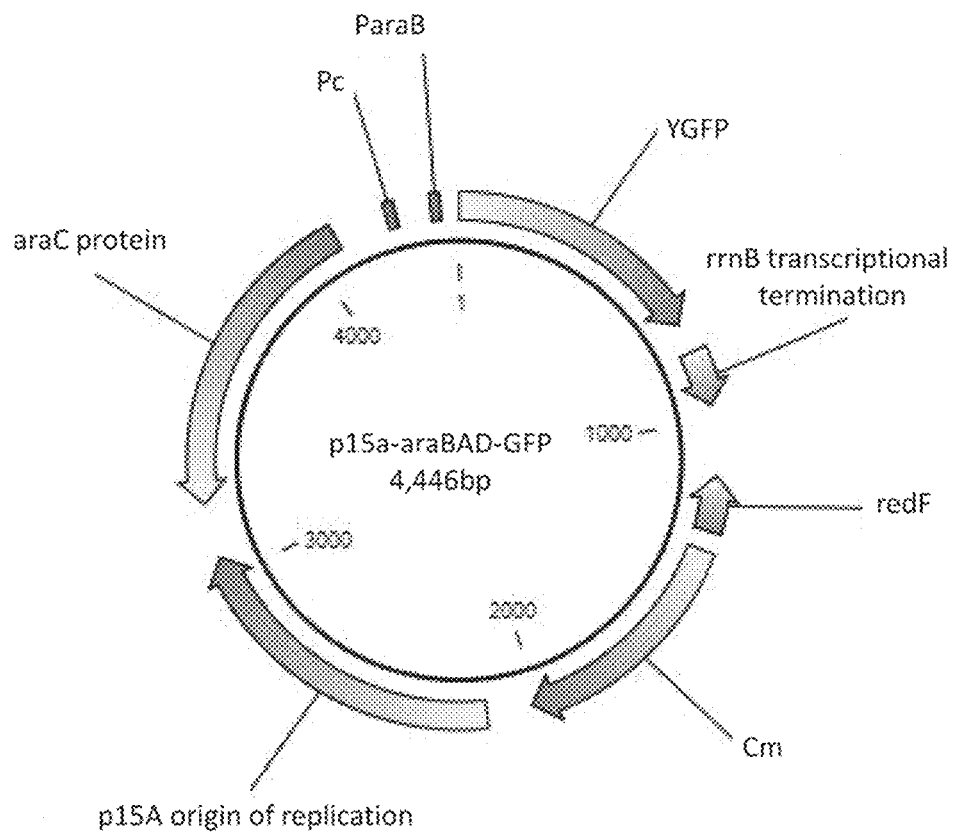
Figure 1E:
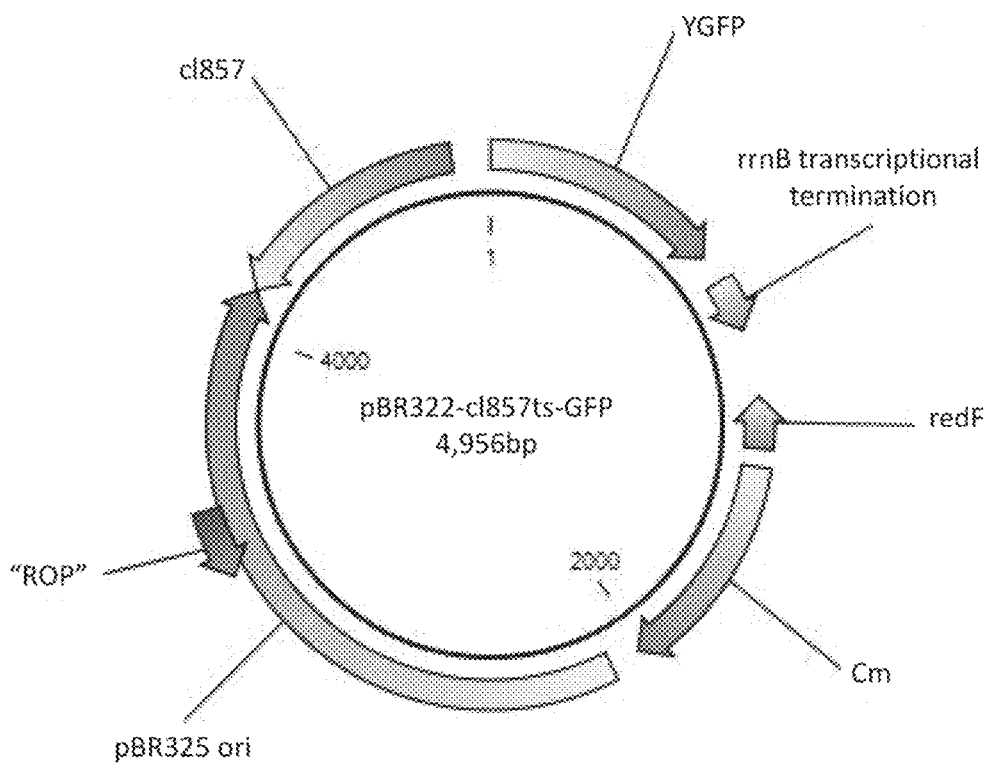
Figure 1F:
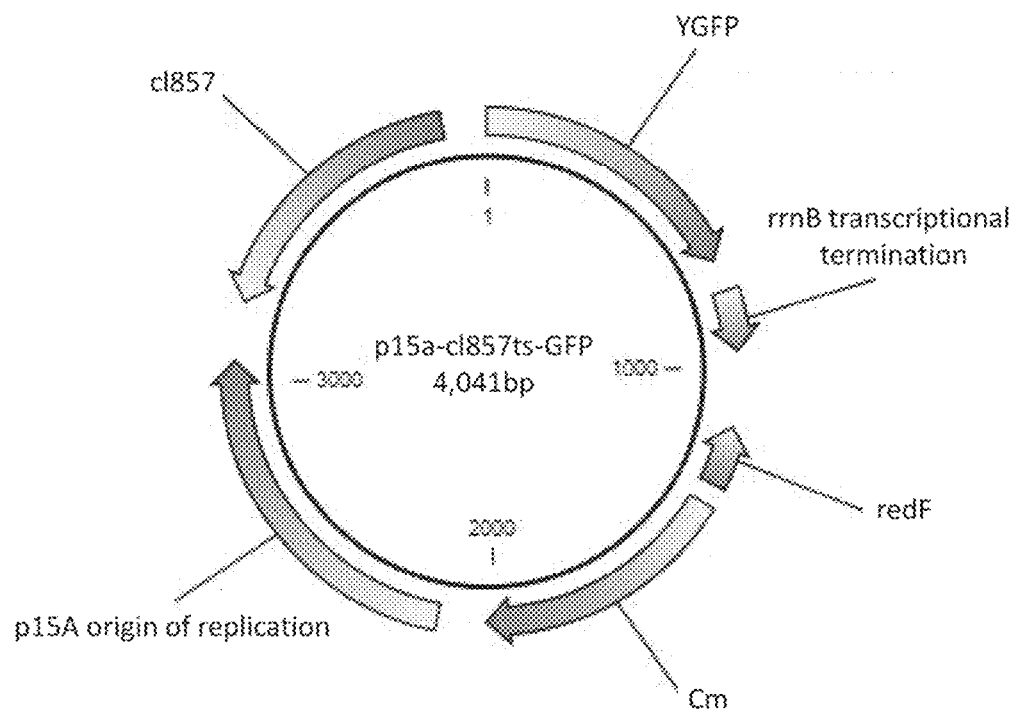

The present disclosure relates to the generation of a genetically engineered *Vibrio* sp. bacteria. Specifically, the disclosure relates to the use of the genetically engineered bacteria for the construction, maintenance, manipulation, and/or propagation of DNA constructs; protein expression; metabolic engineering; expression of cellular extracts for cell-free biology; and for synthetic biology applications. The disclosure also relates to the use of the replication machinery of *Vibrio* sp. on a cloning vector for replication of recombinant DNA constructs.

Herein is described the use of the organism *Vibrio natriegens* as a novel host for biotechnological applications, particularly as a host for the construction, maintenance, manipulation, and/or propagation of recombinant DNA constructs (including synthetic or semi-synthetic DNA constructs); for protein expression; for metabolic engineering; for the preparation of cellular extracts for cell-free biology (e.g., cell-free protein synthesis, in vitro enzymatic catalysis, DNA replication, and RNA transcription); and as a chassis for synthetic biology applications. Furthermore, the replication machinery of the smaller, second chromosome of *V. natriegens* can be used as a novel cloning vector for replication of recombinant DNA constructs including complete or partial exogenous chromosomes (synthetic or natural) in either *V. natriegens* or a different host such as *E. coli*, as well as using bacterial conjugation as a means to deliver this vector from another host into V *natriegens* or from *V. natriegens* to the final host organism. Applications related to molecular biology, synthetic biology, and metabolic engineering will be accelerated using the *V. natriegens* host due to its rapid growth rate and nutritional versatility.

Before the present compositions and methods are described, it is to be understood that this disclosure is not limited to particular compositions, methods, and experimental conditions described, as such compositions, methods, and conditions may vary. It is also to be understood that the terminology used herein is for purposes of describing particular embodiments only, and is not intended to be limiting, since the scope of the present disclosure will be limited only in the appended claims.

Unless defined otherwise, all technical and scientific terms used herein have the same meaning as commonly understood by one of ordinary skill in the art to which this disclosure belongs. Although any methods and materials similar or equivalent to those described herein can be used in the practice or testing of the disclosure, the preferred methods and materials are now described. The definitions set forth below are for understanding of the disclosure but shall in no way be considered to supplant the understanding of the terms held by those of ordinary skill in the art.

As used in this specification and the appended claims, the singular forms "a", "an", and "the" include plural references unless the context clearly dictates otherwise. Thus, for example, references to "the method" includes one or more methods, and/or steps of the type described herein which will become apparent to those persons skilled in the art upon reading this disclosure and so forth.

As used herein, "about" means either: within plus or minus 10% of the provided value, or a value rounded to the nearest significant figure, in all cases inclusive of the provided value. Where ranges are provided, they are inclusive of the boundary values.

As used herein, "amino acid" refers to naturally-occurring and synthetic amino acids, as well as amino acid analogs and amino acid mimetics that function in a manner similar to the naturally-occurring amino acids. Naturally-occurring amino acids are those encoded by the genetic code, including D/L optical isomers, as well as those amino acids that are later modified, e.g., hydroxyproline, γ-carboxyglutamate, and O-phosphoserine. Amino acid analogs refer to compounds that have the same basic chemical structure as a naturally-occurring amino acid, i.e., a carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally-occurring amino acid. Amino acid mimetics, as used herein, refer to chemical compounds that have a structure that is different from the general chemical structure of an amino acid, but that functions in a manner similar to a naturally-occurring amino acid.

A "nucleotide" is the basic unit of a nucleic acid molecule and typically includes a base such as adenine, guanine, cytosine, thymine, or uracil linked to a pentose sugar such as ribose or deoxyribose that is in turn linked to a phosphate group. Nucleotides can also include alternative or non-naturally occurring bases or sugars that do not occur in naturally-occurring DNA or RNA. In peptide nucleic acids one or more sugars may be substituted by amino acids, and in some nucleic acid analogs at least a portion of the phosphates may be replaced by hydroxyl groups. Although nucleotides are often used to denote the length of a single-stranded nucleic acid molecule, and "base pairs" (i.e., base paired nucleotides) are often used to denote the length of double-stranded nucleic acid molecules, in the present application, "nucleotides" or "nt" may be used interchangeably with "base pairs" or "bp", and the use of one term or the other does not meant restrict the type of nucleic acid molecule being described to being either single-stranded or double-stranded. The use of kilobases (kb) or megabases (Mb) as units of length also applies equally to single-stranded and double-stranded nucleic acid molecules.

A "nucleic acid construct", "DNA construct" or simply "construct" is a nucleic acid molecule produced by recombinant means that includes at least two juxtaposed or operably linked nucleic acid sequences that are not juxtaposed or operably linked to one another in nature.

A "detectable marker" is a gene or the polypeptide encoded by the gene that confers some detectable phenotype on a cell that expresses the gene. Detection can be colorometric (for example, the blue color by expression of beta galactosidase or beta-glucuronidase in the presence of a colorometric substrate) or by detection of luminescence or fluorescence. A detectable marker generally encodes a detectable polypeptide, for example, a green fluorescent protein or a signal producing enzyme such as luciferase, which, when contacted with an appropriate agent (a particular, wavelength of light or luciferin, respectively) generates a signal that can be detected by eye or using appropriate instrumentation (Giacomin, *Plant Sci.* 116:59-72, 1996; Scikantha, *J. Bacteriol.* 178:121, 1996; Gerdes, *FEBS Lett.* 389:44-47, 1996; see, also, Jefferson, *EMBO J.* 6:3901-3907, 1997).

The term or "selectable marker" or "selection marker" refers to a gene (or the encoded polypeptide) that confers a phenotype that allows the organism expressing the gene to survive under selective conditions. For example, a selectable marker generally is a molecule that, when present or expressed in a cell, provides a selective advantage (or, if a negative selectable marker, disadvantage) to the cell containing the marker, for example, the ability to grow in the presence of an agent that otherwise would kill the cell, or the ability to grow in the absence of a particular nutrient. Selectable markers include, but are not limited to, an antibiotic resistance gene, a gene encoding a polypeptide conferring resistance to a toxin, an auxotrophic marker, and a combination thereof. An antibiotic resistance gene confers resistance to antibiotics including, but is not limited to, bleomycin, carbenicillin, chloramphenicol, gentamycin, glyphosate, hygromycin, kanamycin, neomycin, nourseothricin, phleomycin, puromycin, spectinomycin, streptomycin, and tetracycline.

A "cDNA" is a DNA molecule that comprises at least a portion the nucleotide sequence of an mRNA molecule, with the exception that the DNA molecule substitutes the nucleobase thymine, or T, in place of uridine, or U, occurring in the mRNA sequence. A cDNA can be single-stranded or double-stranded, and can be the complement of the mRNA sequence. In preferred embodiments, a cDNA does not include one or more intron sequences that occur in the naturally-occurring gene (in the genome of an organism) that the cDNA corresponds to. For example, a cDNA can have sequences from upstream (5') of an intron of a naturally-occurring gene juxtaposed to sequences downstream (3') of the intron of the naturally-occurring gene, where the upstream and downstream sequences are not juxtaposed in a DNA molecule (i.e., the naturally occurring gene) in nature. A cDNA can be produced by reverse transcription of mRNA molecules by a polymerase (e.g., a reverse transcriptase), or can be synthesized, for example, by chemical synthesis and/or by using one or more restriction enzymes, one or more ligases, one or more polymerases (including, but not limited to, high temperature tolerant polymerases that can be used in polymerase chain reactions (PCRs)), one or more recombinases, e.g., based on knowledge of the cDNA sequence, where the knowledge of the cDNA sequence can optionally be based on the identification of coding regions from genome sequences and/or the sequences of one or more cDNAs.

A "coding sequence" or "coding region", as used herein in reference to an mRNA or DNA molecule, refers to the portion of the mRNA or DNA molecule that codes for a polypeptide. It typically consists of the nucleotide residues of the molecule which are matched with an anticodon region of a transfer RNA molecule during translation of the mRNA molecule or which encode a stop codon. The coding sequence may include nucleotide residues corresponding to amino acid residues which are not present in the mature protein encoded by the mRNA molecule (e.g., amino acid residues in a protein export signal sequence).

"Compatible" or "compatible with", when referring to a vector or expression system in reference to a host, refers to the vector or expression system comprising the elements required for stable replication within the specified host cells. Optionally, "compatible" or "compatible with" can also refer to the vector or expression system having the elements and/or machinery required for one or more of the following functions: transformation, propagation, maintenance, selection, and recovery from the specified host organism or system. Such elements or machinery can comprise, but are not limited to, origins of replication, replication machinery, origins of transfer, transfer machinery, selectable marker, copy number induction elements, inducible promotor, and any other elements required for transformation, conjugation, propagation, maintenance, selection, or recovery, or any other standard scientific element or aspect.

"Competent", 'competence" or "competency" refers to the ability of a cell to take up extracellular DNA. Competence may be "natural competence", which is a genetically specified ability of bacteria which occurs under natural conditions as well as in the laboratory. Competence may alternatively be artificial or induced, which arises when cells in laboratory cultures are treated to make them transiently permeable to DNA.

"Derived from" refers to the source of a nucleotide or amino acid sequence, and typically means the sequence of the nucleic acid molecule, protein, or peptide is based on that of the referenced nucleic acid molecule, protein, or peptide. The nucleic acid molecule, protein, or peptide is either a variant having at least 60% identity or homology (and, in various examples, at least 65%, at least 70%, at least 75%, at least 80%, or at least 85% identity or homology) to the referenced nucleic acid molecule, protein, or peptide, and/or is a truncated or internally deleted variant of the referenced nucleic acid molecule, protein, or peptide. For example, a protein or peptide may be C-terminally or N-terminally truncated or internally deleted with respect to the protein or peptide it is derived from and may have a C-terminal, N-terminal, or internal deletion of any number of amino acids, for example, at least 1, 2, 3, 4, 5, 10, 20, 30, 40, 50, 60, 70, 80, 90, or 100 amino acids. A nucleic acid molecule may be 5' or 3' truncated or internally deleted with respect to the nucleic acid molecule it is derived from and may have a 5', 3', or internal deletion of any number of nucleotides, for example, at least 1, 2, 3, 4, 5, 10, 20, 30, 40, 50, 60, 70, 80, 90, 100, 150, or 200 nucleotides.

As used herein, the terms "percent identity" or "homology" with respect to nucleic acid or polypeptide sequences are defined as the percentage of nucleotide or amino acid residues in the candidate sequence that are identical with the known polypeptides, after aligning the sequences for maximum percent identity and introducing gaps, if necessary, to achieve the maximum percent homology. N-terminal or C-terminal insertion or deletions shall not be construed as affecting homology, and internal deletions and/or insertions into the polypeptide sequence of less than about 30, less than about 20, or less than about 10 amino acid residues shall not be construed as affecting homology. Homology or identity at the nucleotide or amino acid sequence level can be determined by BLAST (Basic Local Alignment Search Tool) analysis using the algorithm employed by the programs blastp, blastn, blastx, tblastn, and tblastx (Altschul (1997), *Nucleic Acids Res.* 25, 3389-3402, and Karlin (1990), *Proc. Natl. Acad. Sci. USA* 87, 2264-2268), which are tailored for sequence similarity searching. The approach used by the BLAST program is to first consider similar segments, with and without gaps, between a query sequence and a database sequence, then to evaluate the statistical significance of all matches that are identified, and finally to summarize only those matches which satisfy a preselected threshold of significance. For a discussion of basic issues in similarity searching of sequence databases, see Altschul (1994), *Nature Genetics* 6, 119-129. The search parameters for histogram, descriptions, alignments, expect (i.e., the statistical significance threshold for reporting matches against database sequences), cutoff, matrix, and filter (low complexity) can be at the default settings. The default scoring matrix used by blastp, blastx, tblastn, and tblastx is the BLOSUM62 matrix (Henikoff (1992), *Proc. Natl. Acad. Sci. USA* 89, 10915-10919), recommended for query sequences over 85 in length (nucleotide bases or amino acids).

For blastn, designed for comparing nucleotide sequences, the scoring matrix is set by the ratios of M (i.e., the reward score for a pair of matching residues) to N (i.e., the penalty score for mismatching residues), wherein the default values for M and N can be +5 and −4, respectively. Four blastn parameters can be adjusted as follows: Q=10 (gap creation penalty); R=10 (gap extension penalty); wink=1 (generates word hits at every winkth position along the query); and gapw=16 (sets the window width within which gapped alignments are generated). The equivalent Blastp parameter settings for comparison of amino acid sequences can be: Q=9; R=2; wink=1; and gapw=32. A Bestfit comparison between sequences, available in the GCG package version 10.0, can use DNA parameters GAP=50 (gap creation penalty) and LEN=3 (gap extension penalty), and the equivalent settings in protein comparisons can be GAP=8 and LEN=2. Thus, when referring to the polypeptide or nucleic acid sequences of the present disclosure, included are sequence identities of at least 40%, at least 45%, at least 50%, at least 55%, of at least 60%, at least 65%, at least 70%, at least 75%, at least 80%, or at least 85%, for example at least 86%, at least 87%, at least 88%, at least 89%, at least 90%, at least 91%, at least 92%, at least 93%, at least 94%, at least 95%, at least 96%, at least 97%, at least 98%, at least 99%, or about 100% sequence identity with the full-length polypeptide or nucleic acid sequence, or to fragments thereof comprising a consecutive sequence of at least 100, at least 125, at least 150 or more amino acid residues of the entire protein; variants of such sequences, e.g., wherein at least one amino acid residue has been inserted N- and/or C-terminal to, and/or within, the disclosed sequence(s) which contain(s) the insertion and substitution. Contemplated variants can additionally or alternately include those containing predetermined mutations by, e.g., homologous recombination or site-directed or PCR mutagenesis, and the corresponding polypeptides or nucleic acids of other species, including, but not limited to, those described herein, the alleles or other naturally occurring variants of the family of polypeptides or nucleic acids which contain an insertion and substitution; and/or derivatives wherein the polypeptide has been covalently modified by substitution, chemical, enzymatic, or other appropriate means with a moiety other than a naturally occurring amino acid which contains the insertion and substitution (for example, a detectable moiety such as an enzyme).

As used herein, the phrase "conservative amino acid substitution" or "conservative mutation" refers to the replacement of one amino acid by another amino acid with a common property. A functional way to define common properties between individual amino acids is to analyze the normalized frequencies of amino acid changes between corresponding proteins of homologous organisms (Schulz (1979) Principles of Protein Structure, Springer-Verlag). According to such analyses, groups of amino acids can be defined where amino acids within a group exchange preferentially with each other, and therefore resemble each other most in their impact on the overall protein structure (Schulz (1979) Principles of Protein Structure, Springer-Verlag). Examples of amino acid groups defined in this manner can include: a "charged/polar group" including Glu, Asp, Asn, Gln, Lys, Arg, and His; an "aromatic or cyclic group" including Pro, Phe, Tyr, and Trp; and an "aliphatic group" including Gly, Ala, Val, Leu, Ile, Met, Ser, Thr, and Cys. Within each group, subgroups can also be identified. For example, the group of charged/polar amino acids can be sub-divided into sub-groups including: the "positively-charged sub-group" comprising Lys, Arg and His; the "negatively-charged sub-group" comprising Glu and Asp; and the "polar sub-group" comprising Asn and Gln. In some examples, the aromatic or cyclic group can be sub-divided into sub-groups including: the "nitrogen ring sub-group" comprising Pro, His, and Trp; and the "phenyl sub-group" comprising Phe and Tyr. In another further example, the aliphatic group can be sub-divided into sub-groups including: the "large aliphatic non-polar sub-group" comprising Val, Leu, and Ile; the "aliphatic slightly-polar sub-group" comprising Met, Ser, Thr, and Cys; and the "small-residue sub-group" comprising Gly and Ala. Examples of conservative mutations include amino acid substitutions of amino acids within the sub-groups above, such as, but not limited to: Lys for Arg or vice versa, such that a positive charge can be maintained; Glu for Asp or vice versa, such that a negative charge can be maintained; Ser for Thr or vice versa, such that a free —OH can be maintained; and Gln for Asn or vice versa, such that a free —NH2 can be maintained. A "conservative variant" is a polypeptide that includes one or more amino acids that have been substituted to replace one or more amino acids of the reference polypeptide (for example, a polypeptide whose sequence is disclosed in a publication or sequence database, or whose sequence has been determined by nucleic acid sequencing) with an amino acid having common properties, e.g., belonging to the same amino acid group or sub-group as delineated above.

The term "essential", when referring to a gene or element, means a gene or element of an organism that are thought to be critical for the survival of the organism. For example, essential genes can encode proteins or RNAs that maintain central metabolism, replicate DNA, transcribe and translate genes into proteins, maintain a basic cellular structure, and mediate transport processes into and out of the cell. "Conditionally essential" genes or elements are those that are required or essential under certain circumstances, for instance, a gene required to digest starch is only essential if starch is the only energy source available to the organism. "Non-essential" genes or elements often convey a selective advantaged or increased fitness for the organism in certain circumstances, but are not absolutely required for life.

"Expression cassette" as used herein means a DNA sequence capable of directing expression of a particular nucleotide sequence in an appropriate host cell, comprising a promoter operably linked to a nucleotide sequence of interest, which can optionally be operably linked to termination signals and/or other regulatory elements. An expression cassette may also comprise sequences that enable, mediate, or enhance translation of the nucleotide sequence. The coding region usually codes for a protein of interest but may also code for a functional RNA of interest, for example antisense RNA or a non-translated RNA, in the sense or antisense direction. An expression cassette may be assembled entirely extracellularly (e.g., by recombinant cloning techniques). However, an expression cassette may also be assembled using in part endogenous components. For example, an expression cassette may be obtained by placing (or inserting) a promoter sequence upstream of an endogenous sequence, which thereby becomes functionally linked and controlled by said promoter sequences. The expression of the nucleotide sequence in the expression cassette may be under the control of a constitutive promoter or of an inducible promoter which initiates transcription only when the host cell is exposed to some particular external stimulus.

"Expression vector" refers to a vector comprising a recombinant polynucleotide comprising expression control sequences operatively linked to a nucleotide sequence to be expressed. An expression vector comprises sufficient cis-acting elements for expression; other elements for expression can be supplied by the host cell or in an in vitro expression system. Examples of expression vectors known in the art include cosmids, plasmids and viruses (e.g., retroviruses, lentiviruses, adenoviruses, and adeno-associated viruses) that incorporate the recombinant polynucleotide.

"Exogenous nucleic acid molecule" or "exogenous gene" refers to a nucleic acid molecule or gene that has been introduced ("transformed") into a cell. A transformed cell may be referred to as a recombinant cell or an engineered cell. A nucleic acid molecule is also exogenous if it is present in a descendent cell and received from an ultimate parent cell where that nucleic acid molecule was exogenous nucleic acid. The exogenous gene may be from a different species (thus also "heterologous"), or from the same species (thus "homologous"), relative to the cell being transformed.

The term "heterologous" when used in reference to a polynucleotide, gene, nucleic acid, polypeptide, or enzyme refers to a polynucleotide, gene, nucleic acid, polypeptide, or enzyme that is from a source or derived from a source other than the host organism species. Heterologous molecules are therefore always also exogenous, but exogenous molecules are not necessarily always heterologous. In contrast a "homologous" polynucleotide, gene, nucleic acid, polypeptide, or enzyme is used herein to denote a polynucleotide, gene, nucleic acid, polypeptide, or enzyme that is derived from the host organism species. When referring to a gene regulatory sequence or to an auxiliary nucleic acid sequence used for maintaining or manipulating a gene sequence (e.g., a promoter, a 5' untranslated region, 3' untranslated region, poly A addition sequence, intron sequence, splice site, ribosome binding site, internal ribosome entry sequence, genome homology region, recombination site, etc.), "heterologous" means that the regulatory sequence or auxiliary sequence is not naturally associated with the gene with which the regulatory or auxiliary nucleic acid sequence is juxtaposed in a construct, genome, chromosome, or episome. Thus, a promoter operably linked to a gene to which it is not operably linked to in its natural state (i.e., in the genome of a non-genetically engineered organism) is referred to herein as a "heterologous promoter," even though the promoter may be derived from the same species (or, in some cases, the same organism) as the gene to which it is linked.

A "recombinant" or "engineered" or "genetically engineered" nucleic acid molecule, polypeptide, organism, or combination thereof is a nucleic acid molecule, polypeptide, organism, or combination thereof that has been altered through human manipulation. As non-limiting examples, a recombinant nucleic acid molecule includes any nucleic acid molecule that: 1) has been partially or fully synthesized or modified in vitro, for example, using chemical or enzymatic techniques (e.g., by use of chemical nucleic acid synthesis, or by use of enzymes for the replication, polymerization, digestion (exonucleolytic or endonucleolytic), ligation, reverse transcription, transcription, base modification (including, e.g., methylation), integration or recombination (including homologous and site-specific recombination) of nucleic acid molecules); 2) includes conjoined nucleotide sequences that are not conjoined in nature, 3) has been engineered using molecular cloning techniques such that it lacks one or more nucleotides with respect to the naturally occurring nucleic acid molecule sequence, and/or 4) has been manipulated using molecular cloning techniques such that it has one or more sequence changes or rearrangements with respect to the naturally occurring nucleic acid sequence. As non-limiting examples, a cDNA is a recombinant DNA molecule, as is any nucleic acid molecule that has been generated by in vitro polymerase reaction(s), or to which linkers have been attached, or that has been integrated into a vector, such as a cloning vector or expression vector.

"Minimize/d" or "minimization" as used herein when referring to a genome, chromosome, or nucleic acid sequence, refers to removing non-essential nucleic acid sequences and/or rearranging the order of nucleic acid sequences which results in a smaller nucleic acid molecule than what was originally started with.

An "oligonucleotide", as used herein, is a nucleic acid molecule 200 or fewer nucleotides in length. An oligonucleotide can be RNA, DNA, or a combination of DNA and RNA, a nucleic acid derivative, or a synthetic nucleic acid, for example, an oligonucleotide can be a peptide nucleic acid or a locked nucleic acid, and can be single-stranded, double-stranded, or partially single-stranded and partially double-stranded. An oligonucleotide can be, for example, between about 4 and about 200 nucleotides in length, between about 6 and about 200 nucleotides in length, between about 10 and about 200 nucleotides in length, between about 15 and about 200 nucleotides in length, between about 17 and about 200 nucleotides in length, between about 20 and about 200 nucleotides in length, or between about 40 and about 200 nucleotides in length. In additional examples, an oligonucleotide can be between about 15 and about 180 nucleotides in length, between about 15 and about 160 nucleotides in length, between about 15 and about 140 nucleotides in length, between about 15 and about 120 nucleotides in length, between about 17 and about 100 nucleotides in length, between about 17 and about 80 nucleotides in length, or between about 17 and about 70 nucleotides in length, for example between about 20 and about 65 nucleotides in length, or between about 40 and about 80 nucleotides in length.

When used in reference to a polynucleotide, a gene, a nucleic acid, a polypeptide, or an enzyme, the term "heterologous" refers to a polynucleotide, gene, a nucleic acid, polypeptide, or an enzyme not derived from the host species, e.g., from a different species with respect to the host cell. When referring to nucleic acid sequences operably linked or otherwise joined to one another ("juxtaposed") in a nucleic acid construct or molecule, "heterologous sequences", as used herein, are those that are not operably linked or are not in proximity or contiguous to each other in nature. Similarly, when referring to a gene regulatory sequence or to an auxiliary nucleic acid sequence used for maintaining or manipulating a gene sequence (e.g., a 5' un-translated region, 3' un-translated region, Kozak sequence, poly A addition sequence, intron sequence, splice site, ribosome binding site, internal ribosome entry sequence, genome homology region, recombination site, e.g.), "heterologous" means that the regulatory sequence or auxiliary sequence is from a different source (e.g., different gene, whether from the same or different species as the host organisms) than the gene with which the regulatory or auxiliary nucleic acid sequence is juxtaposed or operably linked in a construct, genome, chromosome, or episome.

The terms "nucleic acid molecule" and "polynucleotide molecule" are used interchangeably herein, and refer to both DNA and RNA molecule, including cDNA, genomic DNA, synthetic DNA, and DNA or RNA containing nucleic acid analogs. Polynucleotides can have any three-dimensional structure. Polynucleotides can be natural-occurring or synthetic origin. A nucleic acid molecule can be double-stranded or single-stranded. Non-limiting examples of polynucleotides include genes, gene fragments, exons, introns, messenger RNA (mRNA), transfer RNA (tRNA), ribosomal RNA (rRNA), siRNA, micro-RNA, ribozymes, tracr RNAs, crRNAs, chimeric guide RNAs, cDNA, recombinant polynucleotides, branched polynucleotides, nucleic acid probes and nucleic acid primers. A polynucleotide may contain unconventional or modified nucleotides.

As used herein, "operably linked" is intended to mean a functional linkage between two or more sequences such that activity at or on one sequence affects activity at or on the other sequence(s). For example, an operable linkage between a polynucleotide of interest and a regulatory sequence (e.g., a promoter) is a functional link that allows for expression of the polynucleotide of interest. In this sense, the term "operably linked" refers to the positioning of a regulatory region and a coding sequence to be transcribed so that the regulatory region is effective for regulating transcription or translation of the coding sequence of interest. For example, to operably link a coding sequence and a regulatory region, the translation initiation site of the translational reading frame of the coding sequence is typically positioned between one and about fifty nucleotides downstream of the regulatory region. A regulatory region can, however, be positioned as much as about 5,000 nucleotides upstream of the translation initiation site, or about 2,000 nucleotides upstream of the transcription start site. Operably linked elements may be contiguous or non-contiguous. When used to refer to the joining of two protein coding regions, by "operably linked" is intended that the coding regions are in the same reading frame. When used to refer to the effect of an enhancer, "operably linked" indicated that the enhancer increases the expression of a particular polypeptide or polynucleotides of interest. "Juxtaposed with" in the context of nucleic acid sequences, means the referenced sequences are part of the same continuous nucleic acid molecule.

The terms "polynucleotide sequence" and "nucleic acid sequence" as used herein interchangeably refer to a sequence of a polynucleotide molecule, and can refer, for example, to DNA or RNA sequences. The nomenclature for nucleotide bases as set forth in 37 CFR § 1.822 is used herein.

The term "promoter" refers to a nucleic acid sequence capable of binding RNA polymerase in a cell and initiating transcription of a downstream (3' direction) coding sequence. A promoter includes the minimum number of bases or elements necessary to initiate transcription at levels detectable above background. A promoter can include a transcription initiation site as well as protein binding domains (consensus sequences) responsible for the binding of RNA polymerase. Eukaryotic promoters often, but not always, contain "TATA" boxes and "CAT" boxes. Prokaryotic promoters may contain −10 and −35 prokaryotic promoter consensus sequences. A large number of promoters, including constitutive, inducible and repressible promoters, from a variety of different sources are well known in the art. Representative sources include for example, algal, viral, mammalian, insect, plant, yeast, and bacterial cell types, and suitable promoters from these sources are readily available, or can be made synthetically, based on sequences publicly available on line or, for example, from depositories such as the ATCC as well as other commercial or individual sources. Promoters can be unidirectional (initiate transcription in one direction) or bi-directional (initiate transcription in either direction). A promoter may be a constitutive promoter, a repressible promoter, or an inducible promoter. Such promoters need not be of naturally-occurring sequences. In addition, it will be understood that such promoters need not be derived from the target host cell or host organism.

"Polypeptide" and "protein" are used interchangeably herein and refer to a compound of two or more subunit amino acids, amino acid analogs, or other peptidomimetics, regardless of post-translational modification, e.g., phosphorylation or glycosylation. The subunits may be linked by peptide bonds or other bonds such as, for example, ester or ether bonds. Full-length polypeptides, truncated polypeptides, point mutants, insertion mutants, splice variants, chimeric proteins, and fragments thereof are encompassed by this definition. In various embodiments the polypeptides can have at least 10 amino acids or at least 25, or at least 50 or at least 75 or at least 100 or at least 125 or at least 150 or at least 175 or at least 200 amino acids.

As used herein the term "biomolecule" means any molecule that is present in living organisms or that is produced by living organisms, including large macromolecules such as proteins, polysaccharides, lipids, and nucleic acids, as well as small molecules such as primary metabolites, secondary metabolites, and natural products. A more general name for this class of material is biological materials.

As used herein "progeny" means a descendant, offspring, or derivative of an organism. For example, daughter cells from a transgenic alga are progeny of the transgenic alga. Because certain modifications may occur in succeeding generations due to mutations or environmental influences, such progeny, descendant, or derivatives may not, in fact, be identical to the parent cell, but are still included within the scope of the term as used herein.

The terms "recombinant" or "engineered" as used herein in reference to a nucleic acid molecule, refer to a nucleic acid molecule that has been altered through human intervention. As non-limiting examples, a cDNA is a recombinant DNA molecule, as is any nucleic acid molecule that has been generated by in vitro polymerase reaction(s), or to which linkers have been attached, or that has been integrated into a vector, such as a cloning vector or expression vector. As non-limiting examples, a recombinant nucleic acid molecule: 1) has been synthesized or modified in vitro, for example, using chemical or enzymatic techniques (for example, by use of chemical nucleic acid synthesis, or by use of enzymes for the replication, polymerization, exonucleolytic digestion, endonucleolytic digestion, ligation, reverse transcription, transcription, base modification (including, e.g., methylation), or recombination (including homologous and site-specific recombination)) of nucleic acid molecules; 2) includes conjoined nucleotide sequences that are not conjoined in nature; 3) has been engineered using molecular cloning techniques such that it lacks one or more nucleotides with respect to the naturally occurring nucleic acid molecule sequence; and/or 4) has been manipulated using molecular cloning techniques such that it has one or more sequence changes or rearrangements with respect to the naturally occurring nucleic acid sequence. A "recombinant protein" is a protein produced by genetic engineering, for example, by expression of a genetically engineered nucleic acid molecule in a cell.

The term "regulatory region", "regulatory sequence", "regulatory element", or "regulatory element sequence", as used in the present disclosure, refer to a nucleotide sequence that influences transcription or translation initiation or rate, and stability and/or mobility of a transcription or translation product. Such regulatory regions need not be of naturally-occurring sequences. Regulatory sequences include but are not limited to promoter sequences, enhancer sequences, response elements, protein recognition sites, inducible elements, protein binding sequences, 5' and 3' un-translated regions (UTRs), transcriptional start sites, termination sequences, polyadenylation sequences, introns, and combinations thereof. A regulatory region typically comprises at least a core (basal) promoter. A regulatory region also may include at least one control element, such as an enhancer sequence, an upstream element or an upstream activation region (UAR).

As used herein, the terms "chromosomal replication machinery" or "replication machinery" mean that part of an organism's chromosome which supports replication within the organism or in a different organism. In some aspects of the present disclosure, replication machinery refers a 5-6 kb or 5-5.5 kb or about 5.5 kb sequence from chromosome II of *V. natriegens* which is capable of supporting replication in an organism. In certain aspects, the replication machinery from *V. natriegens* can support replication in *V. natriegens* and *E. coli*. In other aspects of the present disclosure, the replication machinery has at least about 60%, at least about 70%, at least about 80%, at least about 90%, or at least about 95%, or at least about 97%, or at least about 98%, or at least about 99% sequence identity or homology to the sequence of SEQ ID NO: 1 or a variant thereof. SEQ ID NO: 1 comprises an origin of replication operable in *Vibrio* sp. and in *E. coli*.

As used herein, "transgenic organism" refers to an organism which comprises a heterologous polynucleotide. When applied to organisms, the terms "transgenic" or "recombinant" or "engineered" or "genetically engineered," used interchangeably herein, refer to organisms that have been manipulated by introduction into the organism of an exogenous or recombinant nucleic acid sequence. Generally, the heterologous polynucleotide is stably integrated within the genome such that the polynucleotide is passed on to successive generations, although it can also be present on an episome, and may be present on a synthetic chromosome of the transgenic organism. The non-native polynucleotide may be integrated into the genome alone or as part of a recombinant expression cassette. In additional examples, a transgenic microorganism can include an introduced exogenous regulatory sequence operably linked to an endogenous gene of the transgenic microorganism. Non-limiting examples of such manipulations include gene knockouts, targeted mutations and gene replacement, promoter replacement, deletion, or insertion, as well as introduction of transgenes into the organism. Recombinant or genetically engineered organisms can also be organisms into which constructs for gene "knock down" have been introduced. Such constructs include, but are not limited to, RNAi, microRNA, shRNA, antisense, and ribozyme constructs. Also included are organisms whose genomes have been altered by the activity of meganucleases, TALENs, zinc finger nucleases, or CRISPR nucleases. As used herein, "recombinant microorganism" or "recombinant host cell" includes progeny or derivatives of the recombinant microorganisms of the disclosure. Because certain modifications may occur in succeeding generations from either mutation or environmental influences, such progeny or derivatives may not, in fact, be identical to the parent cell, but are still included within the scope of the term as used herein.

For nucleic acids and polypeptides, the term "variant" is used herein to denote a polypeptide, protein, or polynucleotide molecule with some differences, generated synthetically or naturally, in their base or amino acid sequences as compared to a reference polypeptide or polynucleotide, respectively, such that the variant has at least 70% sequence identity with the reference polypeptide or polynucleotide. In other embodiments the variant can have at least 80%, at least 85%, at least 90%, at least 95%, at least 96%, at least 97%, at least 98%, or at least 99% sequence identity with the reference polypeptide or polynucleotide. In other embodiments the variant has a sequence identity of at least 70% or at least 80% or at least 90% or at least 95% or at least 97% or at least 98% or at least 99% or 90-99% or 95-99% or 97-99% to a sequence of at least 5 or at least 7 or at least 10 or at least 15 or at least 20 or at least 30 or at least 40 or at least 50 or at least 100 or at least 200 or at least 300 or at least 400 or at least 500 or at least 600 or at least 700 or at least 800 or at least 900 or at least 1000 or at least 2000 or at least 3000 at least 4000 or at least 5000 consecutive nucleotides or amino acids from the reference sequence (e.g., SEQ ID NO: 1-25 or any sequence described herein). Alternatively, or in addition, a variant can have one or two or three or four or five or six or seven or eight or nine or ten or more insertions or deletions in response to a reference polypeptide or polynucleotide. For example, protein variants may be N-terminally truncated or C-terminally truncated with respect to the reference sequence, or can have one or more internal deletions, while nucleic acid variants may have a 5' end and/or 3'end sequence truncation and/or can have one or more internal deletions. Further, a protein variant may have an additional sequence added to the N-terminus and/or C-terminus with respect to the reference sequence, or can have one or more internal additional sequences, while nucleic acid variants may have a 5' end and/or 3'end sequence addition and/or can have one or more internal sequence additions. A variant can have any desired combination of substitutions, insertions, and/or deletions with respect to a reference polypeptide or polynucleotide. Polypeptide and protein variants can further include differences in post-translational modifications (such as glycosylation, methylation, phosphorylation, e.g.). When the term "variant" is used in reference to a microorganism, it typically refers to a strain microbial strain having identifying characteristics of the species to which it belongs, while having at least one nucleotide sequence variation or identifiably different trait with respect to the parental strain, where the trait is genetically based (heritable).

A "vector" is any genetic element capable of serving as a vehicle of genetic transfer, expression, or replication for a foreign polynucleotide in a host cell. For example, a vector may be an artificial chromosome or a plasmid, and may be capable of stable integration into a host cell genome, or it may exist as an independent genetic element (e.g., episome, plasmid). A vector may exist as a single polynucleotide or as two or more separate polynucleotides. Vectors may be single copy vectors or multicopy vectors when present in a host cell.

*Vibrio* is a genus of Gram-negative, facultative anaerobic bacteria possessing a curved-rod shape. In some embodiments, *Vibrio* sp. comprises one or more of the following *Vibrio* species: *adaptatus, aerogenes, aestivus, aestuarianus, agarivorans, albensis, alfacsensis, alginolyticus, anguillarum, areninigrae, artabrorum, atlanticus, atypicus, azureus, brasiliensis, bubulus, calviensis, campbellii, casei, chagasii, cholera, cincinnatiensis, coralliilyticus, crassostreae, cyclitrophicus, diabolicus, diazotrophicus, ezurae, fischeri, fluvialis, fortis, furnissii, gallicus, gazogenes, gigantis, halioticoli, harveyi, hepatarius, hippocampi, hispanicus, hollisae, ichthyoenteri, indicus, kanaloae, lentus, litoralis, logei, mediterranei, metschnikovii, mimicus, mytili, natriegens, navarrensis, neonates, neptunius, nereis, nigripulchritudo, ordalii, orientalis, pacinii, parahaemolyticus, pectenicida, penaeicida, pomeroyi, ponticus, proteolyticus, rotiferianus, ruber, rumoiensis, salmonicida, scophthalmi, splendidus, superstes, tapetis, tasmaniensis, tubiashii, vulnificus, wodanis*, and *xuii*. In some embodiments, *Vibrio* sp. is not *Vibrio cholera*. In some embodiments, *Vibrio* sp. comprises all known species of *Vibrio* other than cholera. In some embodiments, *Vibrio* sp. comprises *Vibrio natriegens*. In a preferred embodiment, *Vibrio* sp. is *Vibrio natriegens*.

*Vibrio natriegens* is a Gram-negative marine bacterium. It was first isolated from salt marsh mud and is a *halophile* requiring about 2% NaCl for growth. It reacts well to the presence of sodium ions which appear to stimulate growth in *Vibrio* species, to stabilize the cell membrane, and to affect sodium-dependent transport and mobility. Under optimum conditions, and all nutrients provided, the doubling time of *V. natriegens* can be less than 10 minutes. Its rapid growth rate (the fastest known doubling time of any organism), its ability to thrive in inexpensive, defined media, its ability to serve as a drop-in replacement for *E. coli* strains for common lab processes, its unique genome architecture (which can be leveraged to facilitate the cloning of large DNAs), and the potential to leverage natural transformation and conjugation as genetic engineering tools makes *V. natriegens* an attractive host. It has the potential to dramatically speed up standard workflows, as well as to make possible projects that are too ambitious for the current state of the art.

*Vibrio* sp. has several advantages over other bacteria for many molecular biology applications. One such advantage is the rapid growth rate of *Vibrio* sp. One of the most time intensive steps in modern biotech workflows is in waiting for the host to grow to a sufficient density before DNA/protein/product can be recovered or the phenotype can be assessed. As dramatic time savings have been realized in other areas of biotech workflows (e.g., sequencing, bioinformatic analysis, high-throughput assays, etc.), growth of the host has become a significant bottleneck. *E. coli* is considered to have one of the quickest growth rates relative to other organisms used in the biotech sector, which has been one of its strengths. Because *Vibrio natriegens* has a growth rate 2-3× faster than commonly used *E. coli* strains, it is able to effect a dramatic reduction in the time necessary for the host to grow, and will accelerate research efforts. In certain aspects of the present disclosure, the growth rate of *Vibrio* sp. is about 10 minutes. In other aspects, the growth rate of a genetically engineered *Vibrio* sp. is about 5 minutes to 30 minutes. In various embodiments the *Vibrio* sp. organisms of the invention have a doubling time of less than 15 minutes or less than 14 minutes or less than 13 minutes or less than 12 minutes or less than 11 minutes or less than 10 minutes, or less than 9 minutes. The doubling time can be achieved by the organism in a rich media, meaning that it is rich in nitrogen and carbon. The doubling times described can be achievable in any of the media described herein (e.g., any described in Example 1). In specific examples the doubling times disclosed can be achieved in an LB broth, in LB agar, in Nutrient Broth+1.5% NaCl, in Brain Heart Infusion (with or without salts), Brain Heart Infusion Agar (with or without salts), SSG agar, 2xYT+salts+glucose+phosphate buffer, Vegitone Infusion Broth (with optional salts), LB+salts+glucose+phosphate buffer. Example formulations of these media are described in Example 1. Any of the salts or other media components can be as described herein, for example as in Example 1. In various embodiments doubling times can be measured at the flat or log portion of the curve.

Another advantage is the size of exogenous DNA that can be harbored in *Vibrio* sp. Large scale genetic engineering/synthetic genome construction efforts require the assembly, manipulation, and maintenance of large pieces of recombinant DNA, tasks which are carried out in a genetically tractable host (such as *E. coli*) before delivery of the engineered DNA to the final host organism. Currently, most of this work is carried out in *E. coli*, but as projects become more ambitious, the limitations of this species are becoming apparent. It has been observed that with current technologies, *E. coli* is capable of harboring exogenous DNA constructs of no more than 500 kb (and in some cases much less depending on the properties of the DNA being cloned) on a bacterial artificial chromosome, which is a serious limitation for synthetic genome/large pathway construction efforts. This has necessitated the development of novel hosts as cloning platforms such as *Saccharomyces cerevisiae* and *Bacillus subtilis*. While these hosts have the advantage of being able to take up and stably propagate large (Mb-sized) fragments of exogenous DNA, they have their own disadvantages, with *Saccharomyces cerevisiae* growing much slower than *E. coli* (~3× slower), and both species being incompatible with standard laboratory techniques and being very difficult to recover DNA from.

An additional advantage is the compatibility of *Vibrio* sp. with standard lab protocols: Unlike other niche organisms, which often require specialized techniques/methods, *Vibrio* sp. is compatible with many standard cloning vectors, growth media, workflows and commercially-available kits developed for *E. coli* or recovering DNA. This compatibility with standard tools/reagents/methods lowers the barrier to adoption by labs that are currently dependent on *E. coli*, allowing for drop-in replacement.

A further advantage is the nutritional versatility of *Vibrio* sp. One additional benefit of *Vibrio* sp. is its extreme nutritional versatility, allowing it to grow on a range of different growth media, including inexpensive, minimal media. Coupled with its rapid growth rate, this feature will allow for industrial scale production of biomolecules (e.g., therapeutic proteins, commodity chemicals, etc.) cheaper and faster than the state of the art. As described in the Examples, *V. natriegens* and a genetically engineered *V. natriegens* are capable of growing under a variety of nutrient and temperature conditions.

Members of Vibrionaceae have a unique two-chromosome genome, herein referred to as Chromosome I and Chromosome II. A genetically engineered *V. natriegens* can be constructed with a single, large chromosome which incorporates the essential features from the smaller chromosome into the large chromosome. In this genetically engineered *V. natriegens*, the now "free" chromosomal machinery can be leveraged as a vector for cloning large DNAs/pathways. The smaller second chromosome of *V. natriegens* can be capable of replicating/maintaining a ~2 Mb fragment of DNA showing that the use of chromosome II as a cloning vector can allow for the rapid and robust propagation of large exogenous DNA molecules (e.g., synthetic or semi-synthetic chromosomes for ultimate use in other organisms, or novel pathways/genetic elements for use in *V. natriegens* itself) as well as the production of polypeptides and biomolecules.

In some embodiments, the present disclosure provides genetically engineered *Vibrio* sp. bacteria comprising one or two altered, rearranged, or minimized chromosomes. In some examples, the essential elements from Chromosome II are alternatively located on Chromosome I. In some examples, the engineered bacteria contain a single chromosome comprising the essential features of Chromosome I and II. In some examples, the engineered *Vibrio* sp. are generated by knocking out and/or knocking in appropriate genes in order to generate the desired engineered *Vibrio* sp. In some examples the knock in and/or knock out and/or sequence inversion is enabled through the enzyme activity of a recombinase, such as, for example, Cre recombinase. In some examples, the Cre recombinase activity utilizes known lox sites compatible with Cre recombinase. In some examples, the knock in and/or knock out is enabled through the enzyme activity of a nuclease, such as, for example, Type II CRISPR Cas9. In some examples, the knock in and/or knock out is enabled through the use of a homologous recombination vector containing regions of sequence homology to a region in the genome where an insertion or deletion is desired. In some examples, the homologous recombination vector is incorporated by a single cross-over event. In some examples, the homologous recombination vector is incorporated by a double-cross-over event. In some examples the knock in and/or knock out event is enables through use of an integrase, such as, for example, PhiC31 or bxb1. In some examples, the knock in and/or knock out is enabled through the use of a suicide vector. In some examples the vector is assembled in vitro and subsequently transformed and amplified in *E. coli*. In some examples the vector is assembled in *S. cerevisiae*. In some examples, the amplified vector is introduced into *V natriegens* by conjugation, electroporation, chemical competence, biolistics, transduction, or via natural competence.

In some examples, the genetically engineered *Vibrio* sp. comprises altered chromosomes or a combined single chromosome, either of which has been minimized, whereby non-essential genes and nucleic acid sequences have been removed. Non-limiting examples of non-essential genes include exonucleases, endonucleases, methylases, nucleases, restriction enzymes, complete restriction-modification systems, or any combination thereof. Non-essential genes or genetic elements can be identified bioinformatically or experimentally. Bioinformatic identification can involve comparing multiple wild types *V. natriegens* strain genomes and identifying genes or nucleic acid sequences that are not consistently present in all strains. Experimental identification of non-essential genes can be achieved by transposon bombardment or other insertional mutagenesis screens that will produce multiple random integration mutants. By sequencing the genes disrupted in these viable mutants, non-essential genes will be identified. In some examples, the non-essential genes can be sequentially removed by homologous recombination based techniques. In some examples, the minimization can be achieved sequentially through known techniques, such as multiplex automated genome engineering (MAGE) or hierarchical conjugative assembly (CAGE).

In some embodiments, the present disclosure provides genetically engineered *Vibrio* sp. bacteria comprising an altered chromosomal arrangement. In some aspects, one or more non-essential elements are removed from Chromosome I and/or Chromosome II. In some aspects, one or more elements from Chromosome II are alternatively located on Chromosome I. In some aspects, one or more elements from Chromosome II are alternatively located on Chromosome I. In some aspects, the genetically engineered *Vibrio* sp. comprises a single chromosome. In some aspects, the single chromosome contains essential genomic elements from *Vibrio* sp. Chromosome I and II. In some examples, non-limiting examples of an essential element is a gene required for a function selected from the group consisting of metabolism, DNA replication, transcription, translation, cellular structural maintenance, transport processes into or out of the cell, or any combination thereof.

In some aspects, the one or two chromosomes are "minimized", whereby non-essential elements have been removed. In some aspects, the bacteria grow at temperature from about 25° C. to about 42° C. In some aspects, the growth doubling time is about 5 minutes to 15 minutes. In some examples, the minimized chromosome or single chromosome comprises essential elements from Chromosome I and Chromosome II such that the minimized or single chromosome is capable of supporting survival and replication of the bacteria under non-selective conditions.

In some aspects, the herein disclosed genetically engineered *Vibrio* sp. further comprises a heterologous nucleic acid sequence operably linked to a heterologous promoter. In some examples the heterologous nucleic acid encodes T7 RNA polymerase. In some examples, the heterologous promoter is an inducible promoter. The inducible promoter can be induced by temperature, arabinose, or IPTG as non-limiting examples.

In some embodiments, the present disclosure provides a process for producing competent *Vibrio* sp. cells comprising growing genetically modified *Vibrio* sp. bacterial cells in a growth-conducive medium; rendering said *Vibrio* sp. bacterial cells competent; and freezing the cells. In some aspects, the *Vibrio* sp. are any of those genetically engineered *Vibrio* sp. described herein. In some aspects, rendering the cells competent comprises growing the cells in conducive media supplemented with supplemental salts.

In some embodiments, the present disclosure provides a method of producing a biomolecule comprising a) providing a *Vibrio* sp. having an exogenous nucleic acid that comprises a heterologous nucleic acid sequence encoding the biomolecule. The method can, optionally, include a step of contacting the *Vibrio* sp. with the exogenous nucleic acid and introducing it into the bacteria; the exogenous nucleic acid can be a plasmid, expression vector, or other vector that encodes a heterologous nucleic acid sequence; b) growing the bacteria in a growth-conducive medium wherein the heterologous nucleic acid sequence is expressed, thereby producing the biomolecule; and optionally c) isolating the biomolecule. In some embodiments the exogenous nucleic acid can encode a signal sequence that causes the biomolecule to be secreted from the organism when produced. The biomolecule can therefore be expressed with a signal sequence attached. In some examples, the bacteria are any of the genetically engineered *Vibrio* sp. bacteria disclosed herein, for example a *Vibrio natriegens*. In some examples, the exogenous nucleic acid comprises a nucleic acid sequence encoding *Vibrio* sp. replication machinery of SEQ ID NO: 1 or a variant thereof. In some examples, the exogenous nucleic acid further comprises an inducible promoter operably linked to the heterologous nucleic acid encoding the biomolecule. In some aspects, the exogenous nucleic acid comprises replication machinery compatible with one or more organisms. In some examples the replication machinery is compatible with a heterologous host, such as, for example, *E. coli* or *S. cerevisiae*. Alternatively, or additionally, the replication machinery is from *V. natriegens*. In some aspects, the heterologous nucleic acid is at least 1 kb or at least 10 kb, or at least 25 kb, or at least 50 kb, or at least 75 kb, or at least 100 kb, or at least 125 kb, or at least 150 kb, or at least 175 kb, or at least 200 kb, or at least 250 kb, or at least 300 kb, or at least 350 kb, or at least 400 kb, or at least 500 kb, or at least 600 kb, or at least 700 kb, or at least 800 kb, or at least 900 kb or at least 1 Mb, or 2 Mb, or 3 Mb, or 5 Mb, or 7 Mb, or 10 kb-1 Mb or 25 kb-1 Mb or 50 kb-1 Mb or 100 kb-1 Mb or 50 kb-2 Mb or 50 kb-3 Mb or 50 kb-5 Mb or 50 kb-7 Mb, or 30 kb-1 Mb or 100 kb-1 Mb or 30 kb-2 Mb or 30 kb-3 Mb or 30 kb-5 Mb or 30 kb-7 Mb or 100 kb-2 Mb or 100 kb-3 Mb or 100 kb-5 Mb or 100 kb-7 Mb. In a specific aspect, the heterologous nucleic acid is at least about 500 kb. In some aspects, the heterologous nucleic acid also comprises an inducible promoter, an origin of replication, an origin of transfer, a selectable marker, a counter-selectable marker, a reporter gene, a regulatory element, an enzyme gene, or a combination thereof. In some aspects, the selectable marker is an antibiotic resistance gene, a gene encoding a polypeptide conferring resistance to a toxin, an auxotrophic marker or a combination thereof. In some aspects, the antibiotic resistance gene confers resistance to antibiotics which is bleomycin, carbenicillin, chloramphenicol, gentamycin, glyphosate, hygromycin, kanamycin, neomycin, nourseothricin, phleomycin, puromycin, spectinomycin, streptomycin, or tetracyclin. In some examples, the reporter gene can be a fluorescent protein or beta-galactosidase. In some aspects, the enzyme is a recombinase, integrase, nuclease, recombineering enzymes, or polymerase. In some examples the recombinase is Cre recombinase. In some examples, the integrase is PhiC31 or bxb1. In some examples the nuclease is a TypeII CRISPR Cas9 nuclease. In some examples, the polymerase is a Sp6, T3, or T7 RNA polymerase. In some aspects, the inducible promoter is induced by IPTG, arabinose, or temperature. In some examples, the *Vibrio* sp. bacterial cells are naturally competent. In some examples, the *Vibrio* sp. cells are competent cells generated by any of the methods disclosed herein. In some aspects, the heterologous nucleic acid is introduced into the cell by conjugation, chemical competence, natural competence, biolistics, transduction, or electroporation. In some aspects, the growth conducive media is monitored for the presence of the biomolecule. In other embodiments the heterologous nucleic acid sequence is not expressed, but the exogenous vector is cloned in the *Vibrio* sp. organism. Growth-conducive media support growth of the organism and examples are provided herein.

In some aspects, the present disclosure provides an isolated or synthesized nucleic acid molecule comprising SEQ ID NO:1 or a variant thereof. In some examples, the isolated or synthesized nucleic acid molecule further comprises heterologous sequence on the 5' and 3' end, wherein the heterologous 5' and 3' sequences are compatible for cloning into a target vector. Cloning can be performed by any known methods in the art.

In some aspects, the present disclosure provides vectors comprising *Vibrio* sp. chromosomal replication machinery. In some examples, the replication machinery comprises SEQ ID NO: 1 or a variant thereof. In some examples, the vector further comprises a heterologous nucleic acid of interest. In some examples, the vector further comprises an inducible promoter operably linked to a nucleic acid of interest. In some examples, the vector is capable of replication in *E. coli* or *S. cerevisiae*.

In some embodiments, the present disclosure provides a vector comprising the replication machinery from a *Vibrio* sp. chromosome. In some aspects, the replication machinery is that of Chromosome II from *Vibrio* sp. bacteria. In some aspects, the replication machinery comprises SEQ ID NO: 1 or a variant thereof. In some aspects, the vector comprises a heterologous nucleic acid of interest. In some aspects, the nucleic acid of interest is at least 1 kb or at least 10 kb, or at least 25 kb, or at least 50 kb, or at least 75 kb, or at least 100 kb, or at least 125 kb, or at least 150 kb, or at least 175 kb, or at least 200 kb, or at least 250 kb, or at least 300 kb, or at least 350 kb, or at least 400 kb, or at least 500 kb, or at least 600 kb, or at least 700 kb, or at least 800 kb, or at least 900 kb or at least 1 Mb, or 2 Mb, or 3 Mb, or 5 Mb, or 7 Mb, or 10 kb-1 Mb or 25 kb-1 Mb or 50 kb-1 Mb or 100 kb-1 Mb or 50 kb-2 Mb or 50 kb-3 Mb or 50 kb-5 Mb or 50 kb-7 Mb, or 30 kb-1 Mb or 100 kb-1 Mb or 30 kb-2 Mb or 30 kb-3 Mb or 30 kb-5 Mb or 30 kb-7 Mb or 100 kb-2 Mb or 100 kb-3 Mb or 100 kb-5 Mb or 100 kb-7 Mb. In some aspects, the vector can have a promoter, an origin of replication, an origin of transfer, selectable marker, a counter selectable marker, a reporter gene, a regulatory element, an enzyme gene, or any combination thereof, including that one or more of the elements may be omitted. In some aspects, the selectable marker is an antibiotic resistance gene, a gene encoding a polypeptide conferring resistance to a toxin, an auxotrophic marker, or a combination thereof. In some aspects, the antibiotic resistance gene confers resistance to antibiotics which is bleomycin, carbenicillin, chloramphenicol, gentamycin, glyphosate, hygromycin, kanamycin, neomycin, nourseothricin, phleomycin, puromycin, spectinomycin, streptomycin, or tetracyclin. In some examples, the reporter gene can be a fluorescent protein or beta-galactosidase. In some aspects, the enzyme is a recombinase, integrase, nuclease, recombineering enzymes, or polymerase. In some examples the recombinase is Cre recombinase. In some examples the integrase is PhiC31 or bxb1. In some examples the nuclease is a TypeII CRISPR Cas9 nuclease. In some examples, the polymerase is a Sp6, T3, or T7 RNA polymerase. In some aspects, the vector is compatible with *E. coli, V. natriegens*, and/or *S. cerevisiae*. In some aspects, the inducible promoter is induced by IPTG, arabinose, or temperature.

Any of the nucleic acids or vectors disclosed herein can utilize an inducible promoter. In addition to the inducible promoters described herein, the inducible promoter can also be any chemically regulated, tetracycline regulated, steroid regulated, metal regulated or pathogenesis regulated promoter. Examples of chemically inducible promoters include the AlcA promoter, which is induced by alcohol or a ketone. Any of the promoters can also be inducible by physical parameters, for example temperature-inducible or light inducible.

In some aspects, the present disclosure provides a composition comprising any of the genetically engineered *Vibrio* sp. disclosed herein. In some examples, the genetically engineered *Vibrio* sp. bacteria disclosed herein are naturally competent. In some examples, the genetically engineered *Vibrio* sp. bacteria are competent cells generated by any of the methods disclosed herein. In some examples, the competent genetically engineered *Vibrio* sp. bacteria are generated by the process of: (a) growing genetically modified *Vibrio* sp. bacterial cells in a growth-conducive medium; (b) rendering said *Vibrio* sp. bacterial cells competent; and (c) freezing the cells.

In some aspects, the present disclosure provides an expression system which comprises a vector comprising the *Vibrio* sp. chromosomal replication machinery. In some examples, the replication machinery comprises SEQ ID NO:1 or a variant thereof. In some examples, the vector further comprises a heterologous nucleic acid of interest, such as any described herein. In some examples, the vector further comprises an inducible promoter operably linked to a nucleic acid of interest. In some examples, the vector is capable of replication in *E. coli* or *S. cerevisiae*. In some aspects, the vector further comprises a promoter, an origin of replication, an origin of transfer, a selectable marker, a counter-selectable marker, a reporter gene, a regulatory element, an enzyme gene, or a combination thereof. In some aspects, selectable marker is an antibiotic resistance gene, a gene encoding a polypeptide conferring resistance to a toxin, an auxotrophic marker, or any combination thereof, including that one or more elements can be omitted. In some aspects, the antibiotic resistance gene confers resistance to antibiotics which is bleomycin, carbenicillin, chloramphenicol, gentamycin, glyphosate, hygromycin, kanamycin, neomycin, nourseothricin, phleomycin, puromycin, spectinomycin, streptomycin, or tetracyclin. In some examples, the reporter gene can be a fluorescent protein or beta-galactosidase. In some aspects, the enzyme is a recombinase, integrase, nuclease, recombineering enzymes, or polymerase. In some examples the recombinase is Cre recombinase. In some examples the integrase is PhiC31 or bxb1. In some examples the nuclease is a TypeII CRISPR Cas9 nuclease. In some examples, the polymerase is a Sp6, T3, or T7 RNA polymerase. In some aspects, the replication machinery comprises SEQ ID NO: 1. In some aspects, the vector is compatible with *E. coli, V. natriegens*, and/or *S. cerevisiae*. In some aspects, the inducible promoter is induced by IPTG, arabinose, or temperature. In some aspects, the vector further comprises a nucleic acid of interest. In some aspects, the polynucleotide of interest is at least 1 kb or at least 10 kb, or at least 25 kb, or at least 50 kb, or at least 75 kb, or at least 100 kb, or at least 125 kb, or at least 150 kb, or at least 175 kb, or at least 200 kb, or at least 250 kb, or at least 300 kb, or at least 350 kb, or at least 400 kb, or at least 500 kb, or at least 600 kb, or at least 700 kb, or at least 800 kb, or at least 900 kb or at least 1 Mb, or 2 Mb, or 3 Mb, or 5 Mb, or 7 Mb, or 10 kb-1 Mb or 25 kb-1 Mb or 50 kb-1 Mb or 100 kb-1 Mb or 50 kb-2 Mb or 50 kb-3 Mb or 50 kb-5 Mb or 50 kb-7 Mb, or 30 kb-1 Mb or 30 kb-2 Mb or 30 kb-3 Mb or 30 kb-5 Mb or 30 kb-7 Mb or 100 kb-2 Mb or 100 kb-3 Mb or 100 kb-5 Mb or 100 kb-7 Mb.

In some aspects, the present disclosure provides host cells comprising a vector comprising *Vibrio* sp. chromosomal replication machinery. In some examples, the host cells are naturally competent. In some examples, the host cells are competent cells generated by any of the herein disclosed methods. In some examples, the vector is introduced into the host cell by transformation, transduction, biolistics, conjugation, chemical competence, natural competence, or electroporation. In some examples, the replication machinery comprises SEQ ID NO: 1 or a variant thereof. In some examples, the vector further comprises a heterologous nucleic acid of interest. In some examples, the vector further comprises an inducible promoter operably linked to a nucleic acid of interest. In some examples, the host cells are any genetically engineered *Vibrio* sp. bacteria disclosed herein. In some aspects, the vector further comprises a promoter, an origin of replication, an origin of transfer, a selectable marker, a counter selectable marker, a reporter gene, a regulatory element, an enzyme gene, or a combination thereof. In some aspects, the selectable marker is an antibiotic resistance gene, a gene encoding a polypeptide conferring resistance to a toxin, an auxotrophic marker, or a combination thereof. In some aspects, the antibiotic resistance gene confers resistance to antibiotics which is bleomycin, carbenicillin, chloramphenicol, gentamycin, glyphosate, hygromycin, kanamycin, neomycin, nourseothricin, phleomycin, puromycin, spectinomycin, streptomycin, or tetracyclin. In some examples, the reporter gene can be a fluorescent protein or beta-galactosidase. In some aspects, the enzyme is a recombinase, integrase, nuclease, recombineering enzymes, or polymerase. In some examples the recombinase is Cre recombinase. In some examples the integrase is PhiC31 or bxb1. In some examples the nuclease is a TypeII CRISPR Cas9 nuclease. In some examples, the polymerase is a Sp6, T3, or T7 RNA polymerase. In some aspects, the inducible promoter is induced by IPTG, arabinose, or temperature. In some aspects, the vector is alternatively or additionally compatible with *E. coli* and/or *S. cerevisiae*. In some aspects, the vector further comprises a nucleic acid of interest. In some aspects, the nucleic acid of interest is at least 1 kb or at least 10 kb, or at least 25 kb, or at least 50 kb, or at least 75 kb, or at least 100 kb, or at least 125 kb, or at least 150 kb, or at least 175 kb, or at least 200 kb, or at least 250 kb, or at least 300 kb, or at least 350 kb, or at least 400 kb, or at least 500 kb, or at least 600 kb, or at least 700 kb, or at least 800 kb, or at least 900 kb or at least 1 Mb, or 2 Mb, or 3 Mb, or 5 Mb, or 7 Mb, or 10 kb-1 Mb or 25 kb-1 Mb or 50 kb-1 Mb or 100 kb-1 Mb or 50 kb-2 Mb or 50 kb-3 Mb or 50 kb-5 Mb or 50 kb-7 Mb, or 30 kb-1 Mb or 30 kb-2 Mb or 30 kb-3 Mb or 30 kb-5 Mb or 30 kb-7 Mb or 100 kb-2 Mb or 100 kb-3 Mb or 100 kb-5 Mb or 100 kb-7 Mb.

In some aspects, the present disclosure provides a method of producing a polypeptide comprising: a) culturing cells comprising a vector comprising a *Vibrio* sp. chromosomal replication machinery and a nucleic acid encoding the polypeptide under conditions effective for the production of the polypeptide; and b) harvesting the polypeptide. In some examples, the replication machinery comprises SEQ ID NO: 1 or a variant thereof. In some examples, the vector further comprises an inducible promoter operably linked to a nucleic acid encoding the polypeptide. In some examples, the vector is capable of replication in *E. coli* or *S. cerevisiae*. In some examples, the cultured cells are *Vibrio* sp. bacterial cells. In some examples, the *Vibrio* sp. cells are any of those disclosed herein. In some examples the cultured cells or *Vibrio* sp. cells are naturally competent. In some examples, the cultured cells or *Vibrio* sp. cells are competent cells generated by any of the methods disclosed herein. In some examples, the vector is introduced into the cultured cells or *Vibrio* sp. cells by conjugation, chemical competence, natural competence, or electroporation. In some aspects, the vector further comprises a promoter, an origin of replication, an origin of transfer, a selectable marker, a counter-selectable marker, a reporter gene, a regulatory element, an enzyme gene, or a combination thereof. In some aspects, the selectable marker is an antibiotic resistance gene, a gene encoding a polypeptide conferring resistance to a toxin, an auxotrophic marker, and a combination thereof. In some aspects, the antibiotic resistance gene confers resistance to antibiotics selected from the group consisting of bleomycin, carbenicillin, chloramphenicol, gentamycin, glyphosate, hygromycin, kanamycin, neomycin, nourseothricin, phleomycin, puromycin, spectinomycin, streptomycin, or tetracyclin. In some examples, the reporter gene can be a fluorescent protein or beta-galactosidase. In some aspects, the enzyme is a recombinase, integrase, nuclease, recombineering enzymes, or polymerase. In some examples the recombinase is Cre recombinase. In some examples the integrase is PhiC31 or bxb1. In some examples the nuclease is a TypeII CRISPR Cas9 nuclease. In some examples, the polymerase is a Sp6, T3, or T7 RNA polymerase. In some aspects, the vector is compatible with *E. coli*, *V. natriegens*, and/or *S. cerevisiae*. In some aspects, the inducible promoter is induced by IPTG, arabinose, or temperature. In some aspects, the nucleic acid is at least 1 kb or at least 10 kb, or at least 25 kb, or at least 50 kb, or at least 75 kb, or at least 100 kb, or at least 125 kb, or at least 150 kb, or at least 175 kb, or at least 200 kb, or at least 250 kb, or at least 300 kb, or at least 350 kb, or at least 400 kb, or at least 500 kb, or at least 600 kb, or at least 700 kb, or at least 800 kb, or at least 900 kb or at least 1 Mb, or 2 Mb, or 3 Mb, or 5 Mb, or 7 Mb, or 10 kb-1 Mb or 25 kb-1 Mb or 50 kb-1 Mb or 100 kb-1 Mb or 50 kb-2 Mb or 50 kb-3 Mb or 50 kb-5 Mb or 50 kb-7 Mb, or 30 kb-1 Mb or 30 kb-2 Mb or 30 kb-3 Mb or 30 kb-5 Mb or 30 kb-7 Mb or 100 kb-2 Mb or 100 kb-3 Mb or 100 kb-5 Mb or 100 kb-7 Mb.

In some aspects, the present disclosure provides a method of producing a polypeptide comprising: a) contacting *Vibrio* sp. bacteria with a vector comprising a nucleic acid encoding the polypeptide and an inducible promoter, such that the vector is introduced into the bacteria; b) growing the bacteria under conditions effective for production of the polypeptide; and c) harvesting the polypeptide. In some examples, the vector comprises *Vibrio* sp. chromosomal replication machinery. In some examples, the replication machinery comprises SEQ ID NO: 1 or a variant thereof. In some examples, the vector is capable of replication in *E. coli* or *S. cerevisiae*. In some examples, the *Vibrio* sp. cells are any of those disclosed herein. In some examples, the *Vibrio* sp. bacteria are naturally competent. In some examples the *Vibrio* sp. bacteria are competent cells generated by any of the methods disclosed herein. In some examples, the vector is introduced into the *Vibrio* sp. bacteria by conjugation, chemical competence, natural competence, or electroporation. In some aspects, the vector further comprises a promoter, an origin of replication, an origin of transfer, a selectable marker, a counter-selectable marker, a reporter gene, a regulatory element, an enzyme gene, or a combination thereof. In some aspects, the selectable marker is an antibiotic resistance gene, a gene encoding a polypeptide conferring resistance to a toxin, an auxotrophic marker, or a combination thereof. In some aspects, the antibiotic resistance gene confers resistance to antibiotics which is bleomycin, carbenicillin, chloramphenicol, gentamycin, glyphosate, hygromycin, kanamycin, neomycin, nourseothricin, phleomycin, puromycin, spectinomycin, streptomycin, and tetracyclin. In some examples, the reporter gene can be a fluorescent protein or beta-galactosidase. In some aspects, the enzyme is a recombinase, integrase, nuclease, recombineering enzymes, or polymerase. In some examples the recombinase is Cre recombinase. In some examples, the integrase is PhiC31 or bxb1. In some examples the nuclease is a TypeII CRISPR Cas9 nuclease. In some examples, the polymerase is a Sp6, T3, or T7 RNA polymerase. In some aspects, the inducible promoter is induced by IPTG, arabinose, or temperature. In some examples, the nucleic acid is at least 1 kb or at least 10 kb, or at least 25 kb, or at least 50 kb, or at least 75 kb, or at least 100 kb, or at least 125 kb, or at least 150 kb, or at least 175 kb, or at least 200 kb, or at least 250 kb, or at least 300 kb, or at least 350 kb, or at least 400 kb, or at least 500 kb, or at least 600 kb, or at least 700 kb, or at least 800 kb, or at least 900 kb or at least 1 Mb, or 2 Mb, or 3 Mb, or 5 Mb, or 7 Mb, or 10 kb-1 Mb or 25 kb-1 Mb or 50 kb-1 Mb or 100 kb-1 Mb or 50 kb-2 Mb or 50 kb-3 Mb or 50 kb-5 Mb or 50 kb-7 Mb, or 30 kb-1 Mb or 30 kb-2 Mb or 30 kb-3 Mb or 30 kb-5 Mb or 30 kb-7 Mb or 100 kb-2 Mb or 100 kb-3 Mb or 100 kb-5 Mb or 100 kb-7 Mb. In some aspects, the *Vibrio* sp. cells comprise one or two altered, rearranged, or minimized chromosomes. In some examples, the essential elements from Chromosome II are alternatively located on Chromosome I. In some examples, the engineered bacteria contain a single chromosome comprising the essential features of Chromosome I and II. In some aspects, the growth doubling time of the cells is about 5 minutes to 15 minutes.

In some aspects, the present disclosure provides a method for cloning a nucleic acid comprising: a) introducing a heterologous nucleic acid into *Vibrio* sp. bacteria to create a transformed bacteria; b) culturing the cells under conditions for growth of the cells; c) isolation of a single transformed bacterial colony; d) growth of the bacterial colony; and e) extraction of nucleic acid. In some examples, the *Vibrio* sp. bacteria are those of any of those disclosed herein. In some examples the *Vibrio* sp. bacteria are naturally competent. In some examples, the *Vibrio* sp. bacteria are competent cells generated by any of the methods disclosed herein. In some examples, the introduction of the nucleic acid is performed by conjugation, chemical competence, natural competence, or electroporation. In some examples, the heterologous nucleic acid is a vector. In some examples, the vector comprises *Vibrio* sp. chromosomal replication machinery. In some examples, the replication machinery comprises SEQ ID NO:1 or a variant thereof. In some examples, the vector is capable of replication in *E. coli* or *S. cerevisiae*. In some aspects, the introduction of the nucleic acid is performed by conjugation, transformation, transduction, chemical competence, natural competence, or biolistics. In some aspects, the nucleic acid is at least 1 kb or at least 10 kb, or at least 25 kb, or at least 50 kb, or at least 75 kb, or at least 100 kb, or at least 125 kb, or at least 150 kb, or at least 175 kb, or at least 200 kb, or at least 250 kb, or at least 300 kb, or at least 350 kb, or at least 400 kb, or at least 500 kb, or at least 600 kb, or at least 700 kb, or at least 800 kb, or at least 900 kb or at least 1 Mb, or 2 Mb, or 3 Mb, or 5 Mb, or 7 Mb, or 10 kb-1 Mb or 25 kb-1 Mb or 50 kb-1 Mb or 100 kb-1 Mb or 50 kb-2 Mb or 50 kb-3 Mb or 50 kb-5 Mb or 50 kb-7 Mb, or 30 kb-1 Mb or 30 kb-2 Mb or 30 kb-3 Mb or 30 kb-5 Mb or 30 kb-7 Mb or 100 kb-2 Mb or 100 kb-3 Mb or 100 kb-5 Mb or 100 kb-7 Mb.

In some aspects, the present disclosure provides a kit for cloning DNA comprising: a) a vector comprising the *Vibrio* sp. chromosomal replication machinery; b) host cells compatible with the vector; c) buffer compatible with the host cells; and d) instructions for cloning the DNA. In some examples, the vector further comprises an inducible promoter. In some examples, the replication machinery comprises SEQ ID NO: 1 or a variant thereof. In some examples, the host cells are *Vibrio* sp. bacteria. In some examples the *Vibrio* sp. bacteria are any of those disclosed herein. In some examples, the host cells are *E. coli* or *S. cerevisiae*. In some aspects, the vector further comprises a promoter, an origin of replication, an origin of transfer, a selectable marker, a counter-selectable marker, a reporter gene, a regulatory element, an enzyme gene, or a combination thereof. In some aspects, the selectable marker is an antibiotic resistance gene, a gene encoding a polypeptide conferring resistance to a toxin, an auxotrophic marker, and a combination thereof. In some aspects, the antibiotic resistance gene confers resistance to antibiotics which is bleomycin, carbenicillin, chloramphenicol, gentamycin, glyphosate, hygromycin, kanamycin, neomycin, nourseothricin, phleomycin, puromycin, spectinomycin, streptomycin, and tetracyclin. In some examples, the reporter gene can be a fluorescent protein or beta-galactosidase. In some aspects, the enzyme is a recombinase, integrase, nuclease, recombineering enzymes, or polymerase. In some examples the recombinase is Cre recombinase. In some examples the integrase is PhiC31 or bxb1. In some examples the nuclease is a TypeII CRISPR Cas9 nuclease. In some examples, the polymerase is a Sp6, T3, or T7 RNA polymerase. In some aspects, the inducible promoter is induced by IPTG, arabinose, or temperature. In some aspects, the vector is alternatively or additionally compatible with *E. coli* and/or *S. cerevisiae*. In some aspects, the nucleic acid is at least 1 kb or at least 10 kb, or at least 25 kb, or at least 50 kb, or at least 75 kb, or at least 100 kb, or at least 125 kb, or at least 150 kb, or at least 175 kb, or at least 200 kb, or at least 250 kb, or at least 300 kb, or at least 350 kb, or at least 400 kb, or at least 500 kb, or at least 600 kb, or at least 700 kb, or at least 800 kb, or at least 900 kb or at least 1 Mb, or 2 Mb, or 3 Mb, or 5 Mb, or 7 Mb, or 10 kb-1 Mb or 25 kb-1 Mb or 50 kb-1 Mb or 100 kb-1 Mb or 50 kb-2 Mb or 50 kb-3 Mb or 50 kb-5 Mb or 50 kb-7 Mb, or 30 kb-1 Mb or 30 kb-2 Mb or 30 kb-3 Mb or 30 kb-5 Mb or 30 kb-7 Mb or 100 kb-2 Mb or 100 kb-3 Mb or 100 kb-5 Mb or 100 kb-7 Mb.

In some aspects, the present disclosure provides a kit comprising competent *Vibrio* sp. bacterial cells, which can be any disclosed herein. In some examples, the kit further comprises a compatible cloning vector.

Alternatively, or in addition to any of the forgoing embodiments, the disclosure provides the following embodiments:

Embodiment 1 is genetically engineered *Vibrio* sp. bacteria comprising one or more of the following:
 a) altered Chromosome I or Chromosome II,
 b) one or more non-essential genes removed from either Chromosome I or Chromosome II,
 c) one or more genes removed that encode an element selected from the group consisting of an endonuclease, exonuclease, methylase, nuclease, restriction enzyme, and restriction-modification system,
 d) at least one essential element from Chromosome II alternatively located on an engineered Chromosome I,
 e) at least one essential element from Chromosome II alternatively located on an engineered Chromosome I, wherein the essential element is a gene required for a function selected from the group consisting of metabolism, DNA replication, transcription, translation, cellular structure maintenance, and transport processes into and out of the cell,
 f) a single chromosome comprising essential elements from Chromosome I and Chromosome II such that the single chromosome is capable of supporting survival and replication of the bacterial under non-selective conditions,
 g) a heterologous nucleic acid sequence operably linked to a heterologous promoter,
 h) a heterologous nucleic acid encoding T7 RNA polymerase operably linked to an inducible promoter, or
 i) natural or lab-generated competence.

Embodiment 2 is a method of producing competent *Vibrio* sp. cells comprising a) growing *Vibrio* sp. cells in a growth-conducive medium, b) rendering said *Vibrio* sp. cells competent, and c) freezing the cells.

Embodiment 3 is a method of producing a biomolecule comprising a) contacting *Vibrio* sp. bacteria with a heterologous nucleic acid encoding the biomolecule, such that the heterologous nucleic acid is introduced into the bacteria, b) growing the bacteria in a growth-conducive medium wherein the heterologous nucleic acid is expressed, thereby producing the biomolecule, and c) isolating the biomolecule.

Embodiment 4 is a *Vibrio* sp. chromosomal replication machinery.

Embodiment 5 is the *Vibrio* sp. replication machinery comprising SEQ ID NO:1.

Embodiment 6 is a vector comprising Embodiment 4 or Embodiment 5 and optionally further comprising: a) a heterologous nucleic acid of interest optionally operably linked to an inducible promoter, b) replication machinery compatible with *E. coli* or *S. cerevisiae*.

Embodiment 7 is an expression system comprising the vector of Embodiment 6.

Embodiment 8 is a host cell comprising the vector of Embodiment 6, wherein the host cells are optionally any of those from Embodiment 1.

Embodiment 9 is a method of producing a polypeptide comprising a) culturing cells comprising a vector comprising a *Vibrio* sp. chromosomal replication machinery and a nucleic acid encoding the polypeptide under conditions effective for the production of the polypeptide; and b) harvesting the polypeptide.

Embodiment 10 is a method of producing a polypeptide comprising a) contacting *Vibrio* sp. bacteria with a vector comprising a nucleic acid encoding the polypeptide and an inducible promoter, such that the vector is introduced into the bacteria; b) growing the bacteria under conditions effective for production of the polypeptide; and c) harvesting the polypeptide.

Embodiment 11 is a method of cloning a nucleic acid comprising a) introducing a heterologous nucleic acid into *Vibrio* sp. bacteria to create a transformed bacteria; b) culturing the cells under conditions for growth of the cells; c) isolation of a single transformed bacterial colony; d) growth of the bacterial colony; and e) extraction of nucleic acid.

Embodiment 12 is the methods of any of Embodiments 2, 3, 9, 10, or 11 wherein the cells are those of Embodiment 1.

Embodiment 13 is the method of any of Embodiments 3, 9, 10, 11 wherein the vector is that of Embodiment 6 or the heterologous nucleic acid comprises Embodiment 4 or Embodiment 5.

Embodiment 14 is a kit for cloning DNA comprising a) a vector comprising the *Vibrio* sp. chromosomal replication machinery, b) host cells compatible with the vector, c) buffer compatible with the host cells, and d) instructions for cloning the DNA.

Embodiment 15 is the kit of Embodiment 14, wherein the vector is that of Embodiment 6.

Embodiment 16 is a kit comprising competent *Vibrio* sp. cells.

Embodiment 17 is the kit of Embodiment 14 or 16, wherein the cells are any of those of Embodiment 1.

Embodiment 18 is that of any of Embodiments 1-17, wherein *Vibrio* sp. is preferably *Vibrio natriegens*.

Vector

The present invention also discloses vectors operable in a *Vibrio* sp. The vectors can be a cloning, shuttle, or expression vectors (or combination thereof) depending on features included. Any of the vectors can have a sequence from *Vibrio* sp. chromosome II that comprises SEQ ID NO: 1 or a variation thereof. Any of the vectors disclosed herein can have a sequence of at least 2 kb or at least 3 kb or at least 4 kb or at least 5 kb of SEQ ID NO: 1, or a variant of any of them. The vector can also have an origin of replication operable in *Vibrio* sp. In some embodiments the origin of replication can be, for example, a p15a origin, or the origin of replication from plasmid pBR325 or SEQ ID NO: 2. But the person of ordinary skill with reference to this disclosure will realize other origins of replication that will find use in the invention. The vector can also have a selectable marker (e.g., an antibiotic resistance gene), and a heterologous nucleic acid of interest, for example a DNA sequence that encodes a heterologous protein or peptide, as described herein. The heterologous DNA sequence can be at least 5 kb or at least 10 kb or at least 25 kb or at least 50 kb or at least 100 kb or at least 125 kb or at least 150 kb or at least 175 kb or at least 200 kb or at least 250 kb, or at least 300 kb, or at least 350 kb, or at least 400 kb, or at least 500 kb, or at least 600 kb, or at least 700 kb, or at least 800 kb, or at least 900 kb or at least 1 Mb, or at least 2 Mb, or at least 3 Mb, or at least 5 Mb, or at least 7 Mb, or 10-100 kb or 10-150 kb or 10-200 kb or 10-500 kb or 10-700 kb or 10-1000 kb or 10 kb-2 Mb or 10 kb-5 Mb, or 10 kb-1 Mb or 25 kb-1 Mb or 50 kb-1 Mb or 100 kb-1 Mb or 50 kb-2 Mb or 50 kb-3 Mb or 50 kb-5 Mb or 50 kb-7 Mb, or 30 kb-1 Mb or 100 kb-1 Mb or 30 kb-2 Mb or 30 kb-3 Mb or 30 kb-5 Mb or 30 kb-7 Mb or 100 kb-2 Mb or 100 kb-3 Mb or 100 kb-5 Mb or 100 kb-7 Mb. or any length as disclosed herein. In some embodiments the heterologous sequence can encode a valuable protein or polypeptide, e.g., an enzyme, an immunoglobulin (e.g., trastuzumab, eculizumab, natalizumab, cetuximab, omalizumab, usteinumab, panitumumab, adalimumab, or a functional fragment of any of them), pro-insulin, or insulin.

The vector can also have an origin of replication operable in a second species of organism, which can be a non-*Vibrio* and non-*E. coli* organism. The second species can be another bacteria, for example, a *Bacillus* sp. The vector can therefore be a shuttle vector. The vector can also be operable in a yeast (e.g., % a yeast of the genus *Saccharomyces*, *S. cerevisiae*, *S. pombe*), in addition to the *Vibrio* sp. and the non-*Vibrio* and non-*E. coli* species of organism.

The vector can also have one or two or three or more than three operable promoters. Examples include, but are not limited to, the IPTG-inducible trc promoter, the arabinose-inducible araBAD or araC promoters, and the temperature-inducible lambda pR promoter modulated by the temperature-sensitive cI857 repressor. In one embodiment the heterologous DNA sequence is under the control of an inducible promoter. One or more promoters can regulate the heterologous DNA sequence.

The vectors of the invention can also have a transcriptional terminator, which can follow a heterologous DNA sequence that encodes a heterologous protein. One example of suitable transcriptional terminators includes the rrnB transcriptional termination sequence.

By "operable" is meant that the vector is effective for the expression of heterologous DNA sequences on the vector, or is effective for cloning of the vector and/or heterologous DNA sequences on the vector. When the heterologous DNA sequence encodes a heterologous protein, it is translated into a protein or polypeptide molecule and is produced as a functional protein or polypeptide in detectable amounts that are sufficient to provide the relevant function.

The vector can also comprise one or more selectable marker(s) (e.g., resistance gene(s)). The selectable marker(s) can be any suitable marker and examples include, but are not limited to, tetA/tetR, chloramphenicol, Trp, or any described herein. Selectable markers can be specific for the respective organisms when a shuttle vector is employed.

The vector can also encode a heterologous DNA sequence, which in some embodiments encodes a gene of interest (goi). The heterologous DNA sequence can encode a protein or polypeptide, which can be expressed from the shuttle vector to produce a functional protein or polypeptide. The functional protein or polypeptide can be any protein or polypeptide, for example an enzyme, an immunoglobulin, or any protein of interest, as described herein.

The vector can also be a shuttle vector and also have an origin of transfer (oriT) for conjugal transfer of the shuttle vector from the *Vibrio* sp. to the second species of organism. The transfer can be RP4-mediated conjugal transfer between the *Vibrio* sp. and the second species of organism. The vector can also have an autonomously replicating sequence (ARS) and a yeast centromere sequence (CEN) for replication in a yeast, such as described herein. The vector can also have a multiple cloning site (MCS) that has at least two restriction recognition sites such as, for example, sites for EcoRI, BamHI, or Pstl. But sites for any suitable restriction enzymes can be employed. The vector can also have a selection marker or resistance gene for a yeast, for example a Trp sequence or another suitable selection marker or resistance gene.

Any of the vectors described herein, including the shuttle vectors, can be low copy number vectors or plasmids, as maintained in *Vibrio* sp. organisms of the invention. In various embodiments the plasmids or (shuttle) vectors can have a copy number of less than 10 or less than 9 or less than 8 or less than 7 or less than 6 or less than 5. Any of the vectors of the invention can also have one or more or two or more lox sites (e.g., loxP sequence derived from bacteriophage P1). In any of the embodiments disclosed herein the *Vibrio* sp. organism can be a *Vibrio natriegens*. The invention also provides any *Vibrio* sp. organism described herein that comprises any vector or nucleic acid described herein.

*Vibrio* sp. Strain

The invention also provides a *Vibrio* sp. organism having specific characteristics. The *Vibrio* sp. organism can have a nucleic acid sequence encoding a T7 RNA polymerase that is regulated by an inducible promoter. The inducible promoter can be a lac promoter that is inducible with IPTG, for example the native lac promoter or the lacUV5 promoter. In other embodiments the inducible promoter can be the araBAD or araC promoter, which are inducible with arabinose. But in other embodiments the inducible promoter can be any suitable promoter inducible with a convenient metabolite. The *Vibrio* sp. organism can also have a lad repressor for repression of the inducible promoter. The organism can also have a nucleic acid sequence encoding a heterologous protein or peptide regulated by the inducible promoter and, optionally, a modified or weakened ribosome binding site. The sequence encoding the T7 RNA polymerase and inducible promoter can be integrated into Chromosome I or II of the organism, or present on a vector. FIG. 1 provides several examples of vectors that can be constructed according to the invention. The components of the vectors are not limited to the specific arrangements and can be used in any suitable combination. In some specific examples the *Vibrio* sp. can have a deletion of a nuclease, which can be an extracellular nuclease (e.g., a Dns deletion), a lacUV5 promoter regulating a T7 RNA polymerase gene with a lad repressor; and optionally can have SEQ ID NO: 8 or a variant thereof as a weakened rbs; all of which can be present on either Chromosome I or II, or on a vector within the organism. In another example the organism can use the araBAD and/or araC promoter 5' to the T7 RNA polymerase gene, and optionally the weakened ribosome binding site (e.g., SEQ ID NO: 8 or a variant thereof). These sequences also can be present on Chromosome I or II, or on a vector within the organism.

In any of the organisms or vectors a sequence encoding a heterologous protein or peptide can also contain a sequence that codes for a secretion signal for the protein or peptide, allowing the protein or peptide to be secreted from the cell after synthesis. The *Vibrio* sp. organism can be a *Vibrio natriegens*. Several examples of signal sequences operable in *Vibrio* sp. are provided as SEQ ID Nos: 11-25, or variants of any of them.

Ribosome Binding Site

Any of the *Vibrio* sp. organisms of the invention can also have a modified or weakened regulatory element, such as a ribosome binding site (rbs). The rbs can be present on Chromosome I or II of the organism. The organism can also have a nucleic acid sequence encoding a T7 RNA polymerase, and an optional inducible promoter. The rbs and inducible promoter (when present) can be present in front of (5' to) the T7 RNA polymerase gene. The rbs can be modified to be a weaker binder of ribosomes. Thus, when RNA is transcribed from the gene it is weakly bound by the modified rbs and therefore less protein is produced, and the rbs can therefore regulate expression of the gene through less translation of encoded protein or polypeptide. The modified or weakened rbs can reduce background levels of protein expressed from the regulated gene. Background levels of a protein is the level of protein expression that occurs when a native ribosome and inducible promoter are present, and the inducer is not present. The modified or weakened rbs can result in background protein expression from the regulated gene at least 25% less or at least 30% less or at least 40% less or at least 50% less than the regulated gene with a native rbs and the same inducible promoter. Background expression can be easily measured, for example using densitometry on a PAGE gel. The *Vibrio* sp. of the invention can also have at least one deletion of a nuclease, e.g., deletion of an extracellular nuclease such as a Dns deletion. In one embodiment the modified or weakened rbs can have the sequence of SEQ ID NO: 8 or a variant thereof. Variants of SEQ ID NO: 8 can be as described herein, and can have one or two or three or four or five substitution modifications, which can include nucleotide substitutions, deletions or insertions. The rbs can be modified or "weakened" so that ribosomes bind less strongly, and therefore less background gene expression occurs.

Thus, in one embodiment the invention provides a *Vibrio* sp. organism that has a genome having an exogenous gene for a T7 RNA polymerase that is regulated by an inducible promoter. The organism can also have a modified rbs that regulates expression of the T7 RNA polymerase gene by regulating translation of the RNA gene product. The organism can also have an exogenous gene that encodes a heterologous DNA sequence as disclosed herein (e.g., encodes a heterologous protein) that can be regulated by the inducible promoter. The exogenous gene for a T7 RNA polymerase and inducible promoter can be integrated into chromosome I or II of the organism. The heterologous DNA sequence can also be on chromosome I or II of the organism, or can be contained on a plasmid or other vector comprised in the organism. Any of the inducible promoters described herein can be utilized in the invention (e.g., araBAD, lac, lacUV5). The gene for a T7 RNA polymerase can also have a repressor sequence for repression of the inducible promoter (e.g., lad).

EXAMPLES

The disclosure in all its aspects is illustrated further in the following Examples. The Examples do not, however, limit the scope of the disclosure, which is defined by the appended claims.

Example 1

Growth of *V. natriegens* in a Range of Growth Media as Well as at Multiple Temperatures Growth of *V. natriegens* was examined on a number of different growth media and at multiple temperatures. A glycerol stock of *V. natriegens* was used to inoculate liquid cultures or was streaked out on agar plates. Liquid cultures were cultivated with agitation ranging from 175-220 RPM at the indicated temperatures. After overnight incubation, plates/cultures were examined for growth. Growth was defined as turbidity (in the case of liquid cultures) or visible colonies (in the case of agar plates).

Media compositions are as follows:

LB broth: 10.0 g/L Tryptone, 5.0 g/L Yeast Extract, 10.0 g/L NaCl.

LB broth+v2 salts: LB broth supplemented with additional salts (204 mM NaCl, 4.2 mM KCl, and 23.14 mM MgCl2).

LB broth+v2 salts+glucose: LB broth supplemented with additional salts (204 mM NaCl, 4.2 mM KCl, and 23.14 mM MgCl2)+0.2% glucose.

LB broth+v3 salts: LB broth supplemented with additional salts (475 mM NaCl, 9.7 mM KCl, and 54 mM MgCl2).

LB broth+v3 salts+glucose: LB broth supplemented with additional salts (475 mM NaCl, 9.7 mM KCl, and 54 mM MgCl2)+0.2% glucose.

LB agar: LB media+1.5% agar-agar.

LB agar+v2 salts: LB broth supplemented with additional salts (204 mM NaCl, 4.2 mM KCl, and 23.14 mM MgCl2)+1.5% agar-agar.

LB agar minus NaCl with 6% sucrose: 10.0 g/L Tryptone, 5.0 g/L Yeast Extract, 1.5% agar-agar, 6% sucrose.

Nutrient Broth+1.5% NaCl: 8 g/L Difco™ Nutrient Broth (Cat. No. 234000) supplemented with 1.5% NaCl.

Nutrient Agar+1.5% NaCl: 8 g/L Difco™ Nutrient Broth (Cat. No. 234000) supplemented with 1.5% NaCl and 1.5% agar-agar.

Brain Heart Infusion Broth: 37 g/L Teknova Brain Heart Infusion Broth Dry Media (Cat. No. B9500).

Brain Heart Infusion Broth+2% NaCl: 37 g/L Teknova Brain Heart Infusion Broth Dry Media (Cat. No. B9500)+20 g/L NaCl.

Brain Heart Infusion Broth+1.5% Instant Ocean: 37 g/L Teknova Brain Heart Infusion Broth Dry Media (Cat. No. B9500)+15 g/L Instant Ocean Sea Salt Mixture.

Brain Heart Infusion Broth+v2 salts: 37 g/L Teknova Brain Heart Infusion Broth Dry Media (Cat. No. B9500) supplemented with additional salts (204 mM NaCl, 4.2 mM KCl, and 23.14 mM MgCl2).

Brain Heart Infusion Broth+v3 salts: 37 g/L Teknova Brain Heart Infusion Broth Dry Media (Cat. No. B9500) supplemented with additional salts (475 mM NaCl, 9.7 mM KCl, and 54 mM MgCl2).

Brain Heart Infusion Agar+1.5% Instant Ocean: 52 g/L Difco™ Brain Heart Infusion Agar (Cat. No. 241830)+15 g/L Instant Ocean Sea Salt Mixture.

Brain Heart Infusion Agar: 37 g/L Teknova Brain Heart Infusion Broth Dry Media (Cat. No. B9500)+1.5% agar-agar.

Brain Heart Infusion Agar+v2 salts: 37 g/L Teknova Brain Heart Infusion Broth Dry Media (Cat. No. B9500)+1.5% agar-agar supplemented with additional salts (204 mM NaCl, 4.2 mM KCl, and 23.14 mM MgCl2).

M9 glucose media (500 mL): 1× M9 Salts, 0.4% glucose, 2 mM MgSO4, 0.1 mM CaCl$_2$.

M9 glucose agar: M9 glucose media supplemented with 1.5% agar-agar.

M9 glucose with 1% sucrose: 1×M9 Salts, 0.4% glucose, 2 mM MgSO4, 0.1 mM CaCl$_2$, 1% sucrose.

M9 glucose with 2% sucrose: 1×M9 Salts, 0.4% glucose, 2 mM MgSO4, 0.1 mM CaCl$_2$, 2% sucrose.

M9 glucose with 4% sucrose: 1×M9 Salts, 0.4% glucose, 2 mM MgSO4, 0.1 mM CaCl$_2$, 4% sucrose.

M9 1% sucrose: 1×M9 Salts, 2 mM MgSO4, 0.1 mM CaCl$_2$, 1% sucrose.

M9 2% sucrose: 1×M9 Salts, 2 mM MgSO4, 0.1 mM CaCl$_2$, 2% sucrose.

M9 4% sucrose: 1×M9 Salts, 2 mM MgSO4, 0.1 mM CaCl$_2$, 4% sucrose.

marine agar: 55.1 g/L Difco™ Marine Agar 2216 (Cat. No. 212185).

Bacto Heart Infusion Broth: 25 g/L Bacto™ Heart Infusion Broth (Cat. No. 238400).

SSG agar: 28 g/L Bacto™SOB Medium (Cat. No. 244310), 17% Fetal Bovine Serum, 1% glucose, 4 mL/L Phenol Red Solution (Sigma P0290).

2xYT+v2 salts+glucose+phosphate buffer: 2xYT media (16 g/L Tryptone, 10 g/L Yeast Extract, 5 g/L NaCl) is supplemented with v2 salts (204 mM NaCl, 4.2 mM KCl, 23.14 mM MgCl$_2$), 17.61 mM Na$_2$HPO$_4$, 0.2% glucose. pH is adjusted to 7.4.

Vegitone Infusion Broth+v2 salts: Vegitone Infusion Broth (Sigma Aldrich cat #41960) supplemented with v2 salts (204 mM NaCl, 4.2 mM KCl, 23.14 mM MgCl$_2$).

LB+v2 salts+glucose+phosphate buffer: LB media (10 g/L Tryptone, 5 g/L Yeast Extract, 10 g/L NaCl) is supplemented with v2 salts (204 mM NaCl, 4.2 mM KCl, 23.14 mM MgCl$_2$), 17.6 mM K$_2$HPO$_4$, 0.2% glucose. pH is adjusted to 7.0.

Results of the growth experiments are presented in Table 1:

TABLE 1

| Media | Format | 25° C. | 30° C. | 37° C. |
|---|---|---|---|---|
| LB broth | liquid culture | Growth | growth | no growth |
| LB broth + v2 salts | liquid culture | N/A | growth | growth |
| LB broth + v2 salts + glucose | liquid culture | N/A | growth | growth |
| LB broth + v3 salts | liquid culture | N/A | growth | growth |
| LB broth + v3 salts + glucose | liquid culture | N/A | growth | growth |
| LB agar | agar plate | Faint | growth | growth |
| LB agar + v2 salts | agar plate | N/A | growth | growth |
| LB agar minus NaCl with 6% sucrose | agar plate | N/A | no growth | no growth |
| Nutrient Broth + 1.5% NaCl | liquid culture | Growth | growth | no growth |
| Nutrient Agar + 1.5% NaCl | agar plate | slow growth | growth | attenuated growth |
| Brain Heart Infusion Broth | liquid culture | Growth | growth | attenuated growth |
| Brain Heart Infusion Broth + 2% NaCl | liquid culture | Growth | growth | growth |
| Brain Heart Infusion Broth + 1.5% Instant Ocean | liquid culture | Growth | growth | growth |
| Brain Heart Infusion Broth + v2 salts | liquid culture | N/A | growth | growth |
| Brain Heart Infusion Broth + v3 salts | liquid culture | N/A | growth | growth |
| Brain Heart Infusion Agar + 1.5% Instant Ocean | agar plate | slow growth | growth | growth |
| Brain Heart Infusion agar | agar plate | N/A | growth | N/A |
| Brain Heart Infusion agar + v2 salts | agar plate | Growth | growth | growth |
| M9 glucose media | liquid culture | slow growth | growth | N/A |
| M9 glucose agar | agar plate | slow growth | growth | slow growth |
| M9 glucose with 1% sucrose | agar plate | N/A | growth | growth |
| M9 glucose with 2% sucrose | agar plate | N/A | growth | growth |

TABLE 1-continued

| Media | Format | 25° C. | 30° C. | 37° C. |
|---|---|---|---|---|
| M9 glucose with 4% sucrose | agar plate | N/A | growth | growth |
| M9 1% sucrose | agar plate | N/A | growth | growth |
| M9 2% sucrose | agar plate | N/A | growth | growth |
| M9 4% sucrose | agar plate | N/A | growth | growth |
| marine agar | agar plate | slow growth | growth | growth |
| Bacto Heart Infusion Broth | liquid culture | N/A | growth | attenuated growth |
| SSG agar | agar plate | Growth | growth | growth |
| 2xYT + v2 salts + glucose + phosphate buffer | Liquid culture | N/A | growth | growth |
| Vegitone Infusion Broth + v2 salts | Liquid culture | N/A | growth | growth |
| LB + v2 salts + glucose + phosphate buffer | Liquid culture | N/A | growth | growth |

Example 2

Transformation of *V. natriegens* with Exogenous DNA Constructs Via Conjugation

This method was used to transfer a mobilizable plasmid from *E. coli* into *V. natriegens* where:

1) the plasmid was maintained as an episomal molecule in *V. natriegens*, or 2) where (with appropriate plasmid design) the plasmid integrated into the *V. natriegens* chromosome via a single or double-crossover integration event.

Donor Preparation: 10 mL of LB medium containing appropriate antibiotic was inoculated with *E. coli* donor strain (containing mobilizable plasmid of interest) and incubated overnight at 37° C. with agitation (200 RPM). Acceptable donor strains include, but are not limited to strain S17-1 λpir (containing the RP4 conjugation machinery integrated into the chromosome) or EPI300 cells harboring the pRL443 conjugative plasmid.

Recipient Preparation: 10 mL of LB medium was inoculated with *V. natriegens* recipient strain and incubated overnight at room temperature with agitation (175 RPM).

Conjugative Mating: Donor and recipient cultures were retrieved from incubators. 1 mL of each culture was separately centrifuged at 5000×g for 3 min in a 1.5 mL Eppendorf tube to pellet the cells. The supernatant was decanted and the cell pellets were each resuspended in 1 mL fresh LB medium. The wash (centrifugation/decanting/resuspension) was repeated for the donor strain to further reduce residual antibiotic carryover. Donor and recipient cultures were then mixed in multiple different ratios (e.g., 1:9, 1:4, 1:1, 4:1, 9:1 donor:recipient) in a total volume of 100 μL. The 100 μL of cells were spotted out as 10 μL spots on prewarmed LB plates, and incubated at 30° C. for 3-5 hours. Cells were washed from plate with 1 mL M9 glucose medium. Various volumes of cells (1 μL, 5 μL, 20 μL) were plated out on M9 glucose plates containing appropriate antibiotic and incubated overnight at 30° C. The *E. coli* donor strains mentioned above will not grow on the M9 medium utilized for this procedure (see recipe below). Individual *V. natriegens* colonies that grew on the M9 selective plate were then screened for successful conjugation event via standard methods.

M9 glucose medium (500 mL):
100 mL 5×M9 Salts
390 mL ddH2O
7.5 g agar-agar*
10 mL 20% glucose**
1 mL 1 M MgSO4**
50 μL 1 M CaCl2**
for solid media, add agar-agar
*added after autoclaving Example 3

Transformation of *V. natriegens* with Exogenous DNA Constructs Via Electroporation Preparation of Electrocompetent cells: 10 mL of Brain Heart Infusion Broth supplemented with supplemented salts (204 mM NaCl, 4.2 mM KCl, and 23.14 mM MgCl2) was inoculated with *Vibrio natriegens* and incubated overnight at 30° C. with agitation. On the following day, 250-500 mL of the same growth media was inoculated with the overnight culture at a dilution of 1:100 to 1:200 (overnight culture: fresh media). The culture was grown at 37° C. with shaking until an OD600 of 0.5. The culture was then split into two pre-chilled 250 mL centrifuge bottles which were then incubated on ice for 0-20 min. The cells were pelleted at 6500 RPM in a JA-14 centrifuge rotor for 20 min at 4° C. The supernatant was carefully decanted and the cell pellets were gently resuspended in 5-10 mL of electroporation buffer (680 mM sucrose, 7 mM $K_2HPO_4$, pH 7). The suspension was transferred to centrifuge tubes and the tube was filled to top (~35 mL) with additional electroporation buffer and inverted several times to mix. The cells were spun down at 6750 RPM for 15 min at 4° C. in a JA-17 rotor. The supernatant was decanted with pipette. The wash was repeated two times for a total of three washes. After the final wash, the cells were gently resuspended in residual electroporation buffer. The volume was adjusted with additional electroporation buffer to bring the final OD600 to 16. Cells were aliquoted into pre-chilled tubes and were stored at −80° C. until use.

Electroporation protocol: A vial of competent cells was retrieved from storage at −80° C. and allowed to thaw on ice. Plasmid DNA and electrocompetent cells were combined and gently mixed in a pre-chilled 1.5 mL microfuge tube. The cell/DNA suspension was transferred to a pre-chilled electroporation cuvette with a 0.1 cm gap size. Cells were electroporated with the following parameters: 700-900 V, 25 μF, 200Ω, 1 mm cuvette. Cells were immediately recovered in 500 μL recovery media (Brain Heart Infusion Broth supplemented with supplemented salts (204 mM NaCl, 4.2 mM KCl, 23.14 mM MgCl2, and 0-680 mM sucrose) and transferred to a 15 mL culture tube. The cells were recovered by incubating at 30-37° C. for 1-2 hours. Aliquots of the recovery media were plated out on pre-warmed agar plates containing appropriate antibiotic. Acceptable agar media include, but are not limited to: M9 glucose, Brain Heart Infusion Agar (with or without additional salt supplementation), and LB (with our without additional salt supplementation). The plates were incubated for several hours to overnight at 30-37° C. for colonies to appear.

Example 4

The Use of *V. natriegens* as a Host for Molecular Cloning in a Standard Cloning Pipeline Recombinant DNA fragments for assembly were derived from multiple sources including, but not limited to: digestion of existing recombinant DNA using nucleases (e.g., restriction enzymes, homing endonucleases, zinc-finger nucleases, TALENs, Cas9 nuclease with appropriate guide RNAs, etc.), PCR amplification, or de novo gene assembly from synthesized oligonucleotides.

In vitro assembly was carried out with any number of standard DNA construction techniques or commercially available kits including, but not limited to: ligation of DNA fragments using a suitable DNA ligase and Gibson Assembly. Alternatively, in vivo assembly can be performed in a compatible host cell, such as, for example, *E. coli* or *S. cerevisiae* followed by isolated of the assembled product.

Once in vitro or in vivo assembly and isolation, if appropriate, is complete, *V. natriegens* competent cells that have been prepared according to the conjugation or electroporation protocol were transformed according to the appropriate protocol in either Example 2 or Example 3. Cells were plated on agar plates containing the appropriate antibiotic and incubated for several hours to overnight at 30-37° C. for colonies to appear.

Colonies isolated from agar plates containing appropriate antibiotics were used to inoculate growth media containing the same antibiotic. Cells were grown for ~3 hours to overnight at 30-37° C. Cells were harvested by centrifugation, and DNA was then extracted via standard methods (e.g., alkaline lysis techniques) or commercially available kits (e.g., QIAspin Miniprep Kit from Qiagen). Extracted DNA was analyzed by standard methods.

Example 5

The Use of *V. natriegens* as a Host for Inducible Protein Expression

A series of plasmids was designed for inducible protein expression of green fluorescent protein (GFP). The plasmids were designed to contain:
1) one of three promoters (the IPTG-inducible trc promoter, arabinose-inducible araBAD promoter, or the temperature inducible λ pR promoter modulated by the temperature-sensitive cI857 repressor.
2) one of two origins of replication (the p15a origin of replication or the origin from plasmid pBR325).
3) a green fluorescent protein (GFP) under the control of the inducible promoter to monitor expressions.
4) a transcriptional terminator following GFP (rrnB transcriptional termination sequence).
5) a chloramphenicol resistance gene for antibiotic selection.

The functional elements and their source plasmids are listed in Table 2:

TABLE 2

| Element | Source Plasmid |
| --- | --- |
| trc promoter | pTrcHisA |
| araBAD promoter | pKD46 |
| λ pR promoter/temperature-sensitive cI857 repressor | 705-cre |
| p15a origin4 | pACYC184 |
| pBR325 origin | pBR325 |
| GFP gene | synthesized from oligos |
| rrnB transcriptional termination sequence | pTrcHisA |
| chloramphenical acyl transferase gene | pCC1BAC |

The maps for the six plasmids are shown in FIG. 1. The plasmids were assembled in vitro using Gibson Assembly and electroporated into *V. natriegens* following the protocols described in Example 4.

Figure 2:
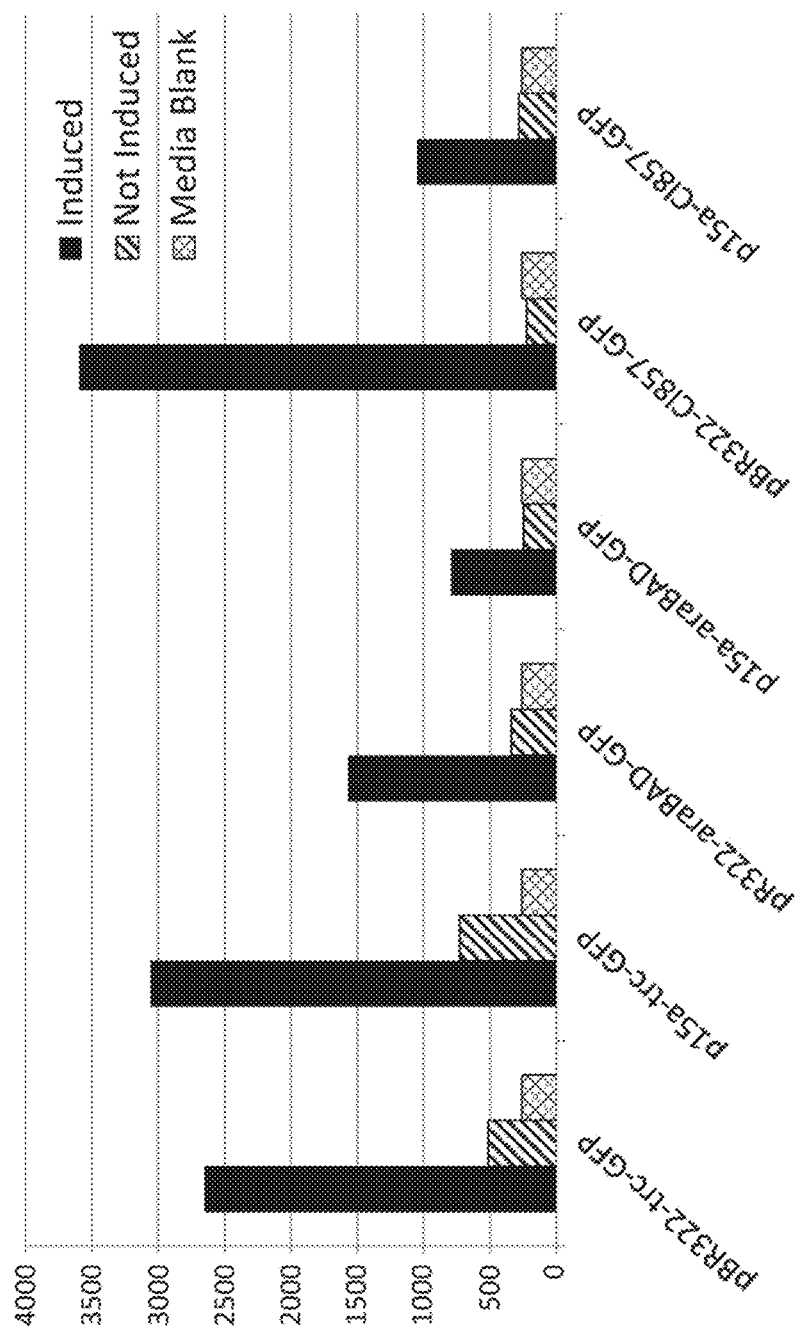
FIG. 2 shows GFP fluorescence normalized to OD600 for induced and non-induced cultures harboring each of the six expression plasmids.

Cultures of individual transformed colonies were grown overnight in LB media (10.0 g/L Tryptone, 5.0 g/L Yeast Extract, 10.0 g/L NaCl) supplemented with additional salts (204 mM NaCl, 4.2 mM KCl, and 23.14 mM MgCl2) at 30° C. with agitation at 200 RPM. On the following day the cultures were used to inoculate fresh salt-supplemented LB media at a ratio of 1:100 overnight culture:fresh media. The cultures were grown at 30° C. with agitation until an OD600 of 0.5. Cultures were then induced with appropriate inducer (0.2% arabinose, 1 mM IPTG, or shifting temperature to 42° C., for the araBAD, trc, and pR promoters respectively). After ~4 hours, the OD600 and GFP fluorescence (excitation 480 nm/emission 510 nm) were measured. FIG. 2 shows GFP fluorescence normalized to OD600 for induced and non-induced cultures harboring each of the six expression plasmids. The data demonstrates the functionality of these inducible promoter systems in this species.

Figure 3:
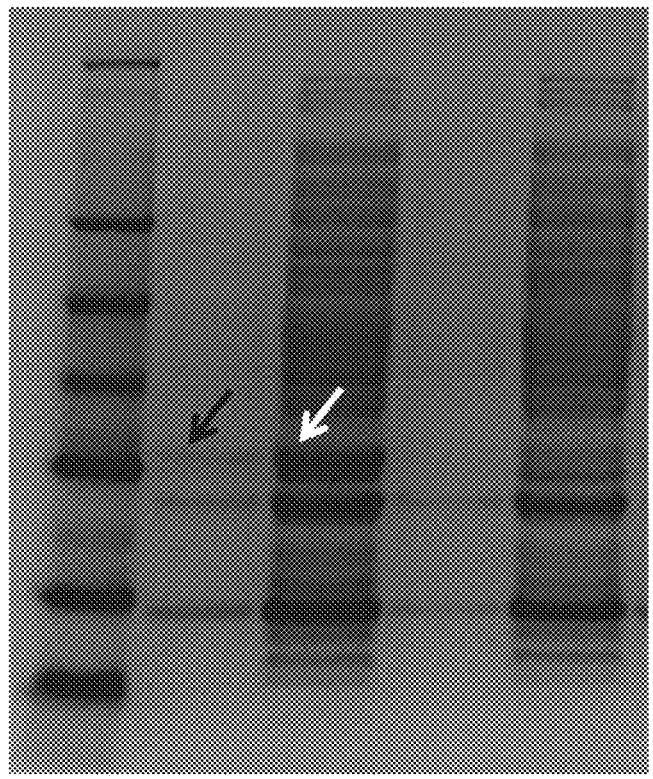
FIG. 3 shows the presence of GFP from cultures of *V. natriegens* harboring pBR322-trc-GFP. Lane 1: SeeBlue Plus2 Protein Standard; Lane 2: 1 μL *V. natriegens* pBR322-trc-GFP lysate from IPTG-induced culture; Lane 3: 10 μL *V. natriegens* pBR322-trc-GFP lysate from IPTG-induced culture; Lane 4: 1 μL *V. natriegens* pBR322-trc-GFP lysate from non-induced culture and Lane 5: 10 μL *V. natriegens* pBR322-trc-GFP lysate from non-induced culture. Arrows indicate GFP.

For further analysis, cultures of *V. natriegens* harboring pBR322-trc-GFP (induced and non-induced) were collected via centrifugation, resuspended in lysis buffer (20 mM Tris pH 8, 2 mM MgCl$_2$), lysed via sonication, clarified via centrifugation, and run on a 4-12% 10-well Bolt® Bis-Tris gel (Life Technologies®) with MES running buffer, which was subsequently stained with SimplyBlue™ safe stain (Life Technologies®). In FIG. 3, Lane 1: SeeBlue Plus2 Protein Standard (Life Technologies™); Lane 2: 1 µL *V. natriegens* pBR322-trc-GFP lysate from IPTG-induced culture; Lane 3: 10 µL *V. natriegens* pBR322-trc-GFP lysate from IPTG-induced culture; Lane 4: 1 µL *V. natriegens* pBR322-trc-GFP lysate from non-induced culture and Lane 5: 10 µL *V. natriegens* pBR322-trc-GFP lysate from non-induced culture. The GFP protein can be seen in the lanes corresponding to the induced culture, but is present at much lower levels in the non-induced culture.

Example 6

The Use of the "Free" ChrII as a Cloning/Shuttle Vector in Non-*Vibrio* Species (e.g., *E. coli*)

The replication machinery of *V. natriegens* chrII comprises SEQ ID NO: 1.

The vector pVnatoriCII was prepared by assembling the following DNA regions from the following sources:
1) *V. natriegens* chrII sequence (amplified from *V. natriegens* genomic DNA) (SEQ ID NO: 1);
2) R6Kγ origin of replication (amplified from plasmid pR6Kan from Epicentre®)(SEQ ID NO: 2); and
3) tetA/tetR resistance genes+RP4 oriT (amplified from plasmid pJB3Tc20) (SEQ ID NO: 3).

Figure 4:
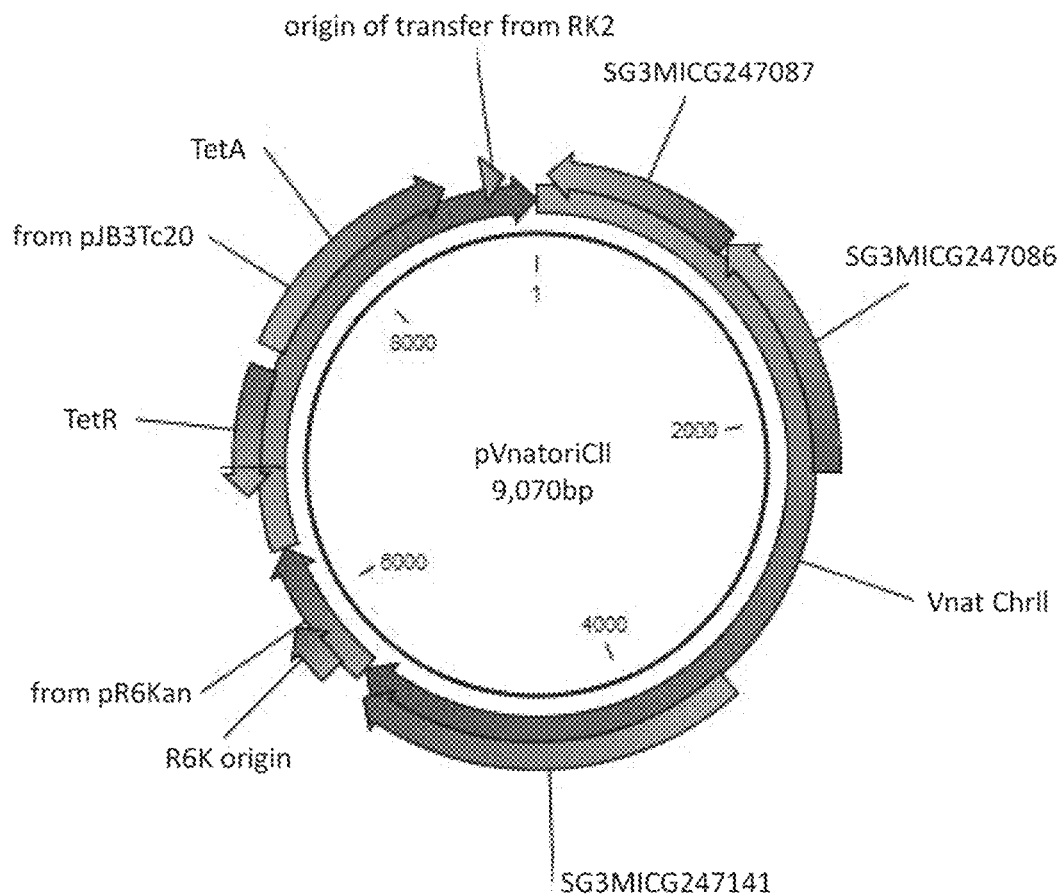
FIG. 4 shows a plasmid comprising the sequence from *V. natriegens* chrII, the R6Kγ origin of replication and the tetA/tetR resistance genes along with the RP4 oriT region of plasmid pJB3Tc20.

The PCR primers were designed to generate sufficient homology overlaps between the PCR products to facilitate vector construction via Gibson Assembly to generate the plasmid shown in FIG. 4.

The plasmid comprises the sequence from *V. natriegens* chrII, the R6Kγ origin of replication (without the pir gene encoding the Π (pi) protein necessary for plasmid replication) and the tetA/tetR resistance genes (as a selective marker) along with the RP4 oriT region (to facilitate mobilization of plasmid via conjugation) of plasmid pJB3Tc20 (NCBI genbank U75324).

The vector was assembled in vitro according to standard methods and was transformed into EC100D pir-116 *E. coli* cells from Epicentre® via electroporation. These cells contain the pir gene encoding the Π (pi) protein necessary for replication of plasmids containing the R6Kγ origin of replication. Because the designed plasmid contains the R6Kγ origin, the plasmid will be able to replicate in this strain regardless of the functionality of the *V. natriegens* chrII machinery in *E. coli*. Cells were plated out on LB agar plates containing 10 μg/mL tetracycline. Individual colonies were grown up in LB media containing 10 μg/mL tetracycline, and DNA was recovered using the Qiaprep Spin Miniprep Kit from Qiagen®. Proper vector assembly was verified via restriction digestion analysis. Plasmids with the correct restriction pattern were then electroporated into EPI300 *E. coli* cells from Epicentre® via electroporation. Because EPI300 cells do not contain the pir gene encoding then protein necessary for replication of plasmids containing the R6Kγ origin of replication, the only way this plasmid will replicate is if the *V. natriegens* chrII replication machinery is able to support plasmid replication in *E. coli*. The transformation of EPI300 cells with pVnatoriCII resulted in tetracycline resistant colonies, indicating the plasmid successfully replicated in this strain.

Conjugation Mediated Transfer of pVnatoriCII from *E. coli* to *V. natriegens*

The plasmid was also transferred to *V. natriegens* via conjugation from *E. coli* strain 517-1 λpir following the conjugation protocol described in Example 2, giving rise to tetracycline-resistant *V. natriegens* colonies.

Cloning Large DNAs into pVnatoriCII

Figure 5:
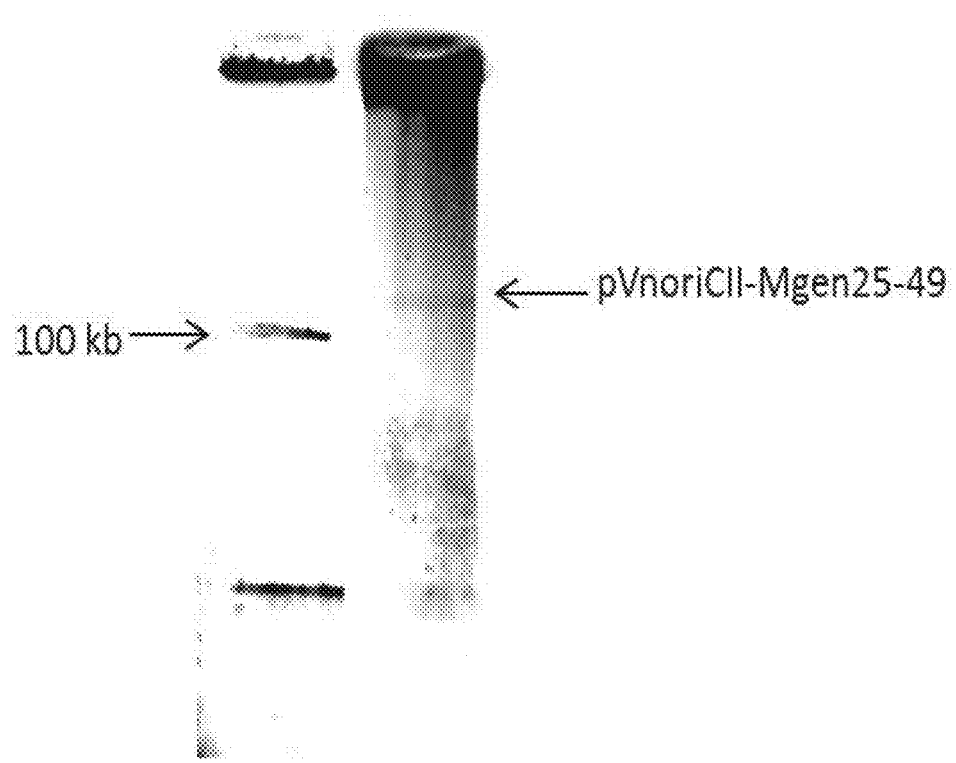
FIG. 5 shows plasmid pVnoriCII-Mgen25-49 run on an agarose gel.

To assess the utility of pVnatoriCII for harboring large DNA molecules in *E. coli*, we cloned ~135 kb of sequence from the *Mycoplasma genitalium* genome into the plasmid (by replacing the R6Kγ origin with *M. genitalium* sequence) to generate plasmid pVnoriCII-Mgen25-49. A plasmid of >100 kb could be recovered from EPI300 cells harboring the plasmid as can be seen by running supercoiled plasmid DNA on an agarose gel (FIG. 5).

Sequencing of the plasmid (Illumina® MiSeq) confirmed the expected sequence, demonstrating that pVnoriCII can be used to clone >100 kb of exogenous DNA in *E. coli*.

Improved *E. coli*/*V. natriegens* Shuttle Vector

In order to improve upon the design of pVnatoriCII, a second *V. natriegens* chrII plasmid was designed (known as pVnatCII-YACTRP-copycontrol) by leveraging features from the following plasmids:

From pVnoriCII:
oriT for RP4-mediated conjugal transfer.
*V. natriegens* chrII origin of replication for low copy replication of plasmid.

From pCC1BAC™ from Epicentre®:
oriV for use with *E. coli* strains containing the trfA gene product under an inducible promoter (e.g., EPI300 cells from Epicentre®).
chloramphenicol resistance marker for antibiotic selection.
Multiple Cloning Site (MCS) with convenient restriction enzyme cut sites.
loxP site for recombination via Cre-recombinase.

In addition, the plasmid also contains:
ARS/CEN for stabile replication in *Saccharomyces cerevisiae*.
Trp gene for selection in a Trp auxotroph of *Saccharomyces cerevisiae*.

Figure 6:
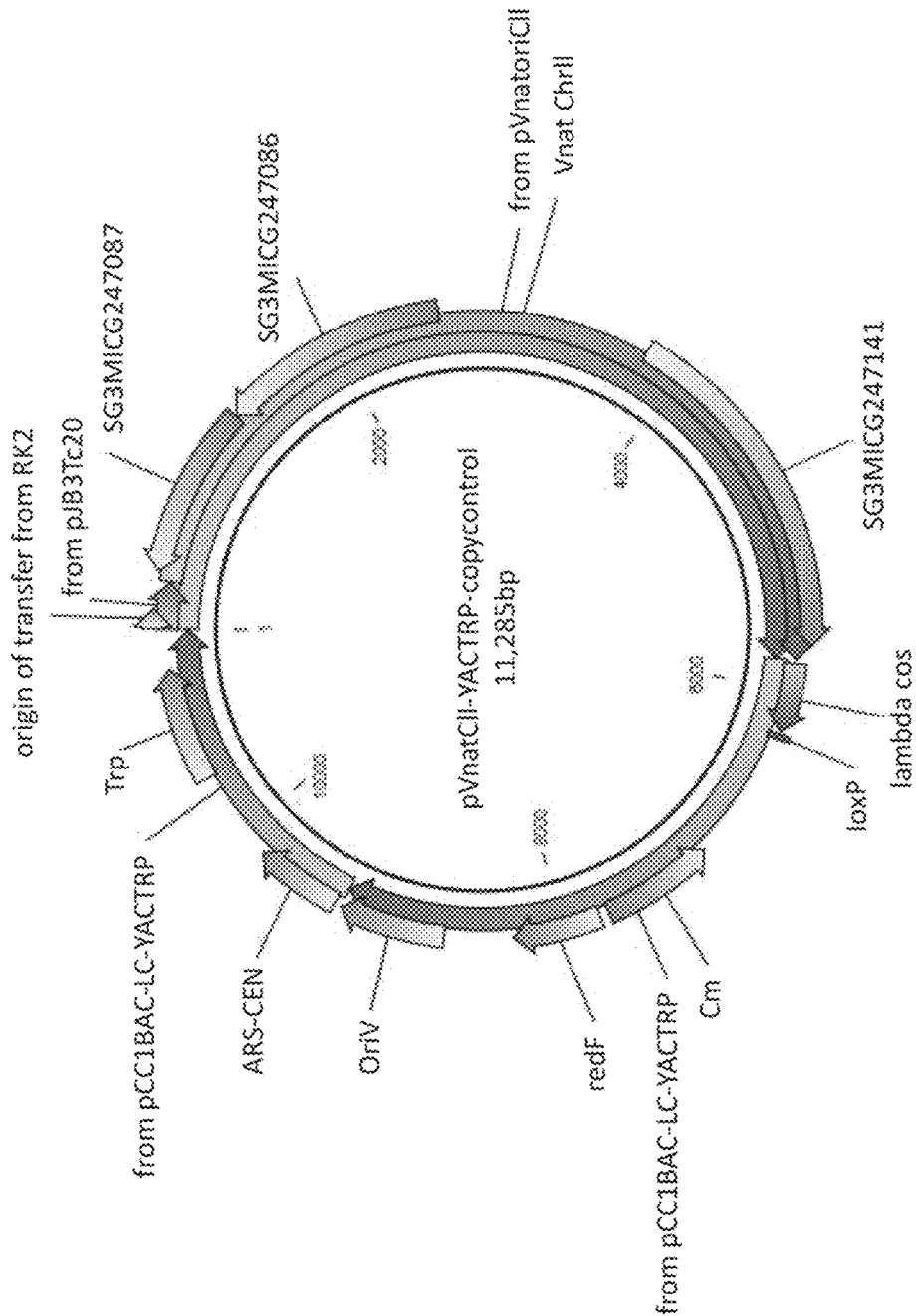
FIG. 6 shows the vector map and sequence of pVnatCII-YACTRP-copy control.

The vector map and sequence of pVnatCII-YACTRP-copy control are shown in FIG. 6.

The plasmid comprises the following sequence: pVnatCII-YACTRP-copycontrol (SEQ ID NO: 4).

The plasmid pVnatCII-YACTRP-copycontrol was replicated in *E. coli* at low copy, and the copy number was also increased by supplementing the trfA gene product in trans (e.g., via EPI300 cells, which contain an inducible copy of trfA on the chromosome).

The plasmid pVnatCII-YACTRP-copycontrol was also introduced into *E. coli*, *V. natriegens*, and *Saccharomyces cerevisiae* via transformation and maintained under the appropriate selection.

Example 7

Use of a Suicide Plasmid System to Engineer the Genome of *V. natriegens*

We have developed a suicide plasmid system that can be used to remove endogenous DNA sequence or introduce exogenous DNA into the chromosome of *V natriegens*. The plasmid was constructed with the following DNA elements in the following order:
a) 500 bp of chromosomal sequence directly upstream of the location where an insertion/deletion event was desired to start;
b) A "knock-out/knock-in" cassette containing an antibiotic resistance marker (e.g., Cm antibiotic resistance marker (from pACYC184)) flanked by lox66 and lox71 sites. In addition, if exogenous DNA was to be added into the chromosome, that DNA was contained in this fragment after the lox-bounded Cm marker;
c) 500 bp of chromosomal sequence directly downstream of the location where an insertion/deletion event was desired to end;
d) the R6K origin of replication from pR6Kan (Epicentre®);
e) the RK2 origin of transfer (oriT) from pRL443; and
f) the ccdB toxin under control of the arabinose-inducible araBAD promoter (SEQ ID NO:5) (the araC gene and araBAD promoter are from plasmid pKD46).

Because the plasmid lacks the Π (pi) replication protein necessary to initiate replication from the R6K origin, the plasmid will only replicate when Π (pi) is supplied in trans (e.g., from the EC100D pir-116 strain from EPICENTRE®). The plasmid was introduced into an *E. coli* strain capable of supplying the Π (pi) protein in trans that also contained the conjugation machinery from plasmid RP4 (we use strain S17-1 λpir). The strain was then mated with *V. natriegens* (following the conjugation protocol described in Example 2) to allow mobilization of the plasmid from the donor *E. coli* strain to V *natriegens*. Because the plasmid is incapable of replicating in *V. natriegens*, the only way that antibiotic-resistant clones were isolated was if the plasmid integrated into the chromosome via the regions of the plasmid that are homologous to the *V. natriegens* genome. Double-crossover integration events were selected for by growing the strain in media (e.g., LB) containing 0.2-0.4% L-arabinose as well as an antibiotic (the antibiotic which is contained in the cassette flanked by homology to the *V. natriegens* genome). The presence of arabinose induced the araBAD promoter, thereby producing the ccdB toxin and removing cells that had not undergone integration via double-crossover recombination from the population (the toxin is not present in cells that have undergone double-crossover recombination). Surviving clones were screened for successful integration via standard methods.

Use of the System to Remove Endogenous DNA Sequence from the Chromosome

Figure 7:
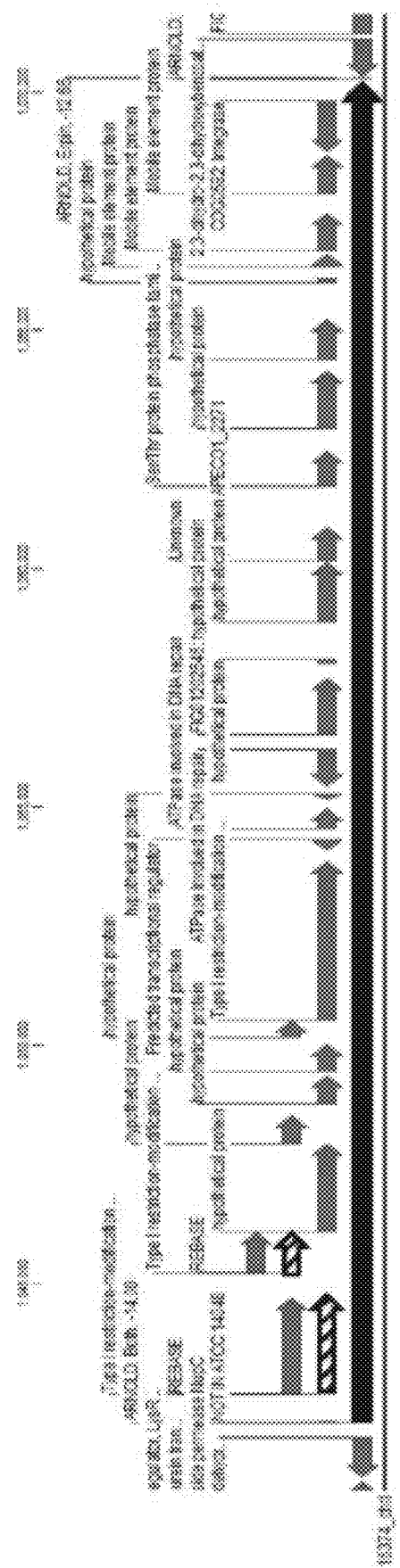
FIG. 7 shows a region of *V. natriegens* strain CCUG16374 chromosome I containing a 28 kb genetic island demarcated by the black arrow. Genes are depicted with grey arrows. The enzymes involved in the putative restriction-modification system are demarcated by striped arrows.

In this embodiment, the "knock-out/knock-in" cassette was composed simply of an antibiotic resistance gene flanked by lox sites oriented in the same direction (e.g., the orthogonal and uni-directional lox66/lox71 pair). The "knock-out/knock-in" cassette was flanked on either side by 500-750 bp of *V. natriegens* chromosomal sequence that was chosen such that the antibiotic cassette was flanked by 500-750 bp of sequence immediately upstream of the start point of the desired deletion, and 500-750 bp immediately downstream of the end point for the desired deletion. Upon successful integration via double-crossover recombination, the region of the genome to be deleted was replaced by the antibiotic cassette flanked by lox sites. The antibiotic cassette was later removed from the genome via the expression of Cre recombinase, which recombined the lox sites, thus looping the antibiotic cassette out of the chromosome (see discussion of engineering with Cre recombinase in Example 8). In some examples, we used this technique to remove the ORF for the Dns exonuclease. In another example, we used this technique to remove a 28 kb region of Chromosome I from strain CCUG 16374 harboring a putative restriction-modification system (FIG. 7).

Use of the System to Introduce Exogenous DNA into the Chromosome

In this embodiment, the "knock-out/knock-in" cassette was composed of an antibiotic resistance gene (which may or may not be flanked by lox sites oriented in the same direction) as well as additional exogenous DNA to be added into the chromosome. The "knock-out/knock-in" cassette was flanked on either side by 500 bp of *V. natriegens* chromosomal sequence that was chosen such that the "knock-in" cassette is flanked by 500 bp of sequence immediately upstream of the start point of the desired insertion, and 500 bp immediately downstream of the end point for the desired insertion. Upon successful integration via double-crossover recombination, the exogenous DNA along with the antibiotic marker was inserted into the genome at the desired location. If the antibiotic cassette is flanked by lox sites, it was later removed from the genome via the expression of Cre recombinase, which recombined the lox sites, looping the antibiotic cassette out of the chromosome (see discussion of engineering with Cre recombinase in Example 8). In some examples, we used this technique to introduce an inducible T7 RNA polymerase gene (SEQ ID NO:7) into the genome (see discussion of protein expression via an inducible T7 RNA polymerase in Example 9).

Example 8

Use of Site-Specific Recombinases to Engineer the Genome of *V. natriegens*

The use of site specific recombinases along with their target sequences was used to carry out insertions and deletions in the chromosome of *V. natriegens* and could additionally be used to carry out inversions. We have demonstrated the use of the Cre-lox system to remove sequences present in the chromosome that have been flanked by lox sites.

In Example 7 (Use of a suicide plasmid system to engineer the genome of *V. natriegens*), a chloramphenicol marker flanked by lox66 and lox71 sites (that are oriented in the same direction) was introduced into the chromosome in such a manner as to replace the entire ORF for the Dns nuclease. By expressing Cre recombinase, recombination between the lox sites resulted in the removal of the antibiotic marker from the chromosome, leaving behind a native loxP site (thus allowing us to recycle our antibiotic marker). To this end we designed the plasmid pACYCtetoriTCre, which contains:

a) the p15a origin of replication from plasmid pACYC184;
b) the tetracycline resistance cassette from plasmid pJB3Tc20;
c) the RK2 the RK2 origin of transfer (oriT) from pRL443;
d) the temperature-inducible Cre expression cassette from plasmid 705-Cre (from Gene Bridges GmbH).

Introduction of the plasmid into the strain (carrying the lox site flanked modification) via electroporation, followed by incubation at 37° C. (to induce expression of Cre recombinase) resulted in the desired phenotype (i.e., a strain that had undergone Cre-mediated recombination to remove the antibiotic marker).

In addition to carrying out deletions, this system can be used to introduce novel DNA into a chromosome (via recombination with an exogenous circular DNA containing a lox site) and additionally or alternatively to invert regions of the chromosome (with proper orientation of the lox site).

Analogous systems are envisioned which rely on other site-specific recombinases or integrases (e.g., phiC31 integrase, bxb1 integrase, etc.).

Example 9

The Introduction of an Inducible T7 RNA Polymerase Gene into the *V. natriegens* Chromosome and its Use in Recombinant Protein Expression Using the suicide plasmid system described in Example 7, we have introduced the gene for T7 RNA polymerase (SEQ ID NO:7) under the control of either:

a) The arabinose-inducible araBAD promoter (SEQ ID NO:5) and araC regulator protein (from *E. coli*); or
b) The IPTG-inducible lac operon regulatory elements and lad regulator protein (SEQ ID NO:6) (from *E. coli*) into the chromosome of *V. natriegens*. This system allows for inducible, robust protein expression from a plasmid-borne gene under control of the T7 promoter. We denote the arabinose-inducible strain araBAD-T7, and the IPTG-inducible strain lacI-T7.

In conjunction with the strain, we designed a plasmid known as pET325Cm-YGFP which is based off of plasmid pET28a (Novagen) and contains the YGFP fluorescent protein under the T7 promoter. The vector differs from pET28a primarily in that the Cm marker from pACYC184 is used instead of the kanamycin resistance gene.

Figure 8A:
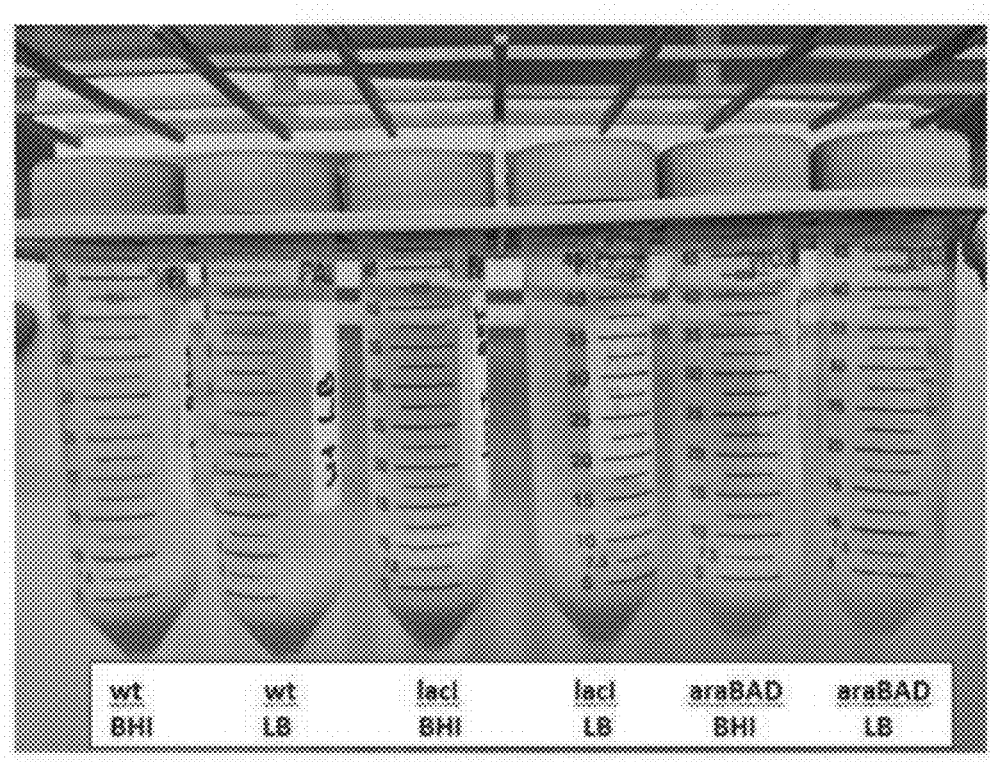
FIGS. 8A-8B show *V. natriegens* cultures comprising T7 RNA polymerase operably linked to the indicated inducible promoter and a GFP cassette operably linked to a T7 promoter in the indicated media.
Figure 8B:
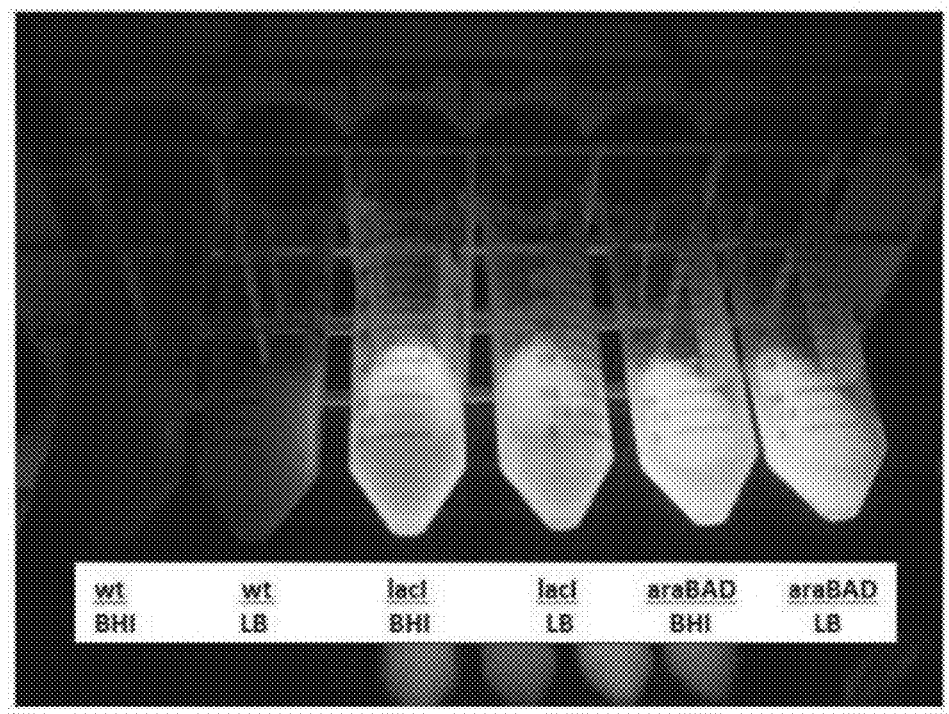
Figure 9:
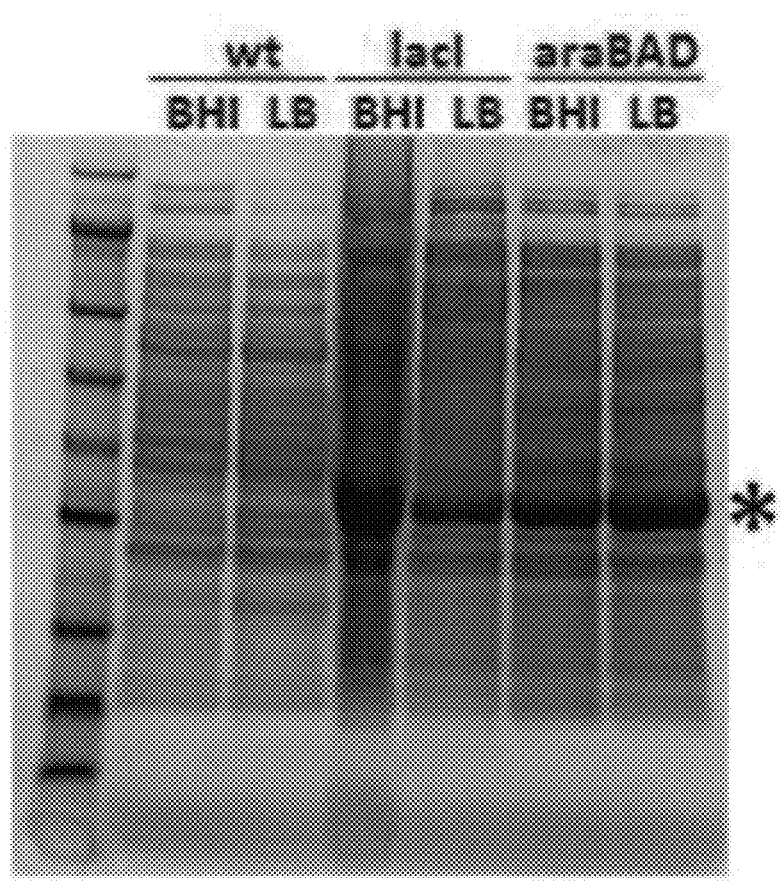
FIG. 9 shows a stained gel of bacterial lysates from wild type (two left cultures) and the indicated four strains expressing inducible GFP. The dark band demarcated with the asterisk is the GFP protein, which is only present in the engineered strains (BHI lad, LB lad, BHI araBAD, LB araBD), and not wild type (wt) cultures.

The plasmid was introduced into *V. natriegens* araBAD-T7 and lacI-T7 strains as well as the wild type (wt) parental strain via electroporation (described in Example 3). Strains harboring the plasmid were grown up overnight in Brain Heart Infusion Broth+v2 salts with 12.5 ug/mL chloramphenicol at 30° C. with shaking at 200 RPM (v2 salts means the media was supplemented with additional salts at the following concentrations: 204 mM NaCl, 4.2 mM KCl, 23.14 mM MgCl$_2$). The next day 50 mL of either LB+v2 salt media or BHI+v2 salt media with 15 ug/mL chloramphenicol in a 250 mL baffled flask was inoculated with 1/100th volume of overnight culture and incubated at 30° C. When the OD600 was between 0.6 and 0.9 the cultures were induced with 1 mM IPTG (wt and lacI-t7 strains) or 1 mM IPTG+0.2% arabinose (araBAD-T7 strain). At 6.5 hrs post induction, the cultures were retrieved and the cells were harvested via centrifugation. The pellets were suspended in buffer (50 mM Tris pH 7.4, 300 mM NaCl, 5 mM Imidazole) to a total volume of about 7 mL. The cells were then imaged under white light (FIG. 8A), or under a blue light transilluminator with orange filter (FIG. 8B). As can be seen in FIG. 8, the wt strain, even when induced did not make any protein. Both versions of the T7 expression system (araBAD-T7 and lacI-T7) expressed YGFP. The pellets were lysed via sonication, clarified via centrifugation, and the lysate was analyzed by SDS-PAGE (FIG. 9). The overexpressed YGFP construct is apparent in the lacI-T7 and araBAD-T7 strains.

Many configurations of this system are envisioned. In some embodiments the RNA polymerase could reside on a plasmid and the gene that is to be overexpressed could be cloned into any number of vectors under control of the T7 promoter.

Analogous expression strains could be generated using other configurations of chromosomally integrated or plasmid-borne inducible RNA polymerases, relying on other RNA polymerases (e.g., SP6 RNA polymerase, etc.) or inducible promoters (e.g., other chemically inducible promoters, temperature inducible promoters, etc.).

Example 10

Secretion of Recombinant Proteins from *Vibrio* Sp.

This examples shows the secretion of recombinant proteins directly into the growth media.

Figure 10:
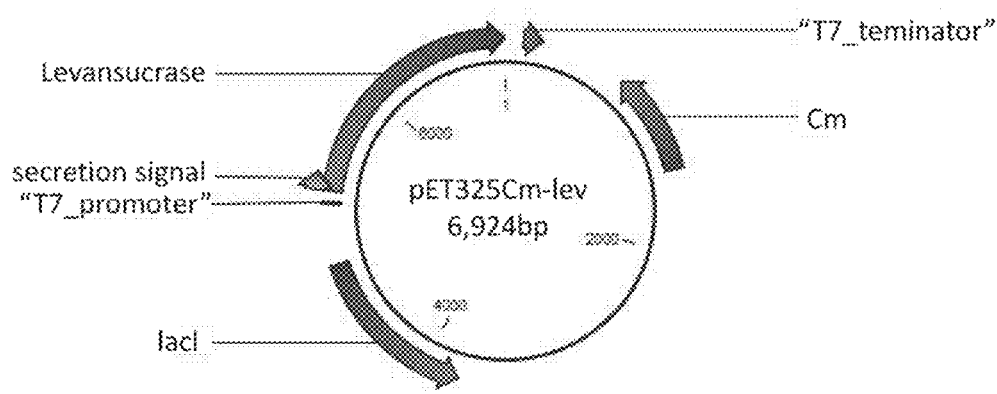
FIG. 10 is an illustration of the levansucrase expression vector used in conjunction with a *V. natriegens* strain harboring an inducible T7 RNA polymerase gene.
Figure 11:
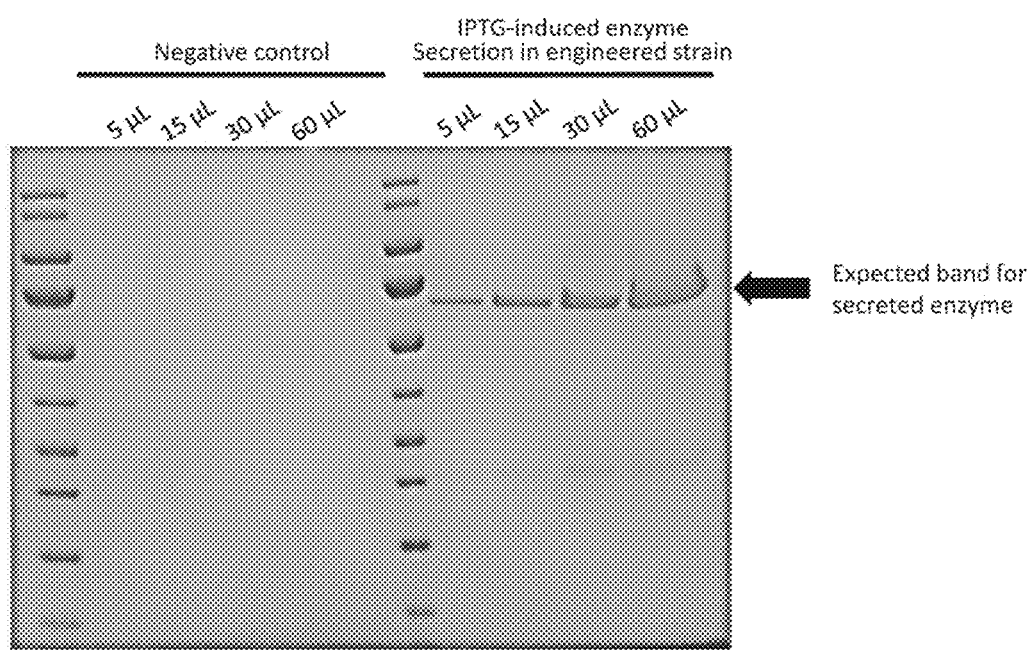
FIG. 11 shows a stained gel with various volumes of clarified growth media following a 5-hour fermentation in a minimal media with 1 mM IPTG of either *V. natriegens* T7 expression strain by itself (negative control) or the same organism but with the levansucrase expression plasmid, demonstrating IPTG-induced enzyme secretion. The plasmid is shown in FIG. 10.

A *V. natriegens* was engineered by replacing the open reading frame (ORF) for the Dns nuclease with a cassette encoding the lacI protein and the T7 RNA polymerase protein (T7 RNAP) where the T7 RNAP protein gene has a modified or weakened ribosome binding site. Induction of T7 RNAP was carried out by culturing in the presence of IPTG, which allowed inducible expression of genes under control of the T7 promoter. A plasmid containing the lacI gene and the gene for the levansucrase enzyme containing its native secretion signal (SEQ ID NO: 9) under the control of the T7 promoter (FIG. 10) was introduced into the strain. An overnight culture was diluted into a minimal media (media is prepared by combining 66 mL 10× phosphate/citric acid buffer (133 g/L $KH_2PO_4$, 40 g/L $(NH4) H_2PO_4$, 17 g/L citric acid, pH 6.3), 27.9 mL 70% glucose, 1.58 mL $MgSO4.7H_2O$ (500 g/L stock), 45.6 mL 5 M NaCl, and 518.92 mL ddH2O, and the pH is adjusted to 6.8) containing 1 mM IPTG (to induce expression of the levansucrase protein) and cultured for 5 hours at 37° C. After 5 hours, cells were collected via centrifugation, and the growth media was filtered to remove additional cells and debris. Secreted proteins were examined by either running various volumes of the spent growth media on an SDS-PAGE gel, or by precipitating the proteins from the growth media using TCA, followed by resuspension in a suitable buffer and running on an SDS-PAGE gel, which showed expected bands for standards and a distinct band at the MW of levansucrase, increasing with concentration, while the rest of the gel was clear (FIG. 11). It was thus shows that when IPTG and the plasmid are present, a protein with the expected size of levansucrase was present in the growth media in high abundance. Quantification of total protein via the Bradford assay shows that about 100 mg/L of protein was secreted from the cells in the 5-hour fermentation (FIG. 11). Thus, IPTG-induced enzyme secretion in the organism containing the plasmid of FIG. 10 is demonstrated.

Although the disclosure has been described with reference to the above examples, it will be understood that modifications and variations are encompassed within the spirit and scope of the disclosure. Accordingly, the disclosure is limited only by the following claims.

What is claimed is:

1. A *Vibrio natriegens* organism comprising:

a recombinant nucleic acid comprising a nucleotide sequence encoding a T7 RNA polymerase and a recombinant regulatory element 5' to the nucleotide sequence encoding the T7 RNA polymerase that regulates expression of the T7 RNA polymerase;

wherein the recombinant nucleic acid further encodes a modified ribosome binding site 5' to the nucleotide sequence encoding the T7 RNA polymerase; and wherein the ribosome binding site comprises the nucleotide sequence of SEQ ID NO: 8, or the nucleotide sequence of SEQ ID NO: 8, except for 1, 2, or 3 nucleotide substitution modification(s) and wherein the ribosome binding site regulates translation of the T7 RNA polymerase.

2. The organism of claim 1, further comprising a heterologous nucleic acid sequence wherein expression of the heterologous nucleic acid sequence is regulated by the T7 RNA polymerase.

3. The organism of claim 1, wherein the recombinant regulatory element comprises.

4. The organism of claim 3, wherein the inducible promoter, the ribosome binding site, and the nucleic acid encoding the T7 RNA polymerase are integrated into chromosome I of the organism.

5. The organism of claim 3, wherein the inducible promoter is induced by arabinose.

6. The organism of claim 3, wherein the inducible promoter is inducible with IPTG.

7. The organism of claim 6, further comprising a lacI repressor for repression of the inducible promoter.

8. The organism of claim 2, wherein the heterologous nucleic acid sequence encodes a heterologous protein, and further encodes a signal sequence for secretion of the heterologous protein.

9. The organism of claim 1, further comprising a deletion of at least one gene encoding an extracellular nuclease.

10. The organism of claim 9, wherein the extracellular nuclease is Dns.

11. The organism of claim 1, having a doubling time of less than 15 minutes.

12. The organism of claim 2, wherein the heterologous nucleic acid sequence is at least 10 kb in size.

13. A method of producing a biomolecule comprising:
   a) contacting the *Vibrio natriegens* organism of claim 1 with a vector comprising a heterologous nucleic acid encoding the biomolecule;
   b) growing the *Vibrio natriegens* organism in a growth-conducive medium wherein the heterologous nucleic acid is expressed, thereby producing the biomolecule; and
   c) isolating the biomolecule.

14. The method of claim 13, wherein the vector comprises the nucleotide sequence of SEQ ID NO: 1, or a nucleotide sequence having 90% or greater sequence identity thereto, wherein the vector is capable of supporting its replication in the *Vibrio natriegens* organism to produce the biomolecule.

15. The method of claim 14, wherein the heterologous nucleic acid is at least 10 kb in size.

16. The method of claim 15, wherein the vector further comprises an inducible promoter operably linked to the heterologous nucleic acid encoding the biomolecule.

17. The method of claim 14, wherein the vector is contacted and introduced into the *Vibrio natriegens* organism by conjugation, chemical competence, natural competence, or electroporation.

18. The method of claim 16, wherein the biomolecule is a protein or peptide.

* * * * *